United States Patent
Li et al.

(10) Patent No.: US 10,869,864 B2
(45) Date of Patent: Dec. 22, 2020

(54) COMBINATIONS FOR THE TREATMENT OF CANCER

(71) Applicant: IGNYTA, INC., San Diego, CA (US)

(72) Inventors: Gang Li, San Diego, CA (US); Ge Wei, San Diego, CA (US); Zachary D. Hornby, San Diego, CA (US); Jonathan Ee-ren Lim, San Diego, CA (US)

(73) Assignee: IGNYTA, INC., South San Francisco, CA (US)

( * ) Notice: Subject to any disclaimer, the term of this patent is extended or adjusted under 35 U.S.C. 154(b) by 0 days.

(21) Appl. No.: 16/063,170

(22) PCT Filed: Dec. 15, 2016

(86) PCT No.: PCT/US2016/066919
§ 371 (c)(1),
(2) Date: Jun. 15, 2018

(87) PCT Pub. No.: WO2017/106492
PCT Pub. Date: Jun. 22, 2017

(65) Prior Publication Data
US 2019/0000840 A1    Jan. 3, 2019

Related U.S. Application Data

(60) Provisional application No. 62/269,805, filed on Dec. 18, 2015, provisional application No. 62/428,498, filed on Nov. 30, 2016.

(51) Int. Cl.

| | | |
|---|---|---|
| A61K 31/496 | (2006.01) | |
| A61K 31/416 | (2006.01) | |
| A61K 31/4439 | (2006.01) | |
| A61K 31/519 | (2006.01) | |
| A61K 31/37 | (2006.01) | |
| A61K 31/44 | (2006.01) | |
| A61K 31/365 | (2006.01) | |
| A61K 31/4523 | (2006.01) | |
| A61K 31/18 | (2006.01) | |
| A61K 31/166 | (2006.01) | |
| A61K 45/06 | (2006.01) | |
| C12Q 1/68 | (2018.01) | |
| C12Q 1/6886 | (2018.01) | |
| A61P 35/00 | (2006.01) | |
| A61K 31/437 | (2006.01) | |

(52) U.S. Cl.
CPC .......... *A61K 31/496* (2013.01); *A61K 31/166* (2013.01); *A61K 31/18* (2013.01); *A61K 31/365* (2013.01); *A61K 31/416* (2013.01); *A61K 31/437* (2013.01); *A61K 31/44* (2013.01); *A61K 31/4439* (2013.01); *A61K 31/4523* (2013.01); *A61K 31/519* (2013.01); *A61K 45/06* (2013.01); *A61P 35/00* (2018.01); *C12Q 1/68* (2013.01); *C12Q 1/6886* (2013.01); *C12Q 2600/106* (2013.01); *C12Q 2600/156* (2013.01)

(58) Field of Classification Search
CPC .... A61K 31/166; A61K 31/18; A61K 31/365; A61K 31/416; A61K 31/437; A61K 31/44; A61K 31/4439; A61K 31/4523; A61K 31/519; A61K 31/496; A61K 45/06; C12Q 11/68; C12Q 11/6886; C12Q 2600/106; C12Q 2600/156; C12Q 1/68; C12Q 1/6886; A61P 35/00
See application file for complete search history.

(56) References Cited

U.S. PATENT DOCUMENTS

| | | | |
|---|---|---|---|
| 4,555,402 A | 11/1985 | Matsuda et al. | |
| 6,469,004 B1 * | 10/2002 | Barrett ................ | C07D 235/06 514/248 |
| 7,015,231 B2 | 3/2006 | Lackey et al. | |
| 7,230,098 B2 | 6/2007 | Cui et al. | |
| 7,534,792 B2 | 5/2009 | Wittman et al. | |
| 7,790,756 B2 | 9/2010 | Flynn et al. | |
| 7,799,782 B2 | 9/2010 | Munson et al. | |
| 7,964,592 B2 | 6/2011 | Garcia-Echeverria et al. | |
| 8,114,865 B2 | 2/2012 | Bandiera et al. | |
| 8,114,989 B2 | 2/2012 | Wang et al. | |
| 8,299,057 B2 | 10/2012 | Lombardi Borgia et al. | |
| 8,372,858 B2 | 2/2013 | Michellys et al. | |
| 8,404,846 B2 | 3/2013 | Claridge et al. | |
| 8,497,284 B2 | 7/2013 | Bannen et al. | |
| 8,513,263 B2 | 8/2013 | Haas et al. | |

(Continued)

FOREIGN PATENT DOCUMENTS

| | | |
|---|---|---|
| CN | 101594862 | 12/2009 |
| CN | 101754956 | 6/2010 |

(Continued)

OTHER PUBLICATIONS

Infante et. al., Lancet Oncology, 2012, vol. 13, pp. 773-781 (Year: 2012).*

(Continued)

*Primary Examiner* — Sarah Pihonak
(74) *Attorney, Agent, or Firm* — Foley & Lardner LLP

(57) ABSTRACT

Described herein are combinations comprising a therapeutically effective amount of a first agent and a therapeutically effective amount of a second agent, wherein the first agent is an inhibitor of ALK, ROS1, TrkA, TrkB, or TrkC activity, or a combination thereof, and methods of using such combinations in the treatment of patients having cancer.

15 Claims, 3 Drawing Sheets
Specification includes a Sequence Listing.

(56) References Cited

U.S. PATENT DOCUMENTS

| | | | |
|---|---|---|---|
| 8,673,893 | B2 | 3/2014 | Lombardi Borgia et al. |
| 8,680,111 | B2 | 3/2014 | Bailey et al. |
| 9,102,662 | B2 | 8/2015 | Lombardi Borgia et al. |
| 10,085,979 | B2 | 10/2018 | Hornby et al. |
| 10,231,965 | B2 | 3/2019 | Lim et al. |
| 10,357,490 | B2 | 7/2019 | Hornby et al. |
| 10,398,693 | B2 | 9/2019 | Codallos et al. |
| 10,561,651 | B2 | 2/2020 | Lim et al. |
| 2004/0014802 | A1 | 1/2004 | Dutruc-Rosset et al. |
| 2005/0014829 | A1 | 1/2005 | Remenar et al. |
| 2009/0263397 | A1 | 10/2009 | Buck et al. |
| 2010/0197665 | A1 | 8/2010 | Bandiera et al. |
| 2013/0018036 | A1 | 1/2013 | Lombardi Borgia et al. |
| 2014/0107107 | A1 | 4/2014 | Gautschi et al. |
| 2015/0051222 | A1 | 2/2015 | Barbugian et al. |
| 2015/0283132 | A1 | 10/2015 | Lim et al. |
| 2017/0007599 | A1 | 1/2017 | Lim et al. |
| 2017/0065582 | A1 | 3/2017 | Hornby et al. |
| 2017/0260589 | A1* | 9/2017 | Nanda .................. A61K 31/5025 |
| 2018/0177792 | A1 | 6/2018 | Wei |
| 2018/0333412 | A1 | 11/2018 | Lim et al. |
| 2019/0000840 | A1 | 1/2019 | Li et al. |
| 2019/0022089 | A1 | 1/2019 | Codallos et al. |
| 2019/0070173 | A1 | 3/2019 | Hornby et al. |
| 2019/0282564 | A1 | 9/2019 | Lim et al. |

FOREIGN PATENT DOCUMENTS

| | | | |
|---|---|---|---|
| CN | 102924479 A | 2/2013 | |
| JP | 2002-275068 A | 9/2002 | |
| JP | 2010-530840 A | 9/2010 | |
| JP | 2011-502959 A | 1/2011 | |
| WO | WO-99/43302 A1 | 9/1999 | |
| WO | WO-03/051847 A1 | 6/2003 | |
| WO | WO-03/078403 A2 | 9/2003 | |
| WO | WO-2004/007676 | 1/2004 | |
| WO | WO-2004/022544 A1 | 3/2004 | |
| WO | WO-2004/062662 A1 | 7/2004 | |
| WO | WO-2004/075898 A1 | 9/2004 | |
| WO | WO-2005/040413 A1 | 5/2005 | |
| WO | WO-2006/003276 A1 | 1/2006 | |
| WO | WO-2006/080450 A1 | 8/2006 | |
| WO | WO-2006/111035 A1 | 10/2006 | |
| WO | WO-2007/017497 A2 | 2/2007 | |
| WO | WO-2007/075847 A2 | 7/2007 | |
| WO | WO-2008/003396 A1 | 1/2008 | |
| WO | WO-2008/073480 A1 | 6/2008 | |
| WO | WO-2008/074749 A1 | 6/2008 | |
| WO | WO-2009/013126 A1 | 1/2009 | |
| WO | WO-2013/119950 A2 | 8/2013 | |
| WO | WO-2013/174876 A1 | 11/2013 | |
| WO | WO-2014/093750 A1 | 6/2014 | |
| WO | WO-2015/124697 A1 | 8/2015 | |
| WO | WO-2015/175788 A1 | 11/2015 | |
| WO | WO-2015/189814 A1 | 12/2015 | |
| WO | WO-2016/089760 A1 | 6/2016 | |
| WO | WO-2016/089853 A1 | 6/2016 | |
| WO | WO 2016/19614 A1 | 12/2016 | |
| WO | WO-2016196671 A1 * | 12/2016 | ........... C12Q 1/6886 |
| WO | WO-2017/106492 A1 | 6/2017 | |
| WO | WO 2019/018570 A1 | 1/2019 | |
| WO | WO 2019/077506 A1 | 4/2019 | |

OTHER PUBLICATIONS

Sikora, Personalized Medicine, 2005, Future Med. Ltd, vol. 2(1), pp. 5-9 (Year: 2005).*

Cao et. al., Nature Reviews Cancer, 2011, Nature Pub. Group, vol. 11, pp. 749-754 (Year: 2011).*

Marshall et. al., Investigational New Drugs, 2005, vol. 23, pp. 31-37 (Year: 2005).*

Bhatia et. al., Nature Biotechnology, 2012, Nature America Inc., vol. 30(7), pp. 604-610 (Year: 2012).*

Chan, LiveScience, "The 10 Deadliest Cancers and Why There's No Cure", 2010, webpage https://www.livescience.com/11041-10-deadliest-cancers-cure.html (Year: 2010).*

Holt et. al., British Journal of Cancer, 2012, Nature Publishing Group, vol. 106, pp. 858-866 (Year: 2012).*

Iyer et al., "Abstract 5390: The TRK inhibitor RXDX-101 enhances the efficacy of temozolomide and irinotecan in xenograft model of neuroblastoma," Cancer Research, (2015), 75(15):Supplemental p. 5390.

Li et al., "Abstract A173: Potent anti-tumor activity of entrectinib in patient-derived models harboring oncogenic gene rearrangements of NTRKs," Molecular Cancer Therapeutics, (2015), 14(12):Supplement 2, p. A173.

PCT International Preliminary Report on Patentability (Chapter II) for Application No. PCT/US2016/066919, dated Dec. 7, 2017. (22 pages).

PCT International Search Report and Written Opinion dated Apr. 21, 2017 in PCT Patent Application No. PCT/US2016/066919. (26 pages).

Russo et al., "Acquired Resistance to the TRK Inhibitor Entrectinib in Colorectal Cancer," Cancer Discovery, (2016), 6:36-44.

U.S. Appl. No. 16/249,703, filed Jan. 16, 2019, Ignyta, Inc.

A. Greco et al, "Rearrangements of NTRK1 gene in papillary thyroid carcinoma," Molecular and Cellular Endocrinology, (May 2010), vol. 321, No. 1, ISSN 0303-7207, pp. 44-49.

Adriaenssens, E. et al., Nerve growth factor is a potential therapeutic target in breast cancer, Cancer Res, Jan. 15, 2008, 68(2):346-351.

Albaugh, P. et al., Discovery of GNF-5837, a selective TRK inhibitor with efficacy in rodent cancer tumor models, Med. Chem. Lett, 2012, 3:140-145.

Alecensa® (alectinib) capsules, for oral use, Prescribing Information, Dec. 2015, 16 pp.

Asaumi, K. et al., Expression of neurotrophins and their receptors (TRK) during facture healing, Bone, Jun. 2000, 26(6);625-633.

Aveic et al., "Study of pan-Trk, ROS1, ALK inhibitor, RXDX-101, activity on human neuroblastoma cell lines", Brochure, SIOPEN Annual Meeting 2014, Apr. 23-25, 2014. (1 page).

Awad et al., "ALK inhibitors in non-small cell lung cancer: crizotinib and beyond", Clin Adv Hemotol Oncol, Jul. 2014, 12(7):429-439.

Bardelli, A. et al., Mutational analysis of the tyrosine kinome in colorectal cancers, Science, 2003, 300:949.

Bardelli, A. et al., Mutational analysis of the tyrosine kinome in colorectal cancers, Science, 2003, 300:949; Supplemental Material.

Baserga, R. et al., The IGF-I receptor in cell growth, transformation and apoptosis, Biochip Biophys Acta, 1997, 1332:F105-F126.

Bavetsias, V. et al., Hit generation and exploration: imidazo[4,5-b]pyridine derivatives as inhibitors of aurora kinases, Bioorganic & Medicinal Chemistry Letters, 2007, 17:6567-6571.

Bergethon, K. et al., ROS1 rearrangements define a unique molecular class of lung cancers, Journal of Clinical Oncology, Mar. 10, 2012, 30(8):863-870.

Bouhana, K. et al., LOXO-101, a pan TRK inhibitor, for the treatment of TRK-driven cancers, 26th EORTC-NCI-AACR Symposium on Molecular Targets and Cancer Therapeutics, Barcelona, Spain, Poster, Nov. 2014, Abstract #291, 1 p.

Brodeur, G. M., Neuroblastoma: biological insights into a clinical enigma, Nat. Rev. Cancer, Mar. 2003, 3:203-216.

Brodeur, GM, et al. Trk receptor expression and inhibition in neuroblastomas. Clin Cancer Res. May 15, 2009;15(10):3244-50.

Broekman, F. et al., Tyrosine kinase inhibitors: multi-targeted or single-targeted?, World J. Clin Oncol, Feb. 10, 2011, 2(2):80-93.

Brose, M. et al., LOXO-101, a selective pan-TRK inhibitor for patients with TRK-alterations 15th International Thyroid Congress, Oct. 2015, Lake Buena Vista, Florida, Poster, 1 p.

Brzezianska, E. et al., Rearrangements of NTRK1 oncogene in papillary thyroid carcinoma, Neuroendocrinology Letters, 2007, 28(3):221-229.

Burris, H. A., III. et al., A first-in-human study of LOXO-101, a highly selective inhibitor of the tropomyosin receptor kinase (TRK) family, American Society of Clinical Oncology (ASCO) 2015 Annual Meeting, May-Jun. 2015, Chicago, IL, Poster, 1 p.

Calvo, E., Posters Discussion: Developmental Therapeutics, 2014 ESMO Congress, Sep. 26-30, 2014, 21 pp.

(56) References Cited

OTHER PUBLICATIONS

Cho, H. et al., Expression of mRNA for brain-derived neurotrophic factor in the dorsal root ganglion following peripheral inflammation, Brain Research, 1997, 749:358-362.
ClinicalTrials.gov, Aug. 20, 2014, A phase 1/2a study of oral RXDX-101 in adult patients with locally advanced or metastatic cancer; study targeting ALK, ROS1 or TRKA/8/C (STARTRK:1), 4 pp.
ClinicalTrials.gov, Aug. 2014, A phase 1/2a study of oral RXDX-101 in adult patients with locally advanced or metastatic cancer; study targeting ALK, ROS1 or TRKA/8/C, 36 pp.
ClinicalTrials.gov, Sep. 11, 2014, A phase 1/2a study of oral RXDX-101 in adult patients with locally advanced or metastatic cancer; study targeting ALK, ROS1 or TRKA/8/C (STARTRK-1), 7 pp.
Cohen, P., Protein kinases—the major drug targets of the twenty-first century?, Nature Reviews, Apr. 2002, Drug Discovery 1:309-315.
Cohen, P., The development and therapeutic potential of protein kinase inhibitors, Current Opinion in Chemical Biology, 1999, 3:459-465.
Collymore, D. C. et al., Genomic testing in oncology to improve clinical outcomes while optimizing utilization: the evolution of diagnostic testing, American Journal of Managed Care, Feb. 2016, 22(2):S20-S28.
Croucher et al., "TrkB inhibition by GNF-4256 slows growth and enhances chemotherapeutic efficacy in neuroblastoma xenografts", Cancer Chemother Pharmacol, 2015, 75:131-141.
Dang, C. et al., Expression of nerve growth factor receptors is correlated with progression and prognosis of human pancreatic cancer, Journal of Gastroenterology and Hepatology, 2006, 21(5):850-858.
Davidson, B. et al., Expression and activation of the nerve growth factor receptor TrkA in serous ovarian carcinoma, Clin. Cancer Res., Jun. 2003, 9:2248-2259.
Davies, K. D. et al., Resistance of ROS1 inhibition mediated by EGFR pathway activation in non-small cell lung cancer, PIOS One, Dec. 2013, 8(12):e82236.
Davies, K. et al., Identifying and targeting ROS1 gene fusions in non-small cell lung cancer, Clin Cancer Res, Sep. 1, 2012, 18(17):4570-4579.
De Braud, F. et al., 2014, Phase 1 open label, dose escalation study of RXDX-101, an oral pan-trk, ROS1, and ALK inhibitor, in patients with advanced solid tumors with relevant molecular alterations, Poster, 1P.
De Braud, F. et al., 2014, RXDX-101, an oral pan-TRK, POS1, and ALK inhibitor, in patients with advanced solid tumors with relevant molecular alterations, Annals of Oncology 25(Supplement 4):iv146-iv164 (abstract).
De Braud, F., 2014, Phase 1 open label, dose escalation study of RXDX-101, an oral pan-trk, ROS1, and ALK inhibitor, in patients with advanced solid tumors with relevant molecular alterations, PowerPoint presentation, ASCO 50th Annual Meeting, 18 pp.
De Melo-Jorge, M. et al., The chagas' disease parasite trypanosoma cruzi exploits nerve growth factor receptor TrkA to infect mammalian hosts, Cell Host & Microbe, Jun. 2007, 1(4):251-261.
Delafoy, L. et al., Role of nerve growth factor in the trinitrobenzene sulfonic acid-induced colonic hypersensitivity, Pain, 2003, 105:489-497.
Di Mola, F. F. et al., Nerve growth factor and Trk high affinity receptor (TrkA)gene expression in inflammatory bowel disease, Gut, 2000, 46(5):670-678.
Dionne, C. A. et al., Cell cycle-independent death of prostate adenocarcinoma is induced by the trk tyrosine kinase inhibitor CEP-751 (KT6587), Clin. Cancer Res., Aug. 1998, 4(8):1887-1898.
Doebele, R. C. et al., An oncogenic NTRK fusion in a patient with soft-tissue sarcoma with response to the tropomyosin-related kinase inhibitor LOXO-101, Cancer Discovery, Oct. 2015, 1049-1057.
Dou, Y. et. al., 2006, Increased nerve growth factor and its receptors in atopic dermatitis: an immunohistochemical study, Archives of Dermatological Research, 2008, 298(1):31-37.

Drilon et al., "Safety and Antitumor Activity of the Multitargeted Pan-TRK, ROS1, and ALK Inhibitor Entrectinib: Combined Results from Two Phase I Trials (ALKA-372-001 and STARTRK-1)", Published OnlineFirst Feb. 9, 2017, Downloaded from cancerdiscovery.aacrjournals.org on Apr. 7, 2017, pp. 401-409.
Drug Class Detail: Trk Receptor Inhibitor (Pan); https://ckb.jax.org/drugClass/show?drugClassId=Trk Receptor Inhibitor %28Pan%29: (Jul. 16, 2014).
Duffy, M. J. et al., Companion biomarkers: paving the pathway to personalized treatment for cancer, Clinical Chemistry, 2013, 59(1):1447-1456.
Ep Search Report for Application No. 15865371.7 dated Jul. 4, 2018 (10 pages).
Estrada-Bernal et al., "TRK kinase domain mutations that induce resistance to a pan-TRK inhibitor," [abstract]. In: Proceedings of the AACR-NCI-EORTC International Conference: Molecular Targets and Cancer Therapeutics; Nov. 5-9, 2015; Boston, MA. Philadelphia (PA): AACR; Mol Cancer Ther 2015;14(12 Suppl 2):Abstract nr C65.
Evans et al., "Antitumor Activity of CEP-751 (KT-6587) on Human Neuroblastoma and Medulloblastoma Xenografts," American Association for Cancer Research, 1999, 5:3594-3602.
Extended European Search Report issued in European Patent Application No. 16804039.2 dated Nov. 16, 2018.
Freund-Michel, V. et al., The nerve growth factor and its receptors in airway inflammatory diseases, Pharmacology & Therapeutics, 2008, 117(1):52-76.
Gad et al., "Neurotrophic activities of trk receptors conserved over 600 million years of evolution", J. Neurobiol., 2004;60(1):12-20.
Gainor, Justin, MD,RXDX-101 & RXDX-102, Powerpoint Presentation, Feb. 20, 2014, 13 pp.
Greco, A. et al., Rearrangement of NKRK1 gene in papillary thyroid carcinoma, Molecular and Cellular Endocrinology, May 1, 2010, 321(1):44-49.
Hansen, K. et al., Autophagic cell death induced by TrkA receptor activation in human glioblastoma cells, Journal of Neurochemistry, 2007, 103:259-275.
Hofmann, F. et al., Blocking insulin-like growth factor-I receptor as a strategy for targeting cancer, Drug Discov Today, Aug. 2005, 10(15):1041-1047.
Hu, V. Y. et al., Decrease in bladder overactivity with ren1820 in rats with cyclophosphamide induced cystitis, The Journal of Urology, 2005, 173(3):1016-1021.
Hu, Y. et al., Identification of brain-derived neurotrophic factor as a novel angiogenic protein in multiple myeloma, Cancer Genetics and Cytogenetics, 2007, 178:1-10.
Iannone et al., "Increased expression of nerve growth factor (NGF) and high affinity NGF receptor (p140 TrkA) in human osteoarthritic chondrocytes", Rheumatology, 2002;41:1413-1418.
Ignyta Inc., Aug. 12, 2014, Ignyta announces second quarter 2014 company highlights and financial results, Press Release, 4 pp.
Ignyta Inc., Dec. 3, 2013, Ignyta announces completion of $54 million in private placements to catalyze precision medicine for cancer patients, Press Release, 2 pp.
Ignyta Inc., Feb. 20, 2014, Ignyta announces preliminary data from RXDX-101 phase I clinical trial, Press Release, 2 pp.
Ignyta Inc., Feb. 27, 2014, Ignyta announces of IND for RXDX-101, Press Release, 2 pp.
Ignyta Inc., Feb. 28, 2014, Ignyta announces 2013 company highlights and full year financial results, Press Release, 5 pp.
Ignyta Inc., Jul. 21, 2014, Ignyta announces initiation of STARTKR-1 global phase I/II clinical trial of RXDX-101, Press Release, 2 pp.
Ignyta Inc., May 31, 2014, Ignyta announces interim data from RXDX-101 phase I clinical trial, Press Release, 2 pp.
Ignyta Inc., May 7, 2014, Ignyta announces RXDX-101 phase I data abstract accepted for oral presentation at the 2014 ASCO annual meeting, Press Release, 2 pp.
Ignyta Inc., Nov. 1, 2013, Ignyta completes merger and announces license agreement for the development of two leading tyrosine kinase inhibitors, Press Release, 1 p.
Ignyta Inc., Nov. 18, 2014, Ignyta announces RXDX-101 phase 1 presentations at the 2014 EORTC-NCI-AACR 'molecular targets and cancer therapeutics' conference, Press Release, 2 pp.

(56) References Cited

OTHER PUBLICATIONS

Ignyta Inc., Nov. 7, 2014, Ignyta announces third quarter 2014 company highlights and financial results, Press Release, 5 pp.
Ignyta Inc., Sep. 15, 2014, Ignyta announces RXDX-101 phase 1 data presentation at the 2014 ESMO Congress, Press Release, 2 pp.
Ignyta Inc., Sep. 28, 2014, Ignyta announces interim data from RXDX-101 phase I clinical trial at 2014 ESMO Congress, Press Release, 2 pp.
Ignyta, Feb. 2014, Catalyzing precision medicine with integrated Rx/Ox in oncology, presentation, 23 pp.
Ignyta, Inc., Feb. 20, 2014, Form 8-K (Current Report Filing), 20 pp.
Ignyta, Inc., Jan. 13, 2014, Form 8-K (Current Report Filing), 28 pp.
Ignyta, Inc., Jun. 2, 2014, Form 8-K (Current Report Filing), 26 pp.
Ignyta, Inc., May 12, 2014, Form 8-K (Current Report Filing), 11 pp.
Ignyta, Inc., May 2, 2014, Form 8-K (Current Report Filing), 4 pp.
Ignyta, Inc., Nov. 7, 2014, Form 8-K (Current Report Filing), 13 pp.
Ignyta, Inc., Oct. 14, 2014, Form 8-K (Current Report Filing), 61 pp.
International Search Report and Written Opinion for Application No. PCT/US2015/062975, dated Feb. 12, 2016, 16 pages.
International Search Report and Written Opinion issued in PCT/IB2018/058031 dated Feb. 12, 2019.
International Search Report for international application No. PCT/EP2015/053544 dated Mar. 30, 2015.
International search report issued in PCT/US2018/042756 dated Nov. 12, 2018.
Isaacson, Jerry, Ph.D. et al., "Ignyta, Inc.: Initiation of Coverage," LifeSci Advisors Research, Feb. 14, 2014, pp. 1-37.
Iyer et al., "AZ64 inhibits TrkB and enhances the efficacy of chemotherapy and local radiation in neuroblastoma xenografts", Cancer Chemother Pharmacol, 2012, 70:477-486.
Iyer et al., "Lestaurtinib Enhances the Antitumor Efficacy of Chemotherapy in Murine Xenograft Models of Neuroblastoma", Clin Cancer Res; 2010; 16(5):1478-1485.
Iyer et al., "Abstract 5390: The TRK Inhibitor RXDX-101 enhances the efficacy of temozolomide and irinotecan in a xenograft model of neuroblastoma," Cancer Research, Aug. 1, 2015, vol. 75, Iss. 15, Supplement, p. 5390.
Jaggar, S. I. et al., Inflammation of the rat urinary bladder is associated with a referred thermal hyperalgesia which is nerve growth factor dependent, Br. J. Anaesth., 1999, 83:442-448.
Jantzen, G. M. et al., "Sustained- and controlled-release drug delivery systems", in Banker et al. eds., Modern Pharmaceutics, 1996, 3rd Ed. pp. 575-609, Marcel Dekker, Inc., New York, NY.
Johnson, T. W. et al., Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a macrocyclic inhibitor of anaplastic lymphoma kinase (ALK) and c-ros oncogene 1(ROS1) with preclinical brain exposure and broad-spectrum potency against ALK-resistant mutations, Journal of Medicinal Chemistry, 2014, 57(11);4720-4744.
Karaman, M. W. et al., A quantitative analysis of kinase inhibitor selectivity, Nature Biotechnology, Jan. 2008, 26(1):127-132.
Khandwala, H. M. et al., The effects of insulin-like growth factors on tumorigenesis and neoplastic growth, Endocr Rev, 2000, 21(3):215-244.
Kruettgen, A. et al., The dark side of the NGF family: neurotrophins in neoplasias, Brain Pathology, 2006, 16:304-310.
Kushner, BH, et al. Irinotecan plus temozolomide for relapsed or refractory neuroblastoma. J Clin Oncol. Nov. 20, 2006;24(33):5271-6.
Lamant et al., 2000, Expression of the ALK tyrosine kinase gene in neuroblastoma, American Journal of Pathology, 156:1711-1721.
Lamb, K. et al., Nerve growth factor and gastric hyperalgesia in the rat, Neurogastroenterol. Motil, 2003, 15:355-361.

Laron, Z., Laron syndrome (primary growth hormone resistance or insensitivity): the personal experience 1958-2003, J Clin Endocrinol Metab, 2004, 89(3):1031-1044.
Le Roith, D. et al., The somatomedin hypothesis: 2001, Endocr Rev, 2001, 22(1):53-74.
Lee et al., "Mechanisms of Constitutive Activation of Janus Kinase 2-V617F Revealed at the Atomic Level Through Molecular Dynamics Simulations 1," Cancer, vol. 115, No. 8, pp. 1692-1700 (2009).
Lee, J. et al., Identification of ROS1 rearrangement in gastric adenocarcinoma, Cancer, May 1, 2013, 119:1627-1635.
Lewis et al., "The Discovery and Optimization of a Novel Class of Potent, Selective, and Orally Bioavailable Anaplastic Lymphoma Kinase (ALK) Inhibitors with Potential Utility for the Treatment of Cancer", Journal of Medicinal Chemistry, 2012;55(14): 6523-6540.
Li, Q. et al., Brain derived neurotrophic factor (BDNF) contributes to the pain hypersensitivity Following surgical incision in the rats, Molecular Pain, 2008, 4:27, 11 pp.
Li, T. et al., Genotyping and genomic profiling of Non-Small-Cell lung cancer: implications for current and future therapies, Journal of Clinical Oncology, Mar. 10, 2013, vol. 31, No. 8, pp. 1039-1049.
Lindeman, N. I., MD et al., Molecular testing guideline for selection of lung cancer patients for EGFR and ALK tyrosine kinase inhibitors, Journal of Thoracic Oncology, Jul. 2013, 8(7):823-859.
Lipska Beata S et al, "c.1810C>T Polymorphism of NTRK1 Gene is associated with reduced Survival in Neuroblastoma Patients", BMC Cancer, Biomed Central, London, GB, (Dec. 2009), vol. 9, No. 1, ISSN 1471-2407, p. 436.
Ma, Q. et al., The progressive tactile hyperalgesia induced by peripheral inflammation is nerve growth factor dependent, Neuroreport, 1997, 8(4):807-810.
Marchetti, A. et al., Frequent mutations in the neurotrophic tyrosine receptor kinase gene family in large cell neuroendocrine carcinoma of the lung, Human Mutation, 2008, 29(5):609-616.
Marsilje, T. H. et al., Synthesis, structure-activity relationships and in vivo efficacy of the novel potent and selective anaplastic lymphoma kinase (ALK) inhibitor LDK378 currently in phase 1 and 2 clinical trials, J. Med. Chem., 2013, 56:5675-5690 and Supporting Information.
Matayoshi, S. et al., Actions of brain-derived neurotrophic factor on spinal nociceptive transmission during inflammation in the rat, J. Physiol., 2005, 569(2):685-695.
McMahon, S. B. et al., The biological effects of endogenous nerve growth factor on adult sensory neurons revealed by a trkA-IgG fusion molecule, Nat. Med., Aug. 1995, 1(8):774-780.
Meyer, J. et al., Remarkable leukemogenic potency and quality of a constitutively active neurotrophin receptor, ΔTrkA, Leukemia, 2007, 21:2171-2180.
Milkeiwicz, K. L. et al., Inhibitors of anaplastic lymphoma kinase: a patent review, Expert Opin. Ther. Patents, 2010, 20(12):1653-1681.
Minturn et al, "Phase I trial of lestaurtinib for children with refractory neuroblastoma: a new approaches to neuroblastoma therapy consortium study," Cancer Chemother Pharmacol, Feb. 22, 2011, 9 pages.
Molina-Vila, M. A. et al., Impact of the new EGF receptor and ALK testing guideline on personalized lung cancer medicine, Personalized Medicine, 2013, 19(5):415-417.
Murphy et al., "Monitoring activity of RXDX-101 in Phase 1/2 patients using a pharmacodynamics assay for TrkA activation", European Journal of Cancer, Poster Session—Molecular Targeted Agents II, 2014, 50(6):143-144.
Nakagawara et al.; "Association between high levels of expression of the Trk gene and favorable outcome in human neuroblastoma"; N Engl J Med; 1993; 328:847-54.
Nakagawara, A., Trk receptor tyrosine kinases: a bride between cancer and neural development, Cancer Letters, 2001, 169:107-114.
National Comprehensive Cancer Network, NCCN Clinical Practice Guidelines in Oncology: Non-small cell lung cancer, Apr. 2016, Version Apr. 2016. 169 pp.
Okimoto, R. A. et al., Recent advances in personalized lung cancer medicine, Personalized Medicine, 2014, 11(3):309-321.

(56) References Cited

OTHER PUBLICATIONS

Omura et al., "A New Alkaloid AM-2282 of Streptomyces Origin Taxonomy, Fermentation, Isolation and Preliminary Characterization", Journal of Antibiotics, 1977, 30(4):275-282.
Pardue et al., "Nucleic Acid Hybridization. A practical approach", IRL Press, Oxford Washington/DC. 1985:170-203.
Patapoutian, A. et al., TRK receptors: mediators of neurotrophin action, Current Opinion in Neurobiology, 2001, 11:272-280.
PCT International Search Report and Written Opinion for PCT/US2016/034166 dated Oct. 19, 2016. (18 pages).
Perez-Pinera,P. et al., The Trk tyrosine kinase inhibitor K252a regulates growth on lung adenocarcinomas, Molecular and Cellular Biochemistry, 2007, 295:19-26.
Pierotti, A. et al., Oncogenic rearrangements of the NRTK1/NGF receptor, Cancer Letters, 2006, 232:90-98.
Pinski, J. et al., Trk receptor inhibition induced apoptosis of proliferating but not quiescent human osteoblasts, Cancer Research, Feb. 15, 2002, 62:986-989.
Puig De La Bellacasa, R. et al., ALK and ROS1 as a joint target for the treatment of lung cancer: a review, Translational Lung Cancer Research, 2013, vol. 2, No. 2, pp. 72-86.
Raychaudhuri, S. P. et al., K252a, a high-affinity nerve growth factor receptor blocker, improves psoriasis: an in vivo study using the severe combined immunodeficient mouse-human skin model, Journal of Investigative Dermatology, Mar. 3, 2004, 122(3);812-819.
Sakamoto, H. et al., CH5424802, a selective ALK inhibitor capable of blocking the resistant gatekeeper mutant, Cancer Cell, 2011, 19:679-690.
Shaw, A. T. et al., Crizotinib versus chemotherapy in advanced ALK-positive lung cancer, The New England Journal of Medicine, Jun. 30, 2013, 268(25):2385-2394.
Shaw, A. T. et al., Targeting anaplastic lymphoma kinase in lung cancer, Clin. Cancer Res., 2011, 17:2081-2086.
Shelton et al., Nerve growth factor mediates hyperalgesia and cachexia in auto-immune arthritis, Pain, 2005, 116:8-16.
Sohrabji et al., Estrogen-BDNF interactions: implications for neurodegenerative diseases, Neuroendocrinology, 2006, 27(4):404-414.
Stumpfova et al., Zeroing in on ROS1 rearrangements in non-small cell lung cancer, Clin Cancer Res, Aug. 2, 2012, 18(16):4222-4224.
Tatematsu et al., Investigation of neurotrophic tyrosine kinase receptor 1 fusions and neurotrophic tyrosine kinase receptor family expression in non-small-cell lung cancer and sensitivity to AZD7451 in vitro, Molecular and Clinical Oncology, 2014, 2:725-730.
Thompson et al., Brain-derived neurotrophic factor is an endogenous modulator of nociceptive responses in the spinal cord, Proc. Natl. Acad. Sci. USA, Jul. 1999, 96:7714-7718.
Tremodar PI-2, Highlights or Prescribing Information, 2014. (17 pages).
Truzzi et al., Neurotrophins and their receptors stimulate melanoma cell proliferation and migration, Journal of Investigative Dermatology, 2008, 128(8):2031-2040.
Tzelepi, V., Editorial: Personalized cancer treatment, Current Molecular Pharmacology, 2014, 7(1), 2 pp.
Uniprot Accession P04629. "NTRK1_human", (Jun. 24, 2015), available on the internet: http://www.uniprot.org/uniprot/P04629.txt?version=204 (12 pages).
Vaishnavi et al., Oncogenic and drug sensitive NTRK1 rearrangements in lung cancer, Nat Med., Nov. 2013, 19(11):1469-1472.
Valent et al. Mapping of the tyrosine kinase receptors trkA (NTRK1), trkB (NTRK2) and trkC(NTRK3) to human chromosomes 1q22, 9q22 and 15q25 by fluorescence in situ hybridization. Eur.J. Hum. Genet (1997), vol. 5(2), pp. 102-104.
Valentinis et al., IGF-I receptor signaling in transformation and differentiation, 2001, Mol Pathol, 54:133-137.
Vasconcelos et al., "Solid dispersions a strategy to improve oral bioavailability of poor water soluble drug," Drug Discovery Today, vol. 12, Jan. 2012, pp. 1068-1075.
Voskoglou-Nomikos et al., Clinical predictive value of the in vitro cell line, human xenograft, and mouse allograft preclinical cancer models, Clinical Cancer Research, Sep. 15, 2003, 9:4227-4239.
Wang et al., Insulin-like growth factor receptor-1 as an anti-cancer target: blocking transformation and inducing apoptosis, Curr Cancer Drug Targets, 2002, 2:191-207.
Warner et al., Targeting aurora-2 kinase in cancer, Molecular Cancer Therapeutics, Jun. 3, 2003, 2:589-595.
Wei et al., "Abstract 2136: Entrectinib is effective against the gatekeeper and other emerging resistance mutations in NTRK-, ROS1- and ALK-rearranged cancers", [abstract], Proceedings: AACR 107th Annual Meeting 2016; Apr. 16-20, 2016: New Orleans, LA; 2016;76(14 Suppl):Abstract nr 2136.
Weroha et al., IFG-1 receptor inhibitors in clinical trials—early lessons, J. Mammary Gland Biol. Neoplasia, 2008, vol. 13, pp. 471-483.
Wolff, M.E., Burger's Medicinal Chemistry and Drug Discovery, 5th Ed. vol. 1, 1995, pp. 975-977, John Wiley & Sons, Inc., New York, NY.
Wood et al., "Somatic Mutations of GUCY2F, EPHA3, and NTRK3 in Human Cancers", Human Mutation in Brief #923, 2006. (9 pages).
Woolf et al., Letter to Neuroscience: Nerve growth factor contributes to the generation of inflammatory sensory hypersensitivity, Neuroscience, 1994, vol. 62, No. 2, pp. 327-331.
Written Opinion and Search Report for Singapore Application No. 11201605861 dated Feb. 16, 2017.
Written Opinion of the International Searching Authority for international application No. PCT/EP2015/053544 dated Aug. 27, 2015.
Xalkori® (crizotinib) capsules, for oral use, Prescribing Information, Mar. 2016, 27 pp.
Zahn et al., Effect of blockade of nerve growth factor and tumor necrosis factor on pain behaviors after plantar incision, J. Pain, vol. 5 No. 3, Apr. 2004, pp. 157-163.
Zhu et al., "Nerve Growth Factor Expression Correlates With Perineural Invasion and Pain in Human Pancreatic Cancer", Journal of Clinical Oncology, 1999;17:2419-2428.
Zhu et al. Implications of tropomyosin-related kinase B (TrkB) in head and neck cancer. Anticancer Res. Sep.-Oct. 2007;27(5A):3121-6.
Zykadia™ (ceritinib) capsules, for oral use, Prescribing Information, Apr. 2014, 16 pp.
Brodeur et al., "TrK Receptor Expression and Inhibition in Neuroblastomas," Clinical Cancer Research, 15(10), pp. 3244-3250, 2009.
Iyer, R., et al., Entrectinib is a Potent Inhibitor of TRK-Driven Neuroblastomas in a Xenograft Mouse Model, Cancer Letters 372 (2016) pp. 179-186, http://dx.doi.org/10.1016/j.canlet.2016.01.018.
Nakagawara,A., et al., Expression and Function of TRK-B and BDNF in Human Neuroblastomas, Molecular and Cellular Biology,Jan. 1994, p. 759-767.
Hatcher, John M. et al: "Discovery of Inhibitors That Overcome the G1202R Anaplastic Lymphoma Kinase Resistance Mutation", Journal of Medicinal Chemistry, vol. 58, No. 23, Nov. 25, 2015 (Nov. 25, 2015), pp. 9296-9308, XP055603442, US ISSN: 0022-2623, DOI: 10.1021 /acs.jmedchem.5b01136.
Ho A et al: "Overcoming drug resistance to Trk inhibition by rational combination of entrectinib and trametinib: from bench to bedside", European Journal of Cancer, vol. 69, Dec. 2, 2016, XP029843502, ISSN: 0959-8049, DOI: 10.1016/S0959-8049(16)32615-6.
Ignyta, "Overcoming drug resistance to TRK inhibition by rational combination of entrectinib and trametinib: from bench to bedside", 28th EORTC-NCI-AACR symposium, Nov. 1, 2016, XP055603929, Retrieved from the Internet: URL:https://pdfs.semanticscholar.org/9270/3fe8a73b37ee47aa4b0af036f1 ea762348de.pdf [retrieved on Jul. 9, 2019].
Ming Chi et al: "Targeted drug development in melanoma and nonsmall cell lung cancer: BRAF, MEK, and ALK inhibitors", MEMO—Magazine of European Medical Oncology, Springer Vienna, Vienna, vol. 5, No. 4, Nov. 20, 2012, pp. 302-308, XP035152606, ISSN: 1865-5076, DOI: 10.1007/S12254-012-0058-4.

(56) References Cited

OTHER PUBLICATIONS

Tanizaki, J. et al: "Combined effect of ALK and MEK inhibitors in EML4-ALK-positive non-small-cell lung cancer cells", British Journal of Cancer, vol. 106, No. 4, Jan. 12, 2012, pp. 763-767, XP055603437, GB ISSN: 0007-0920, DOI: 10.1038/bjc.2011.586.
Uehling Davide et al: "Recent progress on Map kinase pathway inhibitors", Bioorganic & Medicinal Chemistry Letters, Pergamon, Amsterdam, NL, vol. 25, No. 19, Aug. 1, 2015, pp. 4047-4056, XP029264241, ISSN: 0960-894X, DOI: 10.1016/J.BMCL.2015.07.093.

\* cited by examiner

US 10,869,864 B2

SEQUENCE LISTING

<160> NUMBER OF SEQ ID NOS: 5

<210> SEQ ID NO 1
<211> LENGTH: 796
<212> TYPE: PRT
<213> ORGANISM: Homo sapiens

<400> SEQUENCE: 1

```
Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
        35                  40                  45

Arg Cys Thr Arg Asp Gly Ala Leu Asp Ser Leu His His Leu Pro Gly
    50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
    130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
```

```
              210                 215                 220
Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                    245                 250                 255

Asp Leu Asn Arg Lys Asn Val Thr Cys Trp Ala Glu Asn Asp Val Gly
                260                 265                 270

Arg Ala Glu Val Ser Val Gln Val Asn Val Ser Phe Pro Ala Ser Val
                275                 280                 285

Gln Leu His Thr Ala Val Glu Met His His Trp Cys Ile Pro Phe Ser
    290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
                340                 345                 350

His Val Asn Asn Gly Asn Tyr Thr Leu Leu Ala Ala Asn Pro Phe Gly
    355                 360                 365

Gln Ala Ser Ala Ser Ile Met Ala Ala Phe Met Asp Asn Pro Phe Glu
    370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
                420                 425                 430

Ser Thr Leu Leu Leu Val Leu Asn Lys Cys Gly Arg Arg Asn Lys Phe
                435                 440                 445

Gly Ile Asn Arg Pro Ala Val Leu Ala Pro Glu Asp Gly Leu Ala Met
450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
                500                 505                 510

Lys Trp Glu Leu Gly Glu Gly Ala Phe Gly Lys Val Phe Leu Ala Glu
                515                 520                 525

Cys His Asn Leu Leu Pro Glu Gln Asp Lys Met Leu Val Ala Val Lys
                530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
                580                 585                 590

Arg His Gly Asp Leu Asn Arg Phe Leu Arg Ser His Gly Pro Asp Ala
                595                 600                 605

Lys Leu Leu Ala Gly Gly Glu Asp Val Ala Pro Gly Pro Leu Gly Leu
                610                 615                 620

Gly Gln Leu Leu Ala Val Ala Ser Gln Val Ala Ala Gly Met Val Tyr
625                 630                 635                 640
```

```
Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
            675                 680                 685

Leu Pro Ile Arg Trp Met Pro Glu Ser Ile Leu Tyr Arg Lys Phe
        690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
                725                 730                 735

Ile Asp Cys Ile Thr Gln Gly Arg Glu Leu Glu Arg Pro Arg Ala Cys
            740                 745                 750

Pro Pro Glu Val Tyr Ala Ile Met Arg Gly Cys Trp Gln Arg Glu Pro
        755                 760                 765

Gln Gln Arg His Ser Ile Lys Asp Val His Ala Arg Leu Gln Ala Leu
770                 775                 780

Ala Gln Ala Pro Pro Val Tyr Leu Asp Val Leu Gly
785                 790                 795

<210> SEQ ID NO 2
<211> LENGTH: 838
<212> TYPE: PRT
<213> ORGANISM: Homo sapiens

<400> SEQUENCE: 2

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
```

-continued

```
                210                 215                 220
Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Ser Ala Ser Pro
                485                 490                 495

Leu His His Ile Ser Asn Gly Ser Asn Thr Pro Ser Ser Glu Gly
            500                 505                 510

Gly Pro Asp Ala Val Ile Ile Gly Met Thr Lys Ile Pro Val Ile Glu
        515                 520                 525

Asn Pro Gln Tyr Phe Gly Ile Thr Asn Ser Gln Leu Lys Pro Asp Thr
    530                 535                 540

Phe Val Gln His Ile Lys Arg His Asn Ile Val Leu Lys Arg Glu Leu
545                 550                 555                 560

Gly Glu Gly Ala Phe Gly Lys Val Phe Leu Ala Glu Cys Tyr Asn Leu
                565                 570                 575

Cys Pro Glu Gln Asp Lys Ile Leu Val Ala Val Lys Thr Leu Lys Asp
            580                 585                 590

Ala Ser Asp Asn Ala Arg Lys Asp Phe His Arg Glu Ala Glu Leu Leu
        595                 600                 605

Thr Asn Leu Gln His Glu His Ile Val Lys Phe Tyr Gly Val Cys Val
    610                 615                 620

Glu Gly Asp Pro Leu Ile Met Val Phe Glu Tyr Met Lys His Gly Asp
625                 630                 635                 640
```

-continued

Leu Asn Lys Phe Leu Arg Ala His Gly Pro Asp Ala Val Leu Met Ala
            645                 650                 655

Glu Gly Asn Pro Pro Thr Glu Leu Thr Gln Ser Gln Met Leu His Ile
                660                 665                 670

Ala Gln Gln Ile Ala Ala Gly Met Val Tyr Leu Ala Ser Gln His Phe
            675                 680                 685

Val His Arg Asp Leu Ala Thr Arg Asn Cys Leu Val Gly Glu Asn Leu
        690                 695                 700

Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                725                 730                 735

Pro Pro Glu Ser Ile Met Tyr Arg Lys Phe Thr Thr Glu Ser Asp Val
            740                 745                 750

Trp Ser Leu Gly Val Val Leu Trp Glu Ile Phe Thr Tyr Gly Lys Gln
        755                 760                 765

Pro Trp Tyr Gln Leu Ser Asn Asn Glu Val Ile Glu Cys Ile Thr Gln
770                 775                 780

Gly Arg Val Leu Gln Arg Pro Arg Thr Cys Pro Gln Glu Val Tyr Glu
785                 790                 795                 800

Leu Met Leu Gly Cys Trp Gln Arg Glu Pro His Met Arg Lys Asn Ile
                805                 810                 815

Lys Gly Ile His Thr Leu Leu Gln Asn Leu Ala Lys Ala Ser Pro Val
            820                 825                 830

Tyr Leu Asp Ile Leu Gly
        835

<210> SEQ ID NO 3
<211> LENGTH: 839
<212> TYPE: PRT
<213> ORGANISM: Homo sapiens

<400> SEQUENCE: 3

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
                20                  25                  30

Pro Ala Asn Cys Val Cys Ser Lys Thr Glu Ile Asn Cys Arg Arg Pro
            35                  40                  45

Asp Asp Gly Asn Leu Phe Pro Leu Leu Glu Gly Gln Asp Ser Gly Asn
        50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
        130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu

```
                165                 170                 175
Gln Gly Glu Ala Lys Leu Asn Ser Gln Asn Leu Tyr Cys Ile Asn Ala
            180                 185                 190
Asp Gly Ser Gln Leu Pro Leu Phe Arg Met Asn Ile Ser Gln Cys Asp
            195                 200                 205
Leu Pro Glu Ile Ser Val Ser His Val Asn Leu Thr Val Arg Glu Gly
            210                 215                 220
Asp Asn Ala Val Ile Thr Cys Asn Gly Ser Gly Ser Pro Leu Pro Asp
225                 230                 235                 240
Val Asp Trp Ile Val Thr Gly Leu Gln Ser Ile Asn Thr His Gln Thr
            245                 250                 255
Asn Leu Asn Trp Thr Asn Val His Ala Ile Asn Leu Thr Leu Val Asn
            260                 265                 270
Val Thr Ser Glu Asp Asn Gly Phe Thr Leu Thr Cys Ile Ala Glu Asn
            275                 280                 285
Val Val Gly Met Ser Asn Ala Ser Val Ala Leu Thr Val Tyr Tyr Pro
            290                 295                 300
Pro Arg Val Val Ser Leu Glu Glu Pro Glu Leu Arg Leu Glu His Cys
305                 310                 315                 320
Ile Glu Phe Val Val Arg Gly Asn Pro Pro Pro Thr Leu His Trp Leu
            325                 330                 335
His Asn Gly Gln Pro Leu Arg Glu Ser Lys Ile Ile His Val Glu Tyr
            340                 345                 350
Tyr Gln Glu Gly Glu Ile Ser Glu Gly Cys Leu Leu Phe Asn Lys Pro
            355                 360                 365
Thr His Tyr Asn Asn Gly Asn Tyr Thr Leu Ile Ala Lys Asn Pro Leu
            370                 375                 380
Gly Thr Ala Asn Gln Thr Ile Asn Gly His Phe Leu Lys Glu Pro Phe
385                 390                 395                 400
Pro Glu Ser Thr Asp Asn Phe Ile Leu Phe Asp Glu Val Ser Pro Thr
            405                 410                 415
Pro Pro Ile Thr Val Thr His Lys Pro Glu Glu Asp Thr Phe Gly Val
            420                 425                 430
Ser Ile Ala Val Gly Leu Ala Ala Phe Ala Cys Val Leu Leu Val Val
            435                 440                 445
Leu Phe Val Met Ile Asn Lys Tyr Gly Arg Arg Ser Lys Phe Gly Met
            450                 455                 460
Lys Gly Pro Val Ala Val Ile Ser Gly Glu Glu Asp Ser Ala Ser Pro
465                 470                 475                 480
Leu His His Ile Asn His Gly Ile Thr Thr Pro Ser Ser Leu Asp Ala
            485                 490                 495
Gly Pro Asp Thr Val Val Ile Gly Met Thr Arg Ile Pro Val Ile Glu
            500                 505                 510
Asn Pro Gln Tyr Phe Arg Gln Gly His Asn Cys His Lys Pro Asp Thr
            515                 520                 525
Tyr Val Gln His Ile Lys Arg Arg Asp Ile Val Leu Lys Arg Glu Leu
            530                 535                 540
Gly Glu Gly Ala Phe Gly Lys Val Phe Leu Ala Glu Cys Tyr Asn Leu
545                 550                 555                 560
Ser Pro Thr Lys Asp Lys Met Leu Val Ala Val Lys Ala Leu Lys Asp
            565                 570                 575
Pro Thr Leu Ala Ala Arg Lys Asp Phe Gln Arg Glu Ala Glu Leu Leu
            580                 585                 590
```

-continued

Thr Asn Leu Gln His Glu His Ile Val Lys Phe Tyr Gly Val Cys Gly
            595                 600                 605

Asp Gly Asp Pro Leu Ile Met Val Phe Glu Tyr Met Lys His Gly Asp
    610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
        675                 680                 685

Ala Asn Leu Leu Val Lys Ile Gly Asp Phe Gly Met Ser Arg Asp Val
    690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
                725                 730                 735

Met Pro Pro Glu Ser Ile Met Tyr Arg Lys Phe Thr Thr Glu Ser Asp
            740                 745                 750

Val Trp Ser Phe Gly Val Ile Leu Trp Glu Ile Phe Thr Tyr Gly Lys
        755                 760                 765

Gln Pro Trp Phe Gln Leu Ser Asn Thr Glu Val Ile Glu Cys Ile Thr
    770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
                805                 810                 815

Ile Lys Glu Ile Tyr Lys Ile Leu His Ala Leu Gly Lys Ala Thr Pro
            820                 825                 830

Ile Tyr Leu Asp Ile Leu Gly
        835

<210> SEQ ID NO 4
<211> LENGTH: 1620
<212> TYPE: PRT
<213> ORGANISM: Homo sapiens

<400> SEQUENCE: 4

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
    50                  55                  60

Arg Val Tyr Ala Arg Asp Leu Leu Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys

-continued

```
            115                 120                 125
Gly Gly Ser Val Arg Lys Leu Arg Arg Ala Lys Gln Leu Val Leu Glu
130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
                180                 185                 190

Lys Lys Ala Ser Glu Val Gly Arg Glu Gly Arg Leu Ser Ala Ala Ile
                195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
                260                 265                 270

Glu Leu Glu Tyr Ser Pro Pro Leu His Asp Leu Arg Asn Gln Ser Trp
                275                 280                 285

Ser Trp Arg Arg Ile Pro Ser Glu Glu Ala Ser Gln Met Asp Leu Leu
                290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Glu His Cys Thr Leu Ala Val Ser Val His
                340                 345                 350

Arg His Leu Gln Pro Ser Gly Arg Tyr Ile Ala Gln Leu Leu Pro His
                355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
                420                 425                 430

Ser Lys Met Ala Leu Gln Ser Ser Phe Thr Cys Trp Asn Gly Thr Val
    435                 440                 445

Leu Gln Leu Gly Gln Ala Cys Asp Phe His Gln Asp Cys Ala Gln Gly
    450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
                500                 505                 510

Asp His Gln Asp His Ala Leu Leu Leu Ser Thr Thr Asp Val Pro Ala
    515                 520                 525

Ser Glu Ser Ala Thr Val Thr Ser Ala Thr Phe Pro Ala Pro Ile Lys
530                 535                 540
```

```
Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
        595                 600                 605

Leu Gln Met Val Ala Trp Trp Gly Gln Gly Ser Arg Ala Ile Val Ala
    610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
        675                 680                 685

Gly Ala Ser Gly Pro His Gly Pro Thr Gln Ala Gln Cys Asn Asn Ala
    690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
            740                 745                 750

Arg Ser His Gly Val Ser Val Leu Gly Ile Phe Asn Leu Glu Lys Asp
        755                 760                 765

Asp Met Leu Tyr Ile Leu Val Gly Gln Gln Gly Glu Asp Ala Cys Pro
    770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Ala Thr Tyr Val Phe Lys Met Lys Asp Gly
            820                 825                 830

Gly Val Pro Val Pro Leu Ile Ile Ala Ala Gly Gly Gly Gly Arg Ala
        835                 840                 845

Tyr Gly Ala Lys Thr Asp Thr Phe His Pro Glu Arg Leu Glu Asn Asn
    850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
            900                 905                 910

Trp Gly Trp Glu Thr Arg Gly Gly Phe Gly Gly Gly Gly Gly Gly Cys
        915                 920                 925

Ser Ser Gly Gly Gly Gly Gly Tyr Ile Gly Gly Asn Ala Ala Ser
    930                 935                 940

Asn Asn Asp Pro Glu Met Asp Gly Glu Asp Gly Val Ser Phe Ile Ser
945                 950                 955                 960
```

```
Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
            980                 985                 990

Asp Glu Cys His Met Asp Pro Glu Ser His Lys Val Ile Cys Phe Cys
        995                1000                1005

Asp His Gly Thr Val Leu Ala Glu Asp Gly Val Ser Cys Ile Val
    1010                1015                1020

Ser Pro Thr Pro Glu Pro His Leu Pro Leu Ser Leu Ile Leu Ser
    1025                1030                1035

Val Val Thr Ser Ala Leu Val Ala Ala Leu Val Leu Ala Phe Ser
    1040                1045                1050

Gly Ile Met Ile Val Tyr Arg Arg Lys His Gln Glu Leu Gln Ala
    1055                1060                1065

Met Gln Met Glu Leu Gln Ser Pro Glu Tyr Lys Leu Ser Lys Leu
    1070                1075                1080

Arg Thr Ser Thr Ile Met Thr Asp Tyr Asn Pro Asn Tyr Cys Phe
    1085                1090                1095

Ala Gly Lys Thr Ser Ser Ile Ser Asp Leu Lys Glu Val Pro Arg
    1100                1105                1110

Lys Asn Ile Thr Leu Ile Arg Gly Leu Gly His Gly Ala Phe Gly
    1115                1120                1125

Glu Val Tyr Glu Gly Gln Val Ser Gly Met Pro Asn Asp Pro Ser
    1130                1135                1140

Pro Leu Gln Val Ala Val Lys Thr Leu Pro Glu Val Cys Ser Glu
    1145                1150                1155

Gln Asp Glu Leu Asp Phe Leu Met Glu Ala Leu Ile Ile Ser Lys
    1160                1165                1170

Phe Asn His Gln Asn Ile Val Arg Cys Ile Gly Val Ser Leu Gln
    1175                1180                1185

Ser Leu Pro Arg Phe Ile Leu Leu Glu Leu Met Ala Gly Gly Asp
    1190                1195                1200

Leu Lys Ser Phe Leu Arg Glu Thr Arg Pro Arg Pro Ser Gln Pro
    1205                1210                1215

Ser Ser Leu Ala Met Leu Asp Leu Leu His Val Ala Arg Asp Ile
    1220                1225                1230

Ala Cys Gly Cys Gln Tyr Leu Glu Glu Asn His Phe Ile His Arg
    1235                1240                1245

Asp Ile Ala Ala Arg Asn Cys Leu Leu Thr Cys Pro Gly Pro Gly
    1250                1255                1260

Arg Val Ala Lys Ile Gly Asp Phe Gly Met Ala Arg Asp Ile Tyr
    1265                1270                1275

Arg Ala Ser Tyr Tyr Arg Lys Gly Gly Cys Ala Met Leu Pro Val
    1280                1285                1290

Lys Trp Met Pro Pro Glu Ala Phe Met Glu Gly Ile Phe Thr Ser
    1295                1300                1305

Lys Thr Asp Thr Trp Ser Phe Gly Val Leu Leu Trp Glu Ile Phe
    1310                1315                1320

Ser Leu Gly Tyr Met Pro Tyr Pro Ser Lys Ser Asn Gln Glu Val
    1325                1330                1335

Leu Glu Phe Val Thr Ser Gly Gly Arg Met Asp Pro Pro Lys Asn
    1340                1345                1350

Cys Pro Gly Pro Val Tyr Arg Ile Met Thr Gln Cys Trp Gln His
```

```
                1355                1360                1365

Gln Pro Glu Asp Arg Pro Asn Phe Ala Ile Ile Leu Glu Arg Ile
        1370                1375                1380

Glu Tyr Cys Thr Gln Asp Pro Asp Val Ile Asn Thr Ala Leu Pro
    1385                1390                1395

Ile Glu Tyr Gly Pro Leu Val Glu Glu Glu Lys Val Pro Val
1400                1405                1410

Arg Pro Lys Asp Pro Glu Gly Val Pro Pro Leu Leu Val Ser Gln
    1415                1420                1425

Gln Ala Lys Arg Glu Glu Glu Arg Ser Pro Ala Ala Pro Pro Pro
    1430                1435                1440

Leu Pro Thr Thr Ser Ser Gly Lys Ala Ala Lys Lys Pro Thr Ala
    1445                1450                1455

Ala Glu Ile Ser Val Arg Val Pro Arg Gly Pro Ala Val Glu Gly
    1460                1465                1470

Gly His Val Asn Met Ala Phe Ser Gln Ser Asn Pro Pro Ser Glu
    1475                1480                1485

Leu His Lys Val His Gly Ser Arg Asn Lys Pro Thr Ser Leu Trp
    1490                1495                1500

Asn Pro Thr Tyr Gly Ser Trp Phe Thr Glu Lys Pro Thr Lys Lys
    1505                1510                1515

Asn Asn Pro Ile Ala Lys Lys Glu Pro His Asp Arg Gly Asn Leu
    1520                1525                1530

Gly Leu Glu Gly Ser Cys Thr Val Pro Pro Asn Val Ala Thr Gly
    1535                1540                1545

Arg Leu Pro Gly Ala Ser Leu Leu Leu Glu Pro Ser Ser Leu Thr
    1550                1555                1560

Ala Asn Met Lys Glu Val Pro Leu Phe Arg Leu Arg His Phe Pro
    1565                1570                1575

Cys Gly Asn Val Asn Tyr Gly Tyr Gln Gln Gln Gly Leu Pro Leu
    1580                1585                1590

Glu Ala Ala Thr Ala Pro Gly Ala Gly His Tyr Glu Asp Thr Ile
    1595                1600                1605

Leu Lys Ser Lys Asn Ser Met Asn Gln Pro Gly Pro
    1610                1615                1620

<210> SEQ ID NO 5
<211> LENGTH: 2347
<212> TYPE: PRT
<213> ORGANISM: Homo sapiens

<400> SEQUENCE: 5

Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Glu Val Leu
                85                  90                  95
```

-continued

Glu Asn Ala Asp Leu Pro Thr Ala Pro Phe Ala Ser Ser Ile Gly Ser
                100                 105                 110

His Asn Met Thr Leu Arg Trp Lys Ser Ala Asn Phe Ser Gly Val Lys
            115                 120                 125

Tyr Ile Ile Gln Trp Lys Tyr Ala Gln Leu Leu Gly Ser Trp Thr Tyr
        130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
            180                 185                 190

Val Pro Glu Thr Ala Pro Leu Ile Arg Asn Ile Glu Ser Ser Ser Pro
        195                 200                 205

Asp Thr Val Glu Val Ser Trp Asp Pro Pro Gln Phe Pro Gly Gly Pro
210                 215                 220

Ile Leu Gly Tyr Asn Leu Arg Leu Ile Ser Lys Asn Gln Lys Leu Asp
225                 230                 235                 240

Ala Gly Thr Gln Arg Thr Ser Phe Gln Phe Tyr Ser Thr Leu Pro Asn
                245                 250                 255

Thr Ile Tyr Arg Phe Ser Ile Ala Ala Val Asn Glu Val Gly Glu Gly
            260                 265                 270

Pro Glu Ala Glu Ser Ser Ile Thr Thr Ser Ser Ser Ala Val Gln Gln
        275                 280                 285

Glu Glu Gln Trp Leu Phe Leu Ser Arg Lys Thr Ser Leu Arg Lys Arg
        290                 295                 300

Ser Leu Lys His Leu Val Asp Glu Ala His Cys Leu Arg Leu Asp Ala
305                 310                 315                 320

Ile Tyr His Asn Ile Thr Gly Ile Ser Val Asp Val His Gln Gln Ile
                325                 330                 335

Val Tyr Phe Ser Glu Gly Thr Leu Ile Trp Ala Lys Lys Ala Ala Asn
            340                 345                 350

Met Ser Asp Val Ser Asp Leu Arg Ile Phe Tyr Arg Gly Ser Gly Leu
        355                 360                 365

Ile Ser Ser Ile Ser Ile Asp Trp Leu Tyr Gln Arg Met Tyr Phe Ile
        370                 375                 380

Met Asp Glu Leu Val Cys Val Cys Asp Leu Glu Asn Cys Ser Asn Ile
385                 390                 395                 400

Glu Glu Ile Thr Pro Pro Ser Ile Ser Ala Pro Gln Lys Ile Val Ala
                405                 410                 415

Asp Ser Tyr Asn Gly Tyr Val Phe Tyr Leu Leu Arg Asp Gly Ile Tyr
            420                 425                 430

Arg Ala Asp Leu Pro Val Pro Ser Gly Arg Cys Ala Glu Ala Val Arg
        435                 440                 445

Ile Val Glu Ser Cys Thr Leu Lys Asp Phe Ala Ile Lys Pro Gln Ala
        450                 455                 460

Lys Arg Ile Ile Tyr Phe Asn Asp Thr Ala Gln Val Phe Met Ser Thr
465                 470                 475                 480

Phe Leu Asp Gly Ser Ala Ser His Leu Ile Leu Pro Arg Ile Pro Phe
                485                 490                 495

Ala Asp Val Lys Ser Phe Ala Cys Glu Asn Asn Asp Phe Leu Val Thr
            500                 505                 510

Asp Gly Lys Val Ile Phe Gln Gln Asp Ala Leu Ser Phe Asn Glu Phe

```
                515                 520                 525
Ile Val Gly Cys Asp Leu Ser His Ile Glu Glu Phe Gly Phe Gly Asn
        530                 535                 540
Leu Val Ile Phe Gly Ser Ser Gln Leu His Pro Leu Pro Gly Arg
545                 550                 555                 560
Pro Gln Glu Leu Ser Val Leu Phe Gly Ser His Gln Ala Leu Val Gln
                565                 570                 575
Trp Lys Pro Pro Ala Leu Ala Ile Gly Ala Asn Val Ile Leu Ile Ser
            580                 585                 590
Asp Ile Ile Glu Leu Phe Glu Leu Gly Pro Ser Ala Trp Gln Asn Trp
                595                 600                 605
Thr Tyr Glu Val Lys Val Ser Thr Gln Asp Pro Pro Glu Val Thr His
            610                 615                 620
Ile Phe Leu Asn Ile Ser Gly Thr Met Leu Asn Val Pro Glu Leu Gln
625                 630                 635                 640
Ser Ala Met Lys Tyr Lys Val Ser Val Arg Ala Ser Ser Pro Lys Arg
                645                 650                 655
Pro Gly Pro Trp Ser Glu Pro Ser Val Gly Thr Thr Leu Val Pro Ala
            660                 665                 670
Ser Glu Pro Pro Phe Ile Met Ala Val Lys Glu Asp Gly Leu Trp Ser
        675                 680                 685
Lys Pro Leu Asn Ser Phe Gly Pro Gly Glu Phe Leu Ser Ser Asp Ile
        690                 695                 700
Gly Asn Val Ser Asp Met Asp Trp Tyr Asn Asn Ser Leu Tyr Tyr Ser
705                 710                 715                 720
Asp Thr Lys Gly Asp Val Phe Val Trp Leu Leu Asn Gly Thr Asp Ile
                725                 730                 735
Ser Glu Asn Tyr His Leu Pro Ser Ile Ala Gly Ala Gly Ala Leu Ala
            740                 745                 750
Phe Glu Trp Leu Gly His Phe Leu Tyr Trp Ala Gly Lys Thr Tyr Val
        755                 760                 765
Ile Gln Arg Gln Ser Val Leu Thr Gly His Thr Asp Ile Val Thr His
        770                 775                 780
Val Lys Leu Leu Val Asn Asp Met Val Val Asp Ser Val Gly Gly Tyr
785                 790                 795                 800
Leu Tyr Trp Thr Thr Leu Tyr Ser Val Glu Ser Thr Arg Leu Asn Gly
                805                 810                 815
Glu Ser Ser Leu Val Leu Gln Thr Gln Pro Trp Phe Ser Gly Lys Lys
            820                 825                 830
Val Ile Ala Leu Thr Leu Asp Leu Ser Asp Gly Leu Leu Tyr Trp Leu
        835                 840                 845
Val Gln Asp Ser Gln Cys Ile His Leu Tyr Thr Ala Val Leu Arg Gly
        850                 855                 860
Gln Ser Thr Gly Asp Thr Thr Ile Thr Glu Phe Ala Ala Trp Ser Thr
865                 870                 875                 880
Ser Glu Ile Ser Gln Asn Ala Leu Met Tyr Tyr Ser Gly Arg Leu Phe
                885                 890                 895
Trp Ile Asn Gly Phe Arg Ile Ile Thr Thr Gln Glu Ile Gly Gln Lys
            900                 905                 910
Thr Ser Val Ser Val Leu Glu Pro Ala Arg Phe Asn Gln Phe Thr Ile
        915                 920                 925
Ile Gln Thr Ser Leu Lys Pro Leu Pro Gly Asn Phe Ser Phe Thr Pro
        930                 935                 940
```

-continued

```
Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
                965                 970                 975

Trp Gly Val Val Phe Tyr Ser Val Glu Phe Ser Ala His Ser Lys Phe
            980                 985                 990

Leu Ala Ser Glu Gln His Ser Leu Pro Val Phe Thr Val Glu Gly Leu
        995                1000                1005

Glu Pro Tyr Ala Leu Phe Asn Leu Ser Val Thr Pro Tyr Thr Tyr
    1010                1015                1020

Trp Gly Lys Gly Pro Lys Thr Ser Leu Ser Leu Arg Ala Pro Glu
    1025                1030                1035

Thr Val Pro Ser Ala Pro Glu Asn Pro Arg Ile Phe Ile Leu Pro
    1040                1045                1050

Ser Gly Lys Cys Cys Asn Lys Asn Glu Val Val Glu Phe Arg
    1055                1060                1065

Trp Asn Lys Pro Lys His Glu Asn Gly Val Leu Thr Lys Phe Glu
    1070                1075                1080

Ile Phe Tyr Asn Ile Ser Asn Gln Ser Ile Thr Asn Lys Thr Cys
    1085                1090                1095

Glu Asp Trp Ile Ala Val Asn Val Thr Pro Ser Val Met Ser Phe
    1100                1105                1110

Gln Leu Glu Gly Met Ser Pro Arg Cys Phe Ile Ala Phe Gln Val
    1115                1120                1125

Arg Ala Phe Thr Ser Lys Gly Pro Gly Pro Tyr Ala Asp Val Val
    1130                1135                1140

Lys Ser Thr Thr Ser Glu Ile Asn Pro Phe Pro His Leu Ile Thr
    1145                1150                1155

Leu Leu Gly Asn Lys Ile Val Phe Leu Asp Met Asp Gln Asn Gln
    1160                1165                1170

Val Val Trp Thr Phe Ser Ala Glu Arg Val Ile Ser Ala Val Cys
    1175                1180                1185

Tyr Thr Ala Asp Asn Glu Met Gly Tyr Tyr Ala Glu Gly Asp Ser
    1190                1195                1200

Leu Phe Leu Leu His Leu His Asn Arg Ser Ser Ser Glu Leu Phe
    1205                1210                1215

Gln Asp Ser Leu Val Phe Asp Ile Thr Val Ile Thr Ile Asp Trp
    1220                1225                1230

Ile Ser Arg His Leu Tyr Phe Ala Leu Lys Glu Ser Gln Asn Gly
    1235                1240                1245

Met Gln Val Phe Asp Val Asp Leu Glu His Lys Val Lys Tyr Pro
    1250                1255                1260

Arg Glu Val Lys Ile His Asn Arg Asn Ser Thr Ile Ile Ser Phe
    1265                1270                1275

Ser Val Tyr Pro Leu Leu Ser Arg Leu Tyr Trp Thr Glu Val Ser
    1280                1285                1290

Asn Phe Gly Tyr Gln Met Phe Tyr Tyr Ser Ile Ile Ser His Thr
    1295                1300                1305

Leu His Arg Ile Leu Gln Pro Thr Ala Thr Asn Gln Gln Asn Lys
    1310                1315                1320

Arg Asn Gln Cys Ser Cys Asn Val Thr Glu Phe Glu Leu Ser Gly
    1325                1330                1335
```

```
Ala Met Ala Ile Asp Thr Ser Asn Leu Glu Lys Pro Leu Ile Tyr
    1340            1345                1350

Phe Ala Lys Ala Gln Glu Ile Trp Ala Met Asp Leu Glu Gly Cys
    1355            1360                1365

Gln Cys Trp Arg Val Ile Thr Val Pro Ala Met Leu Ala Gly Lys
    1370            1375                1380

Thr Leu Val Ser Leu Thr Val Asp Gly Asp Leu Ile Tyr Trp Ile
    1385            1390                1395

Ile Thr Ala Lys Asp Ser Thr Gln Ile Tyr Gln Ala Lys Lys Gly
    1400            1405                1410

Asn Gly Ala Ile Val Ser Gln Val Lys Ala Leu Arg Ser Arg His
    1415            1420                1425

Ile Leu Ala Tyr Ser Ser Val Met Gln Pro Phe Pro Asp Lys Ala
    1430            1435                1440

Phe Leu Ser Leu Ala Ser Asp Thr Val Glu Pro Thr Ile Leu Asn
    1445            1450                1455

Ala Thr Asn Thr Ser Leu Thr Ile Arg Leu Pro Leu Ala Lys Thr
    1460            1465                1470

Asn Leu Thr Trp Tyr Gly Ile Thr Ser Pro Thr Pro Thr Tyr Leu
    1475            1480                1485

Val Tyr Tyr Ala Glu Val Asn Asp Arg Lys Asn Ser Ser Asp Leu
    1490            1495                1500

Lys Tyr Arg Ile Leu Glu Phe Gln Asp Ser Ile Ala Leu Ile Glu
    1505            1510                1515

Asp Leu Gln Pro Phe Ser Thr Tyr Met Ile Gln Ile Ala Val Lys
    1520            1525                1530

Asn Tyr Tyr Ser Asp Pro Leu Glu His Leu Pro Pro Gly Lys Glu
    1535            1540                1545

Ile Trp Gly Lys Thr Lys Asn Gly Val Pro Glu Ala Val Gln Leu
    1550            1555                1560

Ile Asn Thr Thr Val Arg Ser Asp Thr Ser Leu Ile Ile Ser Trp
    1565            1570                1575

Arg Glu Ser His Lys Pro Asn Gly Pro Lys Glu Ser Val Arg Tyr
    1580            1585                1590

Gln Leu Ala Ile Ser His Leu Ala Leu Ile Pro Glu Thr Pro Leu
    1595            1600                1605

Arg Gln Ser Glu Phe Pro Asn Gly Arg Leu Thr Leu Leu Val Thr
    1610            1615                1620

Arg Leu Ser Gly Gly Asn Ile Tyr Val Leu Lys Val Leu Ala Cys
    1625            1630                1635

His Ser Glu Glu Met Trp Cys Thr Glu Ser His Pro Val Thr Val
    1640            1645                1650

Glu Met Phe Asn Thr Pro Glu Lys Pro Tyr Ser Leu Val Pro Glu
    1655            1660                1665

Asn Thr Ser Leu Gln Phe Asn Trp Lys Ala Pro Leu Asn Val Asn
    1670            1675                1680

Leu Ile Arg Phe Trp Val Glu Leu Gln Lys Trp Lys Tyr Asn Glu
    1685            1690                1695

Phe Tyr His Val Lys Thr Ser Cys Ser Gln Gly Pro Ala Tyr Val
    1700            1705                1710

Cys Asn Ile Thr Asn Leu Gln Pro Tyr Thr Ser Tyr Asn Val Arg
    1715            1720                1725

Val Val Val Val Tyr Lys Thr Gly Glu Asn Ser Thr Ser Leu Pro
```

-continued

```
            1730                1735                1740
Glu Ser Phe Lys Thr Lys Ala Gly Val Pro Asn Lys Pro Gly Ile
        1745                1750                1755
Pro Lys Leu Leu Glu Gly Ser Lys Asn Ser Ile Gln Trp Glu Lys
        1760                1765                1770
Ala Glu Asp Asn Gly Cys Arg Ile Thr Tyr Tyr Ile Leu Glu Ile
        1775                1780                1785
Arg Lys Ser Thr Ser Asn Asn Leu Gln Asn Gln Asn Leu Arg Trp
        1790                1795                1800
Lys Met Thr Phe Asn Gly Ser Cys Ser Ser Val Cys Thr Trp Lys
        1805                1810                1815
Ser Lys Asn Leu Lys Gly Ile Phe Gln Phe Arg Val Val Ala Ala
        1820                1825                1830
Asn Asn Leu Gly Phe Gly Glu Tyr Ser Gly Ile Ser Glu Asn Ile
        1835                1840                1845
Ile Leu Val Gly Asp Asp Phe Trp Ile Pro Glu Thr Ser Phe Ile
        1850                1855                1860
Leu Thr Ile Ile Val Gly Ile Phe Leu Val Val Thr Ile Pro Leu
        1865                1870                1875
Thr Phe Val Trp His Arg Arg Leu Lys Asn Gln Lys Ser Ala Lys
        1880                1885                1890
Glu Gly Val Thr Val Leu Ile Asn Glu Asp Lys Glu Leu Ala Glu
        1895                1900                1905
Leu Arg Gly Leu Ala Ala Gly Val Gly Leu Ala Asn Ala Cys Tyr
        1910                1915                1920
Ala Ile His Thr Leu Pro Thr Gln Glu Glu Ile Glu Asn Leu Pro
        1925                1930                1935
Ala Phe Pro Arg Glu Lys Leu Thr Leu Arg Leu Leu Leu Gly Ser
        1940                1945                1950
Gly Ala Phe Gly Glu Val Tyr Glu Gly Thr Ala Val Asp Ile Leu
        1955                1960                1965
Gly Val Gly Ser Gly Glu Ile Lys Val Ala Val Lys Thr Leu Lys
        1970                1975                1980
Lys Gly Ser Thr Asp Gln Glu Lys Ile Glu Phe Leu Lys Glu Ala
        1985                1990                1995
His Leu Met Ser Lys Phe Asn His Pro Asn Ile Leu Lys Gln Leu
        2000                2005                2010
Gly Val Cys Leu Leu Asn Glu Pro Gln Tyr Ile Ile Leu Glu Leu
        2015                2020                2025
Met Glu Gly Gly Asp Leu Leu Thr Tyr Leu Arg Lys Ala Arg Met
        2030                2035                2040
Ala Thr Phe Tyr Gly Pro Leu Leu Thr Leu Val Asp Leu Val Asp
        2045                2050                2055
Leu Cys Val Asp Ile Ser Lys Gly Cys Val Tyr Leu Glu Arg Met
        2060                2065                2070
His Phe Ile His Arg Asp Leu Ala Ala Arg Asn Cys Leu Val Ser
        2075                2080                2085
Val Lys Asp Tyr Thr Ser Pro Arg Ile Val Lys Ile Gly Asp Phe
        2090                2095                2100
Gly Leu Ala Arg Asp Ile Tyr Lys Asn Asp Tyr Tyr Arg Lys Arg
        2105                2110                2115
Gly Glu Gly Leu Leu Pro Val Arg Trp Met Ala Pro Glu Ser Leu
        2120                2125                2130
```

```
Met Asp Gly Ile Phe Thr Thr     Gln Ser Asp Val Trp     Ser Phe Gly
    2135                2140                2145

Ile Leu Ile Trp Glu Ile Leu     Thr Leu Gly His Gln     Pro Tyr Pro
    2150                2155                2160

Ala His Ser Asn Leu Asp Val     Leu Asn Tyr Val Gln     Thr Gly Gly
    2165                2170                2175

Arg Leu Glu Pro Pro Arg Asn     Cys Pro Asp Asp Leu     Trp Asn Leu
    2180                2185                2190

Met Thr Gln Cys Trp Ala Gln     Glu Pro Asp Gln Arg     Pro Thr Phe
    2195                2200                2205

His Arg Ile Gln Asp Gln Leu     Gln Leu Phe Arg Asn     Phe Phe Leu
    2210                2215                2220

Asn Ser Ile Tyr Lys Ser Arg     Asp Glu Ala Asn Asn     Ser Gly Val
    2225                2230                2235

Ile Asn Glu Ser Phe Glu Gly     Glu Asp Gly Asp Val     Ile Cys Leu
    2240                2245                2250

Asn Ser Asp Asp Ile Met Pro     Val Ala Leu Met Glu     Thr Lys Asn
    2255                2260                2265

Arg Glu Gly Leu Asn Tyr Met     Val Leu Ala Thr Glu     Cys Gly Gln
    2270                2275                2280

Gly Glu Glu Lys Ser Glu Gly     Pro Leu Gly Ser Gln     Glu Ser Glu
    2285                2290                2295

Ser Cys Gly Leu Arg Lys Glu     Glu Lys Glu Pro His     Ala Asp Lys
    2300                2305                2310

Asp Phe Cys Gln Glu Lys Gln     Val Ala Tyr Cys Pro     Ser Gly Lys
    2315                2320                2325

Pro Glu Gly Leu Asn Tyr Ala     Cys Leu Thr His Ser     Gly Tyr Gly
    2330                2335                2340

Asp Gly Ser Asp
    2345
```

COMBINATIONS FOR THE TREATMENT OF CANCER

CROSS-REFERENCE TO RELATED APPLICATIONS

This application is a U.S. national stage application of International Patent Application No. PCT/US2016/066919, filed Dec. 15, 2016; which claims the benefit of priority to U.S. Provisional Application No. 62/269,805, filed Dec. 18, 2015, and U.S. Provisional Application No. 62/428,498, filed Nov. 30, 2016, each of which are hereby incorporated by reference in their entirety.

SEQUENCE LISTING

The instant application contains a Sequence Listing which has been submitted electronically in ASCII format and is hereby incorporated by reference in its entirety. Said ASCII copy, originally filed in International Patent Application No. PCT/US2016/066919 on Jan. 26, 2017, is named 109885-0402_SL.txt and is 56,3744 bytes in size.

FIELD

The present disclosure relates to methods of treating cancer in a patient, wherein the patient is known to possess at least one molecular alteration in ALK, ROS1, NTRK1, NTRK2, NTRK3, TrkA, TrkB, or TrkC, or a combination thereof, comprising administering to the patient a combination comprising a therapeutically effective amount of a first agent and a therapeutically effective amount of a second agent, wherein the first agent is an inhibitor or ALK, ROS1, TrkA, TrkB, or TrkC, or a combination thereof, and the second agent is selected from a MEK inhibitor and an ERK inhibitor.

BACKGROUND

The malfunctioning of protein kinases (PKs) is the hallmark of numerous diseases. A large share of the oncogenes and proto-oncogenes involved in human cancers encode for PKs. For a general reference to PKs malfunctioning or deregulation see, for instance, Current Opinion in Chemical Biology 1999, 3:459-465, which is incorporated by reference herein in its entirety.

Anaplastic lymphoma kinase (ALK) is a tyrosine kinase receptor belonging to the insulin receptor subfamily of RTKs: the ALK gene is located on chromosome 2 and is expressed mainly in neuronal cells, especially during development. Many data from the literature have demonstrated that the ALK fusion proteins have strong oncogenic potentials.

ROS1 belongs to the insulin-receptor superfamily. Like other tyrosine kinase receptor molecules, it plays a role in relaying growth signals from the environment outside the cell into the cell's nucleus. It is 1 of 2 orphan receptor tyrosine kinase family members with no known binding ligand. Genetic changes in ROS1, such as gene rearrangements, mutations, or copy number increases, create oncogenes, which can lead to cancer. ROS1 was discovered in NSCLC patients in the form of a fusion protein (6 different partners for ROS1) and is found in approximately 2% of patients with NSCLC. Two other ROS1 gene rearrangements have been detected in a variety of other cancers, including glioblastoma multiforme, cholangiocarcinoma, ovarian cancer, gastric adenocarcinoma, colorectal cancer, inflammatory myofibroblastic tumor, angiosarcoma, and epitheloid hemangioendothelioma.

Trks are the high affinity receptor tyrosine kinases activated by a group of soluble growth factors called neurotrophins (NT). The Trk receptor family has three members—TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trks are widely expressed in neuronal tissue and are implicated in the maintenance, signaling and survival of neuronal cells (Patapoutian et al., Current Opinion in Neurobiology, 2001, 11, 272-280, incorporated by reference in its entirety herein). NTRK1 encodes the TrkA receptor tyrosine kinase. TrkA activates the PI3K/AKT, PKC and ERK1/2 pathways which promote cell growth and survival.

Recent literature has shown that overexpression, activation, amplification and/or mutation of Trks are associated with many cancers including neuroblastoma (Brodeur, G. M., Nat. Rev. Cancer 2003, 3, 203-216, incorporated by reference in its entirety herein), ovarian cancer (Davidson. B., et al., Clin. Cancer Res. 2003, 9, 2248-2259, incorporated by reference in its entirety herein), breast cancer (Kruettgen et al., Brain Pathology 2006, 16: 304-310, incorporated by reference in its entirety herein), prostate cancer (Dionne et al., Clin. Cancer Res. 1998, 4(8): 1887-1898, incorporated by reference in its entirety herein), pancreatic cancer (Dang et al., Journal of Gastroenterology and Hepatology 2006, 21(5): 850-858, incorporated by reference in its entirety herein), multiple myeloma (Hu et al., Cancer Genetics and Cytogenetics 2007, 178: 1-10, incorporated by reference in its entirety herein), astrocytoma and medulloblastoma (Kruettgen et al., Brain Pathology 2006, 16: 304-310, incorporated by reference in its entirety herein) glioma (Hansen et al., Journal of Neurochemistry 2007, 103: 259-275, incorporated by reference in its entirety herein), melanoma (Truzzi et al., Journal of Investigative Dermatology 2008, 128(8): 2031-2040, incorporated by reference in its entirety herein), thyroid carcinoma (Brzezianska et al., Neuroendocrinology Letters 2007, 28(3), 221-229, incorporated by reference in its entirety herein), lung adenocarcinoma (Perez-Pinera et al., Molecular and Cellular Biochemistry 2007, 295(1&2), 19-26, incorporated by reference in its entirety herein), large cell neuroendocrine tumors (Marchetti et al., Human Mutation 2008, 29(5), 609-616, incorporated by reference in its entirety herein), and colorectal cancer (Bardelli, A., Science 2003, 300, 949, incorporated by reference in its entirety herein). In preclinical models of cancer, Trk inhibitors are efficacious in both inhibiting tumor growth and stopping tumor metastasis. In particular, non-selective small molecule inhibitors of Trk A, B and C and Trk/Fc chimeras were efficacious in both inhibiting tumor growth and stopping tumor metastasis (Nakagawara, A. Cancer Letters 2001, 169:107-114; Meyer et al., Leukemia 2007, 1-10; Pierottia and Greco, Cancer Letters 2006, 232: 90-98; Eric Adriaenssens et al., Cancer Res 2008, 68:(2) 346-351; Truzzi et al., Journal of Investigative Dermatology 2008, 128(8): 2031-2040, each of which is incorporated by reference in its entirety herein). Therefore, an inhibitor of the Trk family of kinases is expected to have utility in the treatment of cancer.

SUMMARY

In one aspect, disclosed herein are methods of treating cancer in a patient in need thereof, the method comprising administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof; and the second agent is a MEK inhibitor or an ERK inhibitor.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is an ALK inhibitor; the second agent is a MEK inhibitor or an ERK inhibitor; and the patient has at least one genetic alteration in ALK.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is an ALK inhibitor; the second agent is a MEK inhibitor or an ERK inhibitor; and the patient has at least one mutation in the ALK receptor tyrosine kinase polypeptide. In some embodiments, the at least one mutation in the ALK receptor tyrosine kinase polypeptide is at a position corresponding to amino acid residue G1202 or G1269 of the ALK polypeptide set forth in SEQ ID NO: 4. In some embodiments, the at least one mutation in the ALK receptor tyrosine kinase polypeptide is at the position corresponding to amino acid residue G1202 of the ALK polypeptide set forth in SEQ ID NO: 4. In some embodiments, the at least one mutation in the ALK receptor tyrosine kinase polypeptide is at the position corresponding to amino acid residue G1269 of the ALK polypeptide set forth in SEQ ID NO: 4.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a ROS1 inhibitor; the second agent is a MEK inhibitor or an ERK inhibitor; and the patient has at least one genetic alteration in ROS1.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a ROS1 inhibitor; the second agent is a MEK inhibitor or an ERK inhibitor; and the patient has at least one mutation in the ROS1 receptor tyrosine kinase polypeptide. In some embodiments, the at least one mutation in the ROS1 receptor tyrosine kinase polypeptide is at a position corresponding to amino acid residue G2032 or G2101 of the ROS1 polypeptide set forth in SEQ ID NO: 5. In some embodiments, the at least one mutation in the ROS1 receptor tyrosine kinase polypeptide is at the position corresponding to amino acid residue G2032 of the ROS1 polypeptide set forth in SEQ ID NO: 5. In some embodiments, the at least one mutation in the ROS1 receptor tyrosine kinase polypeptide is at the position corresponding to amino acid residue G2101 of the ROS1 polypeptide set forth in SEQ ID NO: 5.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a TrkA inhibitor; the second agent is a MEK inhibitor or an ERK inhibitor; and the patient has at least one genetic alteration in NTRK1.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a TrkA inhibitor; the second agent is a MEK inhibitor or an ERK inhibitor; and the patient has at least one mutation in the TrkA receptor tyrosine kinase polypeptide. In some embodiments, the at least one mutation in the TrkA receptor tyrosine kinase polypeptide is at a position corresponding to amino acid residue G595 or G667 of the TrkA polypeptide set forth in SEQ ID NO: 1. In some embodiments, the at least one mutation in the TrkA receptor tyrosine kinase polypeptide is at the position corresponding to amino acid residue G595 of the TrkA polypeptide set forth in SEQ ID NO: 1. In some embodiments, the at least one mutation in the TrkA receptor tyrosine kinase polypeptide is Glu-to-Arg substitution (G595R). In some embodiments, the at least one mutation in the TrkA receptor tyrosine kinase polypeptide is at the position corresponding to amino acid residue G667 of the TrkA polypeptide set forth in SEQ ID NO: 1. In some embodiments, the at least one mutation in the TrkA receptor tyrosine kinase polypeptide is Glu-to-Cys substitution (G667C).

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a TrkB inhibitor; the second agent is a MEK inhibitor or an ERK inhibitor; and the patient has at least one genetic alteration in NTRK2.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a TrkB inhibitor; the second agent is a MEK inhibitor or an ERK inhibitor; and the patient has at least one mutation in the TrkB receptor tyrosine kinase polypeptide. In some embodiments, the at least one mutation in the TrkB receptor tyrosine kinase polypeptide is at a position corresponding to amino acid residue G639 or G709 of the TrkB polypeptide set forth in SEQ ID NO: 2. In some embodiments, the at least one mutation in the TrkB receptor tyrosine kinase polypeptide is at the position corresponding to amino acid residue G639 of the TrkB polypeptide set forth in SEQ ID NO: 2. In some embodiments, the at least one mutation in the TrkB receptor tyrosine kinase polypeptide is Glu-to-Arg substitution (G639R). In some embodiments, the at least one mutation in the TrkB receptor tyrosine kinase polypeptide is at the position corresponding to amino acid residue G709 of the TrkB polypeptide set forth in SEQ ID NO: 2. In some embodiments, the at least one mutation in the TrkB receptor tyrosine kinase polypeptide is Glu-to-Cys substitution (G709C).

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a TrkC inhibitor; the second agent is a MEK inhibitor or an ERK inhibitor; and the patient has at least one genetic alteration in NTRK3.

In another aspect, disclosed herein are methods of treating cancer in a patient in need thereof, the method comprising administering to the patient a combination comprising a therapeutically effective amount of a first agent and a therapeutically effective amount of a second agent, wherein the first agent is a TrkC inhibitor; the second agent is a MEK inhibitor or an ERK inhibitor; and the patient has at least one mutation in the TrkC receptor tyrosine kinase polypeptide. In some embodiments, the at least one mutation in the TrkC receptor tyrosine kinase polypeptide is at a position corresponding to amino acid residue G623 or G696 of the TrkC polypeptide set forth in SEQ ID NO: 3. In some embodiments, the at least one mutation in the TrkC receptor tyrosine kinase polypeptide is at the position corresponding to amino acid residue G623 of the TrkC polypeptide set forth in SEQ ID NO: 3. In some embodiments, the at least one mutation in the TrkC receptor tyrosine kinase polypeptide is Glu-to-Arg substitution (G623R). In some embodiments, the at least one mutation in the TrkC receptor tyrosine kinase polypeptide is at the position corresponding to amino acid residue G696 of the TrkC polypeptide set forth in SEQ ID NO: 3. In some embodiments, the at least one mutation in the TrkC receptor tyrosine kinase polypeptide is Glu-to-Cys substitution (G696C).

In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments, the second agent is a MEK inhibitor. In some embodiments, the MEK inhibitor is an inhibitor of MEK1, MEK2, or a combination thereof. In some embodiments, the MEK inhibitor is selected from the group consisting of PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the MEK inhibitor is PD0325901. In some embodiments, the MEK inhibitor is selumetinib. In some embodiments, the MEK inhibitor is cobimetinib. In some embodiments, the MEK inhibitor is refametinib. In some embodiments, the MEK inhibitor is trametinib. In some embodiments, the MEK inhibitor is pimasertib. In some embodiments, the MEK inhibitor is binimetinib. In some embodiments, the MEK inhibitor is AZD8330. In some embodiments, the MEK inhibitor is RO4987655. In some embodiments, the MEK inhibitor is RO5126766. In some embodiments, the MEK inhibitor is WX-554. In some embodiments, the MEK inhibitor is E-6201. In some embodiments, the MEK inhibitor is GDC-0623. In some embodiments, the MEK inhibitor is TAK-733. In some embodiments, the MEK inhibitor is RG-7304. In some embodiments, the MEK inhibitor is CKBP-002. In some embodiments, the MEK inhibitor is RDEA-436. In some embodiments, the MEK inhibitor is sorafenib. In some embodiments, the MEK inhibitor is PD-184352. In some embodiments, the MEK inhibitor is GSK-2091976A. In some embodiments, the MEK inhibitor is AS-703988.

In some embodiments, the second agent is an ERK inhibitor. In some embodiments, the ERK inhibitor is an inhibitor of ERK1, ERK2, or a combination thereof. In some embodiments, the ERK inhibitor is selected from the group consisting of TG-02, MK-8353, ulixertinib, HE-3235, AEZS-134, AEZS-136, and IDN-5491. In some embodiments, the ERK inhibitor is TG-02. In some embodiments, the ERK inhibitor is MK-8353. In some embodiments, the ERK inhibitor is ulixertinib. In some embodiments, the ERK inhibitor is HE-3235. In some embodiments, the ERK inhibitor is AEZS-134. In some embodiments, the ERK inhibitor is AEZS-136. In some embodiments, the ERK inhibitor is IDN-5491.

In some embodiments, the cancer is selected from non-small cell lung cancer, papillary thyroid cancer, neuroblastoma, pancreatic cancer, melanoma, and colorectal cancer. In some embodiments, the cancer is non-small cell lung cancer. In some embodiments, the cancer is papillary thyroid cancer. In some embodiments, the cancer is neuroblastoma. In some embodiments, the cancer is pancreatic cancer. In some embodiments, the cancer is melanoma. In some embodiments, the cancer is colorectal cancer.

In some embodiments, the combination is a pharmaceutical composition comprising the therapeutically effective amount of the first agent, the therapeutically effective amount of the second agent, and at least one pharmaceutically acceptable carrier.

In some embodiments, the combination is concurrent administration of a first pharmaceutical composition comprising the therapeutically effective amount of the first agent and a second pharmaceutical composition comprising the therapeutically effective amount of the second agent.

In some embodiments, the combination is sequential administration of a first pharmaceutical composition comprising the therapeutically effective amount of the first agent and a second pharmaceutical composition comprising the therapeutically effective amount of the second agent.

DETAILED DESCRIPTION

Figure 1:
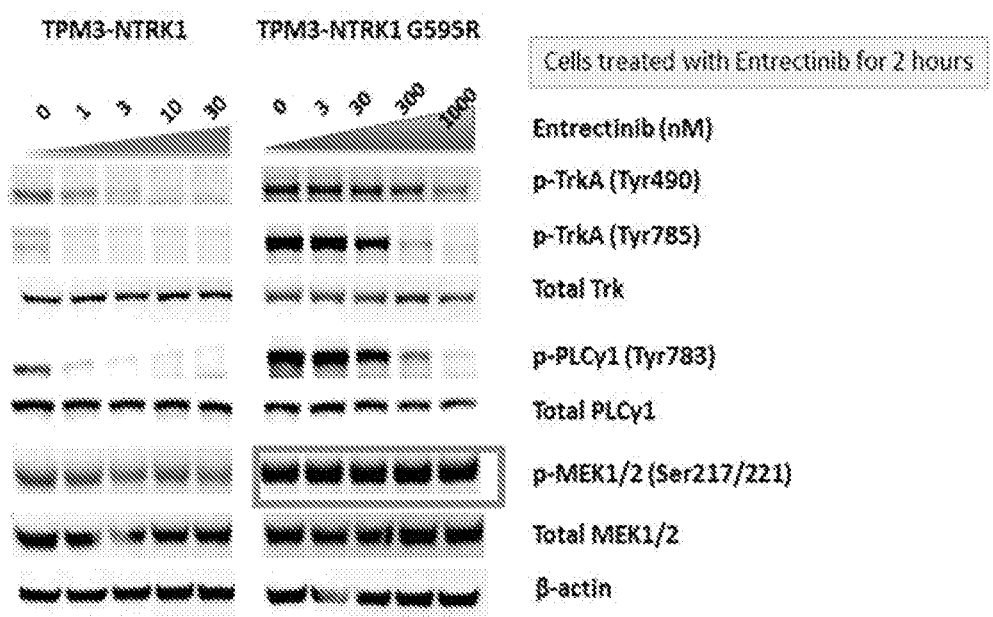
FIG. 1 is a Western Blot analysis from Example 9 demonstrating that p-MEK1/2 (Ser217/221) and total MEK1/2 are upregulated in the Ba/F3 cells expressing TPM3-TrkA-G595R versus Ba/F3 cells expressing wild-type TPM3-TrkA.

The term "N-[5-(3,5-difluorobenzyl)-1H-indazol-3-yl]-4-(4-methyl-piperazin-1-yl)-2-(tetrahydro-pyran-4-ylamino)-benzamide," as used herein, means the compound having the chemical structure,

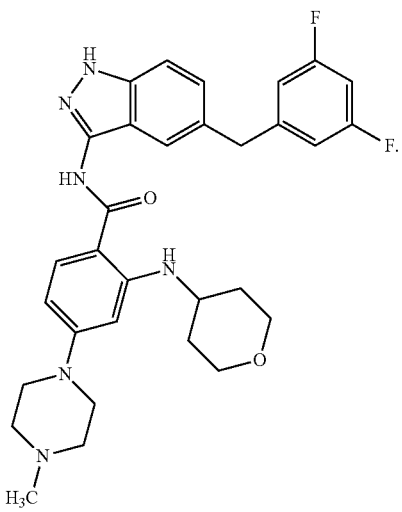 [SMILES: CN1CCN(c2ccc(C(=O)Nc3n[nH]c4ccc(Cc5cc(F)cc(F)c5)cc34)c(NC3CCOCC3)c2)CC1]

N-[5-(3,5-Difluorobenzyl)-1H-indazol-3-yl]-4-(4-methyl-piperazin-1-yl)-2-(tetrahydro-pyran-4-ylamino)-benzamide may be prepared as described in U.S. Pat. No. 8,299,057, the disclosure of which is hereby incorporated by reference in its entirety. N-[5-(3,5-difluorobenzyl)-1H-indazol-3-yl]-4-(4-methyl-piperazin-1-yl)-2-(tetrahydro-pyran-4-ylamino)-benzamide is associated with CAS Registry Number 1108743-60-7. The N-[5-(3,5-difluorobenzyl)-1H-indazol-3-yl]-4-(4-methyl-piperazin-1-yl)-2-(tetrahydro-pyran-4-ylamino)-benzamide compound may also be described as "entrectinib" and/or "RXDX-101."

The singular form "a," "an," and "the" include plural references unless the context clearly dictates otherwise. For example, the term "a cell" includes one or more cells, including mixtures thereof "A and/or B" is used herein to include all of the following alternatives: "A," "B," "A or B," and "A and B".

The term "about," as used herein, means either within plus or minus 10% of the provided value, or rounded to the nearest significant figure, in all cases inclusive of the provided value. Where ranges are provided, they are inclusive of the boundary values.

The term "acidulant," as used herein, means a chemical compound that is acidic in nature. As used herein, the term "organic acidulant" means an acidulant the chemical composition of which contains carbon. As used herein, the term "inorganic acidulant" means an acidulant the composition of which does not contain carbon.

The terms "administration" and "administering," as used herein, refer to the delivery of a bioactive composition or formulation by an administration route including, but not limited to, intravenous, intra-arterial, intramuscular, intraperitoneal, subcutaneous, intramuscular, topically, or combinations thereof.

The term "AUC," as used herein, means the area under the curve of a plot of the concentration of a compound in the plasma of a patient versus time.

The terms "anaplastic lymphoma kinase" and "ALK," as used herein, mean the ALK tyrosine kinase receptor or CD246 (cluster of differentiation 246), which is an enzyme that in humans is encoded by the ALK gene and also has the UniProt identifier ALK_HUMAN.

The term "AZD8330," as used herein, means the compound having the chemical structure,

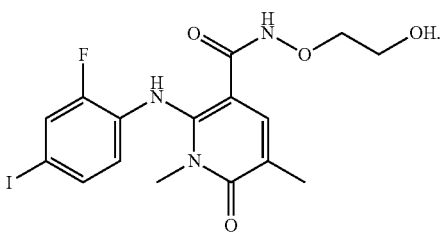 [SMILES: Cc1cc(C(=O)NOCCO)c(Nc2ccc(I)cc2F)n(C)c1=O]

Alternative names for AZD8330 include AZD-8330 and 2-(2-fluoro-4-iodophenylamino)-N-(2-hydroxyethoxy)-1,5-dimethyl-6-oxo-1,6-dihydropyridine-3-carboxamide. AZD8330 is associated with CAS Registry Number 869357-68-6.

The term "betaine hydrochloride," as used herein, means a compound having CAS Registry Number 590-46-5 and the common names 1-carboxy-N,N,N-trimethylmethanaminium chloride and (carboxymethyl)trimethylammonium hydrochloride.

The term "binimetinib," as used herein, means the compound having the chemical structure,

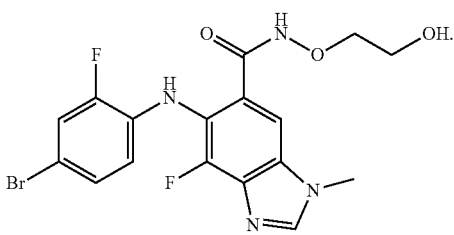 [SMILES: Cn1cnc2c(F)c(Nc3ccc(Br)cc3F)c(C(=O)NOCCO)cc21]

Alternative names for binimetinib include MEK162, ARRY-162, ARRY-438162, and 5-((4-bromo-2-fluorophenyl)amino)-4-fluoro-N-(2-hydroxyethoxy)-1-methyl-1H-benzo[d]imidazole-6-carboxamide. Binimetinib is associated with CAS Registry Number 606143-89-9.

The term "biological sample," as used herein, encompasses a variety of sample types obtained from an organism and can be used in a diagnostic or monitoring assay. The sample may be of a healthy tissue, diseased tissue, or tissue suspected of being diseased tissue. The sample may be a biopsy taken, for example, during a surgical procedure. The sample may be collected via means of fine needle aspiration, scraping or washing a cavity to collects cells or tissue therefrom. The sample may be of a tumor such as, for example, solid and hematopoietic tumors as well as of neighboring healthy tissue. The sample may be a smear of individual cells or a tissue section. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses clinical samples, and also includes cells in cell culture, cell supernatants, cell lysates, cell extracts, cell homogenates, subcellular components including synthesized proteins, serum, plasma, bodily and other biological fluids, and tissue samples. The biological sample can contain compounds that are not naturally intermixed with the cell or tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

The term "biomarker," as used herein, means a molecule whose level of nucleic acid or protein product has a quantitatively differential concentration or level with respect to an aspect of a biological state of a patient. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the patient's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present disclosure include ALK, ROS1, TrkA, TrkB, and TrkC.

As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but are not limited to sarcomas and carcinomas. Examples of cancers of the blood include but are not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. These terms also mean the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In certain embodiments, the cancer is a solid tumor, a soft tissue tumor, or a metastatic lesion.

The term "chemotherapeutic agent," as used herein, means a chemical substance, such as a cytotoxic or cytostatic agent, that is used to treat a condition, particularly cancer.

As used herein, the term "Cmax" means the peak concentration that a compound achieves in the plasma of a patient after the compound, or a pharmaceutical composition comprising the compound, has been administered to the patient. In some embodiments, the compound, or a pharmaceutical composition comprising the compound, is administered orally to a patient to achieve a particular Cmax.

The term "cobimetinib," as used herein, means the compound having the chemical structure,

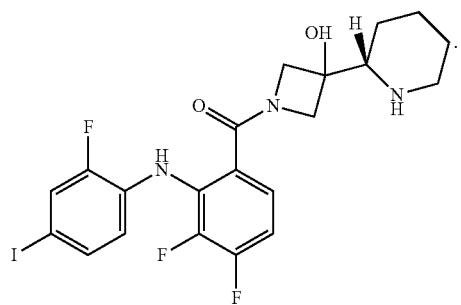 [SMILES: O=C(c1ccc(F)c(F)c1Nc1ccc(I)cc1F)N1CC(O)([C@@H]2CCCCN2)C1]

Alternative names for cobimetinib include GDC-0973, XL-518, RG7420, Cotellic™, and (S)[3,4-difluoro-2-(2-fluoro-4-iodophenylamino)phenyl]3-hydroxy-3-(piperidin-2-yl]azetidin-1-yl)methanone. Cobimetinib is associated with CAS Registry Number 934660-93-2.

The terms "combination" and "in combination with," as used herein, mean the administration of a compound provided herein together with an at least one additional pharmaceutical or medicinal agent (e.g., an anti-cancer agent), either sequentially or simultaneously. It includes dosing simultaneously, or within minutes or hours of each other, or on the same day, or on alternating days, or dosing the compound provided herein on a daily basis, or multiple days per week, or weekly basis, for example, while administering another compound such as a chemotherapeutic agent on the same day or alternating days or weeks or on a periodic basis during a time simultaneous therewith or concurrent therewith, or at least a part of the time during which the compound provided herein is dosed. For example, N-[5-(3, 5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof could be dosed every day or several days a week while the chemotherapeutic agent is dosed on alternating days or alternating weeks or other periods of time, such as every 1, 2, 3, 4, 5, 6, 7, 8, 9, 10, 11. 12, 13, 14 or more days.

The term "E6201," as used herein, means the compound having the chemical structure,

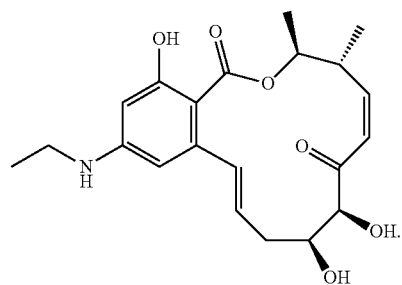 [SMILES: CCNc1cc(O)c2c(c1)/C=C/C[C@H](O)[C@H](O)C(=O)/C=C\[C@@H](C)[C@H](C)OC2=O]

Alternative names for E6201 include (3S,4R,5Z,8S,9S,11E)-14-(ethylamino)-8,9,16-trihydroxy-3,4-dimethyl-3,4,9,10-tetrahydro-1H-2-benzoxacyclotetradecine-1,7 (8H)-dione. E6201 is associated with CAS Registry Number 603987-35-5.

The term "ERK," as used herein, means the family of extracellular signal-regulated kinases (ERKs), and are protein kinase intracellular signaling molecules. ERKs include, but are not limited to, ERK1 and ERK2. As used herein, the term "ERK1" means extracellular signal-regulated kinase 1 having the UniProt identifier MK03 HUMAN and encoded by the MAPK3 gene. As used herein, the term "ERK2" means extracellular signal-regulated kinase 2 having the UniProt identifier MK01_HUMAN and encoded by the MAPK1 gene. ERK1 and ERK2 are also referred to by those having ordinary skill in the art as MAPK3 and MAPK1, respectively. A reference to ERK1 is a reference to MAPK3. A reference to ERK2 is a reference to MAPK1. Unless otherwise indicated, use of the term "ERK" may refer to ERK1, ERK2, or a combination thereof.

The term "food effect," as used herein, means a change in the rate and/or extent of absorption of a compound in a patient when the compound is administered to the patient shortly after a meal (fed conditions) as compared to the rate and/or extent of absorption of the compound when the compound is administered to the patient under fasting conditions. As used herein, the term "no food effect" means that there is no significant difference in the rate and/or extent of absorption of a compound in a patient when the compound is administered to the patient in fed conditions compared to fasting conditions.

The term "GDC-0623," as used herein, means the compound having the chemical structure,

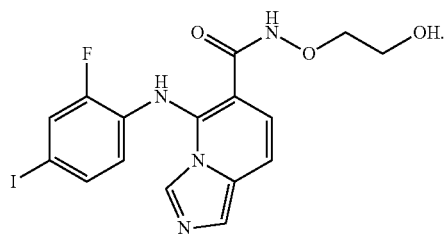 [SMILES: O=C(NOCCO)c1ccc2cncn2c1Nc1ccc(I)cc1F]

Alternative names for GDC-0623 include 5-[(2-fluoro-4-iodophenyl)amino]-N-(2-hydroxyethoxy)-imidazo[1,5-a]pyridine-6-carboxamide. GDC-0623 is associated with CAS Registry Number 1168091-68-6.

The term "HE-3235," as used herein, means the compound having the chemical structure,

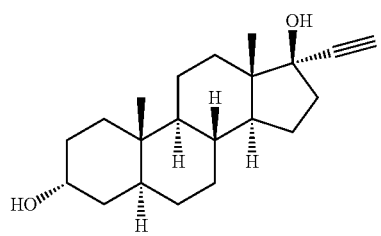

Alternative names for HE-3235 include HE3235, H E3235, Apotone®, and (3R,5S,8R,9S,10S,13S,14S,17R)-17-ethynyl-10,13-dimethylhexadecahydro-1H-cyclopenta[a]phenanthrene-3,17-diol. HE-3235 is associated with CAS Registry Number 183387-50-0.

The term "IDN-5491," as used herein, means the compound having the chemical structure,

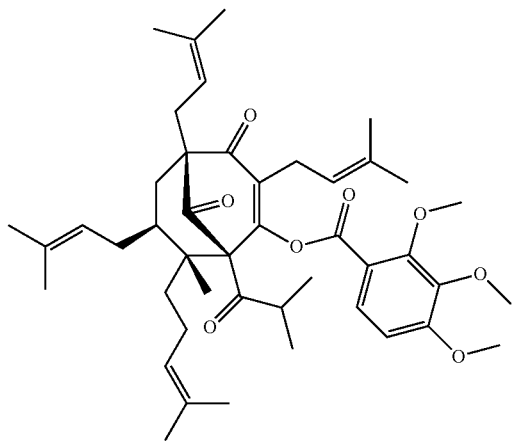

Alternative names for IDN-5491 include hyperforin triemthoxybenzoate and (1S,5R,7 S,8R)-1-isobutyryl-8-methyl-3,5,7-tris(3-methyl-2-buten-1-yl)-8-(4-methyl-3-penten-1-yl)-4,9-dioxobicyclo[3.3.1]non-2-en-2-yl 2,3,4-trimethoxybenzoate.

The term "MEK," as used herein, means the family of mitogen/extracellular signal-regulated kinases (MEKs), and are kinase enzymes which phosphorylate mitogen-activated protein kinase (MAPK). MEK is also known as MAP2K and MAPKK. Isoforms of MEK include, but are not limited to, MEK1 and MEK2. As used herein, the term "MEK1" means mitogen/extracellular signal-regulated kinase-1 having the UniProt identifier MP2K1_HUMAN and encoded by the MAP2K1 gene. As used herein, the term "MEK2" means mitogen/extracellular signal-regulated kinase-2 having the UniProt identifier MP2K2_HUMAN and encoded by the MAP2K2 gene. Unless otherwise indicated, use of the term "MEK" may refer to MEK1, MEK2, or a combination thereof.

The term "microarray," as used herein, is an ordered arrangement of array elements (for example, small samples of a biological sample from a patient such as tissue samples) mounted on a solid support capable of binding other molecule species or antibodies. The array elements are arranged so that there are preferably at least one or more different array elements.

The terms "molecular alteration" and "genetic alteration," as used herein, mean any variation in the genetic or protein sequence in or more cells of a patient as compared to the corresponding wild-type genes or proteins. One or more molecular alterations include, but are not limited to, genetic mutations, gene amplifications, splice variants, deletions, gene rearrangements, single-nucleotide variations (SNVs), insertions, and aberrant RNA/protein expression. The terms "molecular alteration" and "genetic alteration" are used interchangeably herein.

The term "patient," as used herein, means a mammal, including, but not limited to, a human, a dog or a cat. In some embodiments, the patient is a human. In some embodiments, the patient is a dog. In some embodiments, the patient is a cat.

The term "PD0325901," as used herein, means the compound having the chemical structure,

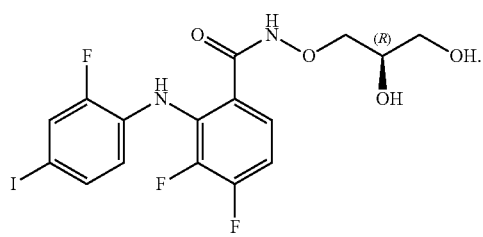

Alternative names for PD0325901 include PD 0325901, PD325901, and N-[(2R)-2,3-dihydroxypropoxy]-3,4-difluoro-2-[(2-fluoro-4-iodophenyl)amino]-benzamide. PD0325901 is associated with CAS Registry Number 391210-10-9.

The term "PD184352," as used herein, means the compound having the chemical structure,

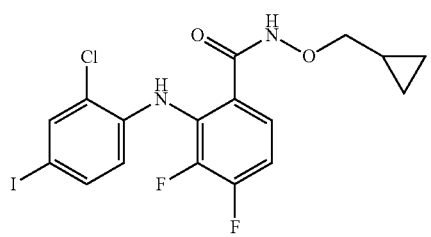

Alternative names for PD184352 include CI-1040 and 2-(2-chloro-4-iodophenylamino)-N-cyclopropylmethoxy-3,4-difluorobenzamide. PD184352 is associated with CAS Registry Number 212631-79-3.

The term "pimasertib," as used herein, means the compound having the chemical structure,

[structure shown]

Alternative names for pimasertib include AS-703026, AS 703026, AS703026, MSC1936369B, N-[(2S)-2,3-dihydroxypropyl]-3-(2-fluoro-4-iodoanilino)pyridine-4-carboxamide, and N-(2,3-dihydroxypropyl)-1-((2-fluoro-4-iodophenyl)amino)isonicotinamide. Pimasertib is associated with CAS Registry Number 1236699-92-5.

The term "refametinib," as used herein means the compound having the chemical structure,

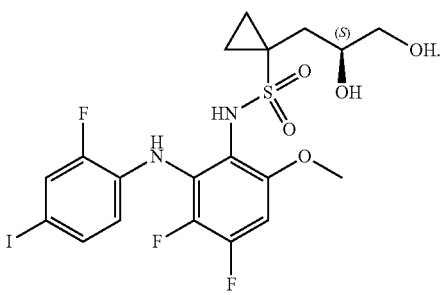

Alternative names for refametinib include BAY-86-9766, RDEA119, and N-[3,4-difluoro-2-[(2-fluoro-4-iodophenyl)amino]-6-methoxy phenyl]-1-[(2S)-2,3-dihydroxypropyl]-cyclopropanesulfonamide. Refametinib is associated with CAS Registry Number 923032-37-5.

The term "RO4987655," as used herein, means the compound having the chemical structure,

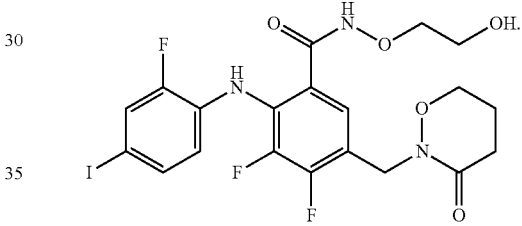

Alternative names for RO4987655 include RO 4987655, RO-4987655, RG 7167, CH-4987655, CH 4987655, CH4987655, and 3,4-difluoro-2-(2-fluoro-4-iodoanilino)-N-(2-hydroxyethoxy)-5-[(3-oxooxazinan-2-yl)methyl]benzamide. RO4987655 is associated with CAS Registry Number 874101-00-5.

The term "RO5126766," as used herein, means the compound having the chemical structure,

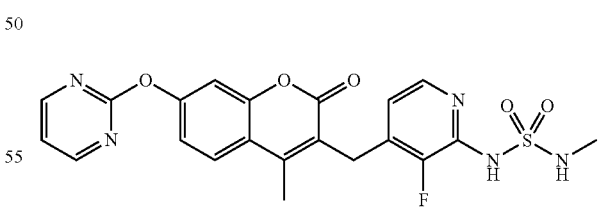

Alternative names for RO5126766 include RO-5126766 and CH5126766. RO5126766 is associated with CAS Registry Number 946128-88-7.

The term "ROS1," as used herein, means the ROS1 receptor tyrosine-protein kinase having the UniProt designation ROS1_HUMAN and encoded by the ROS1 gene.

The term "selumetinib," as used herein, means the compound having the chemical structure,

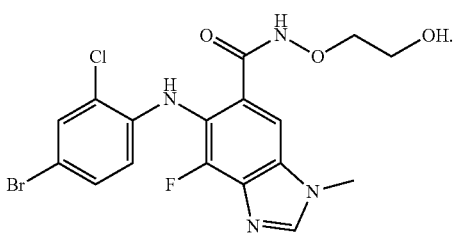 [SMILES: Cn1cnc2c(F)c(Nc3ccc(Br)cc3Cl)c(C(=O)NOCCO)cc21]

Alternative names for selumetinib include AZD6244, ARRY-142886, and 6-(4-bromo-2-chloroanilino)-7-fluoro-N-(2-hydroxyethoxy)-3-methylbenzimidazole-5-carboxamide. Selumetinib is associated with CAS Registry Number 606143-52-6.

The term "solid support," as used herein, means the well-understood solid materials to which various components such as, for example, proteins and nucleic acids, are physically attached, thereby immobilizing the components. The term "solid support," as used herein, means a non-liquid substance. A solid support can be, but is not limited to, a membrane, sheet, gel, glass, plastic or metal. Immobilized components may be associated with a solid support by covalent bonds and/or via non-covalent attractive forces such as hydrogen bond interactions, hydrophobic attractive forces and ionic forces, for example The term "sorafenib," as used herein, means the compound having the chemical structure,

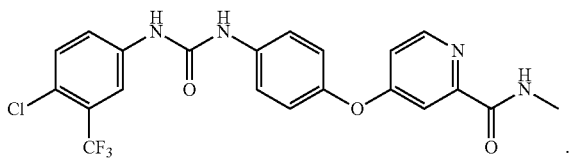 [SMILES: CNC(=O)c1cc(Oc2ccc(NC(=O)Nc3ccc(Cl)c(C(F)(F)F)c3)cc2)ccn1]

Alternative names for sorafenib include BAY 43-9006, Nexavar®, and 4-[4-[[4-chloro-3-(trifluoromethyl)phenyl]carbamoylamino]phenoxy]-N-methyl-pyridine-2-carboxamide. Sorafenib is associated with CAS Registry Number 284461-73-0.

The term "TAK-733" as used herein, means the compound having the chemical structure,

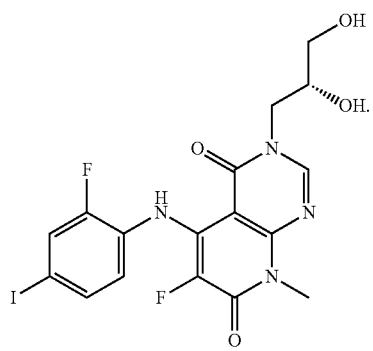 [SMILES: Cn1c(=O)c(F)c(Nc2ccc(I)cc2F)c2c(=O)n(C[C@@H](O)CO)cnc21]

Alternative names for TAK-733 include (R)-3-(2,3-dihydroxypropyl)-6-fluoro-5-(2-fluoro-4-iodophenylamino)-8-methylpyrido[2,3-d]pyrimidine-4,7(3H,8H)-dione. TAK-733 is associated with CAS Registry Number 1035555-63-5.

The term "therapeutically effective amount," as used herein, means that amount of the compound or compounds being administered which will relieve to some extent one or more of the symptoms of the disorder being treated. In reference to the treatment of a cancer, a therapeutically effective amount refers to that amount which has the effect of (1) reducing the size of a cancer tumor, (2) inhibiting (that is, slowing to some extent, preferably stopping) cancer tumor metastasis, (3) inhibiting to some extent (that is, slowing to some extent, preferably stopping) cancer tumor growth, and/or, (4) relieving to some extent (or, preferably, eliminating) one or more symptoms associated with the cancer.

The term "trametinib" as used herein, means the compound having the chemical structure,

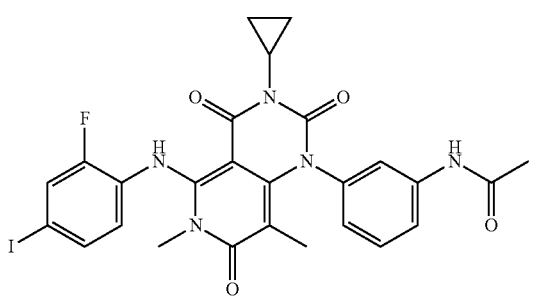

Alternative names for trametinib include GSK1120212 and Mekinist®. Trametinib is associated with CAS Registry Number 871700-17-3.

The term "tropomyosin receptor kinase," as used herein, means the family of tropomyosin receptor kinases (Trks) that are activated by peptide hormones of the neurotrophin family and include, but are not limited to, TrkA, TrkB, and TrkC. As used herein, the term "TrkA" means wild-type tropomyosin receptor kinase A having the UniProt identifier NTRK1_HUMAN and encoded by the NTRK1 gene. As used herein, the term "TrkB" means wild-type tropomyosin receptor kinase B having the UniProt identifier NTRK2_HUMAN and encoded by the NTRK2 gene. As used herein, the term "TrkC" means wild-type tropomyosin receptor kinase C having the UniProt identifier NTRK3_HUMAN and encoded by the NTRK3 gene. TrkA, TrkB and TrkC are also referred to by those having ordinary skill in the art as Trk1, Trk2 and Trk3, respectively. A reference to TrkA is a reference to Trk1. A reference to TrkB is a reference to Trk2. A reference to TrkC is a reference to Trk3.

The term "ulixertinib," as used herein, means the compound having the chemical structure,

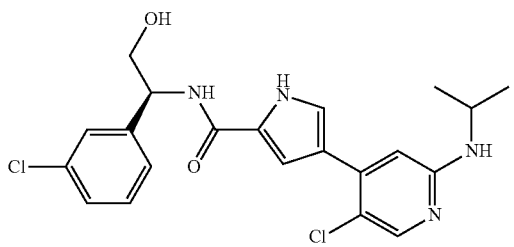

Alternative names for ulixertinib include BVD-523, VRT752271, and 4-(5-chloro-2-(isopropylamino)pyridin-4-yl)-N-((S)-1-(3-chlorophenyl)-2-hydroxyethyl)-1H-pyrrole-2-carboxamide. Ulixertinib is associated with CAS Registry Number 869886-67-9.

Provided herein, in one aspect, are methods of treating cancer in a patient in need thereof, the methods comprising administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof.

In another aspect, provided herein are methods of treating cancer in a patient in need thereof, the methods comprising administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof; and the second agent comprises a MEK inhibitor or an ERK inhibitor.

In another aspect, provided herein are methods of treating cancer in a patient in need thereof, the methods comprising administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof; and the second agent is a MEK inhibitor or an ERK inhibitor.

In another aspect, provided herein are methods of treating cancer in a patient in need thereof, the methods comprising administering to the patient a combination comprising a therapeutically effective amount of a first agent and a therapeutically effective amount of a second agent, wherein the first agent is an ALK inhibitor; the second agent is a MEK inhibitor or an ERK inhibitor; and the patient has at least one genetic alteration in ALK.

In another aspect, provided herein are methods of treating cancer in a patient in need thereof, the method comprising administering to the patient a combination comprising a therapeutically effective amount of a first agent and a therapeutically effective amount of a second agent, wherein the first agent is an ALK inhibitor; the second agent is a MEK inhibitor or an ERK inhibitor; and the patient has at least one mutation in the ALK receptor tyrosine kinase polypeptide.

In another aspect, provided herein are methods of treating cancer in a patient in need thereof, the methods comprising administering to the patient a combination comprising a therapeutically effective amount of a first agent and a therapeutically effective amount of a second agent, wherein the first agent is a ROS1 inhibitor; the second agent is a MEK inhibitor or an ERK inhibitor; and the patient has at least one genetic alteration in ROS1.

In another aspect, provided herein are methods of treating cancer in a patient in need thereof, the method comprising administering to the patient a combination comprising a therapeutically effective amount of a first agent and a therapeutically effective amount of a second agent, wherein the first agent is a ROS1 inhibitor; the second agent is a MEK inhibitor or an ERK inhibitor; and the patient has at least one mutation in the ROS1 receptor tyrosine kinase polypeptide.

In another aspect, provided herein are methods of treating cancer in a patient in need thereof, the methods comprising administering to the patient a combination comprising a therapeutically effective amount of a first agent and a therapeutically effective amount of a second agent, wherein the first agent is a TrkA inhibitor; the second agent is a MEK inhibitor or an ERK inhibitor; and the patient has at least one genetic alteration in NTRK1.

In another aspect, provided herein are methods of treating cancer in a patient in need thereof, the method comprising administering to the patient a combination comprising a therapeutically effective amount of a first agent and a therapeutically effective amount of a second agent, wherein the first agent is a TrkA inhibitor; the second agent is a MEK inhibitor or an ERK inhibitor; and the patient has at least one mutation in the TrkA receptor tyrosine kinase polypeptide.

In another aspect, provided herein are methods of treating cancer in a patient in need thereof, the methods comprising administering to the patient a combination comprising a therapeutically effective amount of a first agent and a therapeutically effective amount of a second agent, wherein the first agent is a TrkB inhibitor; the second agent is a MEK inhibitor or an ERK inhibitor; and the patient has at least one genetic alteration in NTRK2.

In another aspect, provided herein are methods of treating cancer in a patient in need thereof, the method comprising administering to the patient a combination comprising a therapeutically effective amount of a first agent and a therapeutically effective amount of a second agent, wherein the first agent is a TrkB inhibitor; the second agent is a MEK inhibitor or an ERK inhibitor; and the patient has at least one mutation in the TrkB receptor tyrosine kinase polypeptide.

In another aspect, provided herein are methods of treating cancer in a patient in need thereof, the method comprising administering to the patient a combination comprising a therapeutically effective amount of a first agent and a therapeutically effective amount of a second agent, wherein the first agent is a TrkC inhibitor; the second agent is a MEK inhibitor or an ERK inhibitor; and the patient has at least one genetic alteration in NTRK3.

In another aspect, provided herein are methods of treating cancer in a patient in need thereof, the method comprising administering to the patient a combination comprising a therapeutically effective amount of a first agent and a therapeutically effective amount of a second agent, wherein the first agent is a TrkC inhibitor; the second agent is a MEK inhibitor or an ERK inhibitor; and the patient has at least one mutation in the TrkC receptor tyrosine kinase polypeptide.

In some embodiments, knowledge of the at least one genetic alteration is acquired from an antibody-based assay. The antibody-based assay can generally be any antibody-based assay, and can be, for example, ELISA, immunohistochemistry, western blotting, mass spectrometry, flow cytometry, protein-microarray, immunofluorescence, and a multiplex detection assay. In some embodiments, the antibody-based assay includes an immunohistochemistry analysis.

In some embodiments, identifying a ALK, ROS1, TrkA, TrkB, or TrkC modulation defect such as an up-regulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises assaying for ALK, ROS1, TrkA, TrkB, or TrkC activity in a cell extract from a pancreatic cancerous or precancerous cell population. In some embodiments, identifying a ALK, ROS1, TrkA, TrkB, or TrkC modulation defect such as an up-regulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises assaying for ALK, ROS1, TrkA, TrkB, or TrkC transcript accumulation in an RNA population from a pancreatic cancerous or precancerous cell population. In some embodiments, identifying a ALK, ROS1, TrkA, TrkB, or TrkC modulation defect such as an up-regulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises determining the nucleic acid sequence such as the genomic deoxyribonucleic acid sequence in a cell or cells or a cell population comprising a cell or cells from a pancreatic cancerous or precancerous cell population.

In some embodiments, methods of the present disclosure are to treat, reduce the symptoms of, ameliorate the symptoms of, delay the onset of, or otherwise pharmaceutically address a condition in a patient selected from non-small cell lung cancer, papillary thyroid cancer, neuroblastoma, pancreatic cancer and colorectal cancer and possibly other indications in which a defect in the modulation of ALK, ROS1, TrkA, TrkB, or TrkC activity, or a combination thereof, or up-regulation, misregulation or deletion thereof might play a role by administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments, methods of the present disclosure are to treat, reduce the symptoms of, ameliorate the symptoms of, delay the onset of, or otherwise pharmaceutically address a condition in a patient selected from non-small cell lung cancer, papillary thyroid cancer, neuroblastoma, pancreatic cancer and colorectal cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous cell in the patient, and administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods for treating cancer in a patient in need thereof, the method comprising: (a) acquiring knowledge of the presence of at least one genetic alteration in a biological sample from the patient, wherein the at least one genetic alteration is detected by an assay comprising one or more antibodies that bind to one or more of ALK, ROS1, TrkA, TrkB, and TrkC biomarkers; (b) and administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods for treating cancer in a patient in need thereof, the method comprising: (1) testing one or more cells comprising a tumor from the patient for the presence of at least one of ALK, ROS1, TrkA, TrkB, or TrkC; and (2) if the one or more cells tests positive for at least one of ALK, ROS1, TrkA, TrkB, or TrkC, administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods for treating cancer in a patient in need thereof, the method comprising: (1) testing one or more cells comprising tumor tissue from the patient for the presence of at least one of ALK, ROS1, TrkA, TrkB, or TrkC; and (2) if the one or more cells tests positive for at least one of ALK, ROS1, TrkA, TrkB, or TrkC, administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods for treating cancer in a patient in need thereof, the method comprising: (a) acquiring knowledge of the presence of at least one genetic alteration in at least one target gene in the cancer patient, wherein the at least one target gene is selected from ALK1, BDNF, NGF, NGFR, NTF3, NTF4, ROS1, SORT1, NTRK1, NTRK2, and NTRK3; and (b) administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor based on the recognition that the combination is effective in treating cancer patients having the at least one genetic alteration in the at least one target gene. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods for treating cancer in a patient in need thereof, the method comprising administering to the patient a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor, and wherein prior to the administration of the combination, the patient is known to possess at least one genetic alteration in at least one target gene selected from ALK1, BDNF, NGF, NGFR, NTF3, NTF4, ROS1, SORT1, NTRK1, NTRK2, and NTRK3. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods for treating cancer in a patient known to possess at least one genetic alteration in at least one target gene selected from ALK1, BDNF, NGF, NGFR, NTF3, NTF4, ROS1, SORT1, NTRK1, NTRK2, and NTRK3 a therapeutically effective amount of a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods of treating a cancer patient, the method comprising administering to the patient a therapeutically effective amount of a combination comprising a therapeutically effective amount of a first agent and a therapeutically effective amount of a second agent, wherein the first agent is an inhibitor of ALK, ROS1, TrkA, TrkB, or TrkC activity, or a combination thereof; the second agent is selected from a MEK inhibitor and an ERK inhibitor; the cancer patient is has at least one genetic alteration in at least one target gene; and the target gene is selected from ALK1, BDNF, NGF, NGFR, NTF3, NTF4, ROS1, SORT1, NTRK1, NTRK2, and NTRK3. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods of treating a cancer patient, comprising (a) acquiring knowledge of the presence of at least one genetic alteration in at least one target gene selected from ALK1, BDNF, NGF, NGFR, NTF3, NTF4, ROS1, SORT1, NTRK1, NTRK2, and NTRK3 in the patient; and (b) administering to the patient a therapeutically effective amount of a combination comprising a therapeutically effective amount of a first agent and a therapeutically effective amount of a second agent, wherein the first agent is an inhibitor of ALK, ROS1, TrkA, TrkB, or TrkC activity, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the MEK inhibitor is a MEK1 inhibitor, a MEK2 inhibitor, or a combination thereof. In some embodiments, the MEK inhibitor is selected from PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the ERK inhibitor is an ERK1 inhibitor, an ERK2 inhibitor, or a combination thereof. In some embodiments, the ERK inhibitor is selected from TG-02, MK-8353, ulixertinib, HE-3235, AEZS-134, AEZS-136, and IDN-5491.

In some embodiments are provided methods wherein the tumors are caused by the presence of non-small cell lung cancer, papillary thyroid cancer, neuroblastoma, pancreatic cancer or colorectal cancer in the patient. In some embodiments are provided methods wherein one or more of the cells comprising the tumors in the patient test positive for the presence of a gene that expresses at least one of ALK, ROS1, TrkA, TrkB, or TrkC kinase or one or more of the cells comprising the tumors in the patient demonstrates at least one of ALK, ROS1, TrkA, TrkB, or TrkC kinase activity.

In some embodiments are provided methods wherein one or more of the cells comprising the tumors in the patient test positive for at least one gene rearrangement comprising a gene, or a fragment thereof, that expresses at least one of ALK, ROS1, TrkA, TrkB, or TrkC. In some embodiments are provided such methods wherein the cells test positive for at least one of ROS1, TrkA, TrkB, or TrkC. In some embodiments are provided methods wherein the cells test positive for ALK. In some embodiments are provided methods wherein the cells test positive for ROS1. In some embodiments are provided methods wherein the cells test positive for at least one of TrkA, TrkB and TrkC. In some embodiments are provided methods wherein the cells test positive for TrkA. In some embodiments are provided methods wherein the cells test positive for TrkB. In some embodiments are provided such methods wherein the cells test positive for TrkC.

In some embodiments are provided methods of treating cancer in a patient in need thereof, the method comprising: (1) testing one or more cells comprising the tumors in the patient for the presence of at least one of ALK, ROS1, TrkA, TrkB, or TrkC; and (2) if the one or more cells tests positive for at least one of ALK, ROS1, TrkA, TrkB, or TrkC activity, administering to the patient a combination comprising a therapeutically effective amount of a first agent and a therapeutically effective amount of a second agent, wherein the first agent is an ALK inhibitor, a ROS1 inhibitor, a TrkA inhibitor, a TrkB inhibitor, or a TrkC inhibitor, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided methods of treating cancer in a patient in need thereof, the method comprising: (1) testing one or more cells comprising the tumors in the patient for the presence of ALK; and (2) if the one or more cells tests positive for ALK activity, administering to the patient a combination comprising a therapeutically effective amount of a first agent and a therapeutically effective amount of a second agent, wherein the first agent is an ALK inhibitor and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided methods of treating cancer in a patient in need thereof, the method comprising: (1) testing one or more cells comprising the tumors in the patient for the presence of ROS1; and (2) if the one or more cells tests positive for ROS1 activity, administering to the patient a combination comprising a therapeutically effective amount of a first agent and a therapeutically effective amount of a second agent, wherein the first agent is an inhibitor of ROS1 and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided methods of treating cancer in a patient in need thereof, the method comprising: (1) testing one or more cells comprising the tumors in the patient for the presence of TrkA, TrkB, or TrkC, or a combination thereof; and (2) if the one or more cells tests positive for TrkA, TrkB, or TrkC activity, or a combination thereof, administering to the patient a combination comprising a therapeutically effective amount of a first agent and a therapeutically effective amount of a second agent, wherein the first agent is an inhibitor of TrkA, TrkB, or TrkC, or a combination thereof, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided methods of treating cancer in a patient in need thereof, the method comprising: (1) testing one or more cells comprising the tumors in the patient for the presence of TrkA; and (2) if the one or more cells tests positive for TrkA activity, administering to the patient a combination comprising a therapeutically effective amount of a first agent and a therapeutically effective amount of a second agent, wherein the first agent is an inhibitor of TrkA, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided methods of treating cancer in a patient, the method comprising: (1) testing one or more cells comprising the tumors in the patient for the presence of TrkB; and (2) if the one or more cells tests positive for TrkB activity, administering to the patient a combination comprising a therapeutically effective amount of a first agent and a therapeutically effective amount of a second agent, wherein the first agent is an inhibitor of TrkB, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided methods of treating cancer in a patient, the method comprising: (1) testing one or more cells comprising the tumors in the patient for the presence of TrkC; and (2) if the one or more cells tests positive for TrkC activity, administering to the patient a combination comprising a therapeutically effective amount of a first agent and a therapeutically effective amount of a second agent, wherein the first agent is an inhibitor of TrkC, and the second agent is selected from a MEK inhibitor and an ERK inhibitor. In some embodiments, the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments of the methods provided herein, the patient has at least one mutation in the TrkA receptor tyrosine kinase polypeptide. For example, the at least one mutation in the TrkA receptor tyrosine kinase polypeptide may be a genetic alteration of SEQ ID NO: 1. In some embodiments, the at least one mutation in the TrkA receptor tyrosine kinase polypeptide is at a position corresponding to amino acid residue G595 or G667 of the TrkA polypeptide set forth in SEQ ID NO: 1. In some embodiments, the at least one mutation in the TrkA receptor tyrosine kinase polypeptide is at the position corresponding to amino acid residue G595 of the TrkA polypeptide set forth in SEQ ID NO: 1. In some embodiments, the at least one mutation in the TrkA receptor tyrosine kinase polypeptide is Glu-to-Arg substitution (G595R). In some embodiments, the at least one mutation in the TrkA receptor tyrosine kinase polypeptide is at the position corresponding to amino acid residue G667 of the TrkA polypeptide set forth in SEQ ID NO: 1. In some embodiments, the at least one mutation in the TrkA receptor tyrosine kinase polypeptide is Glu-to-Cys substitution (G667C).

In some embodiments of the methods provided herein, the patient at least one mutation in the TrkB receptor tyrosine kinase polypeptide. For example, the at least one mutation in the TrkB receptor tyrosine kinase polypeptide may be a genetic alteration of SEQ ID NO: 2. In some embodiments, the at least one mutation in the TrkB receptor tyrosine kinase polypeptide is at a position corresponding to amino acid residue G639 or G709 of the TrkB polypeptide set forth in SEQ ID NO: 2. In some embodiments, the at least one mutation in the TrkB receptor tyrosine kinase polypeptide is at the position corresponding to amino acid residue G639 of the TrkB polypeptide set forth in SEQ ID NO: 2. In some embodiments, the at least one mutation in the TrkB receptor tyrosine kinase polypeptide is Glu-to-Arg substitution (G639R). In some embodiments, the at least one mutation in the TrkB receptor tyrosine kinase polypeptide is at the position corresponding to amino acid residue G709 of the TrkB polypeptide set forth in SEQ ID NO: 2. In some embodiments, the at least one mutation in the TrkB receptor tyrosine kinase polypeptide is Glu-to-Cys substitution (G709C).

In some embodiments of the methods provided herein, the patient has at least one mutation in the TrkC receptor tyrosine kinase polypeptide. For example, the at least one mutation in the TrkC receptor tyrosine kinase polypeptide may be a genetic alteration of SEQ ID NO: 3. In some embodiments, the at least one mutation in the TrkC receptor tyrosine kinase polypeptide is at a position corresponding to amino acid residue G623 or G696 of the TrkC polypeptide set forth in SEQ ID NO: 3. In some embodiments, the at least one mutation in the TrkC receptor tyrosine kinase polypeptide is at the position corresponding to amino acid residue G623 of the TrkC polypeptide set forth in SEQ ID NO: 3. In some embodiments, the at least one mutation in the TrkC receptor tyrosine kinase polypeptide is Glu-to-Arg substitution (G623R). In some embodiments, the at least one mutation in the TrkC receptor tyrosine kinase polypeptide is at the position corresponding to amino acid residue G696 of the TrkC polypeptide set forth in SEQ ID NO: 3. In some embodiments, the at least one mutation in the TrkC receptor tyrosine kinase polypeptide is Glu-to-Cys substitution (G696C).

In some embodiments of the methods provided herein, the patient has at least one mutation in ALK receptor tyrosine kinase polypeptide. For example, the at least one mutation in the ALK receptor tyrosine kinase polypeptide may be a genetic alteration of SEQ ID NO: 4. In some embodiments, the at least one mutation in the ALK receptor tyrosine kinase polypeptide is at a position corresponding to amino acid residue G1202 or G1269 of the ALK polypeptide set forth in SEQ ID NO: 4. In some embodiments, the at least one mutation in the ALK receptor tyrosine kinase polypeptide is at the position corresponding to amino acid residue G1202 of the ALK polypeptide set forth in SEQ ID NO: 4. In some embodiments, the at least one mutation in the ALK receptor tyrosine kinase polypeptide is at the position corresponding to amino acid residue G1269 of the ALK polypeptide set forth in SEQ ID NO: 4.

In some embodiments of the methods provided herein, the patient has at least one mutation in the ROS1 receptor tyrosine kinase polypeptide. For example, the at least one mutation in the ROS1 receptor tyrosine kinase polypeptide may be a genetic alteration of SEQ ID NO: 5. In some embodiments, the at least one mutation in the ROS1 receptor tyrosine kinase polypeptide is at a position corresponding to amino acid residue G2032 or G2101 of the ROS1 polypeptide set forth in SEQ ID NO: 5. In some embodiments, the at least one mutation in the ROS1 receptor tyrosine kinase polypeptide is at the position corresponding to amino acid residue G2032 of the ROS1 polypeptide set forth in SEQ ID NO: 5. In some embodiments, the at least one mutation in the ROS1 receptor tyrosine kinase polypeptide is at the position corresponding to amino acid residue G2101 of the ROS1 polypeptide set forth in SEQ ID NO: 5.

In some embodiments, the combination is a pharmaceutical composition comprising the therapeutically effective amount of the first agent, the therapeutically effective amount of the second agent, and at least one pharmaceutically acceptable carrier.

In some embodiments, the combination is concurrent administration of a first pharmaceutical composition comprising the therapeutically effective amount of the first agent and a second pharmaceutical composition comprising the therapeutically effective amount of the second agent In some embodiments, the combination is sequential administration of a first pharmaceutical composition comprising the therapeutically effective amount of the first agent and a second pharmaceutical composition comprising the therapeutically effective amount of the second agent. In some embodiments, the first pharmaceutical composition is administered prior to the second pharmaceutical composition. In some embodiments, the first pharmaceutical composition is administered after the second pharmaceutical composition.

In some embodiments are provided any of the methods described herein wherein the patient is suffering from cancer selected from non-small cell lung cancer, papillary thyroid cancer, neuroblastoma, melanoma, pancreatic cancer, and colorectal cancer.

In some embodiments are provided any of the methods described herein wherein the patient is suffering from cancer selected from non-small cell lung cancer, neuroblastoma, melanoma, pancreatic cancer and colorectal cancer.

In some embodiments are provided any of the methods described herein wherein the patient is suffering from cancer selected from non-small cell lung cancer, neuroblastoma, melanoma, and colorectal cancer.

In some embodiments are provided any of the methods described herein wherein the patient is suffering from cancer selected from non-small cell lung cancer, neuroblastoma, and colorectal cancer.

In some embodiments are provided any of the methods described herein wherein the patient is suffering from non-small cell lung cancer.

In some embodiments are provided any of the methods described herein wherein the patient is suffering from papillary thyroid cancer.

In some embodiments are provided any of the methods described herein wherein the patient is suffering from neuroblastoma.

In some embodiments are provided any of the methods described herein wherein the patient is suffering from melanoma.

In some embodiments are provided any of the methods described herein wherein the patient is suffering from pancreatic cancer.

In some embodiments are provided any of the methods described herein wherein the patient is suffering from colorectal cancer.

In some embodiments are provided any of the methods described herein wherein the second agent comprises one or more chemotherapeutic agents or radiotherapy, such as radiotherapy as commonly administered to treat, ameliorate the symptoms of, or prevent or delay the onset of cancer. Such agents include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

In some embodiments are provided a product or kit comprising a combination of a first agent and a second agent as a combined preparation for simultaneous, separate or sequential use in anticancer therapy.

In some embodiments are provided a product or a kit comprising a combination of a first agent and a second agent as a combined preparation for simultaneous, separate or sequential use in anticancer therapy, wherein the first agent comprises an ALK inhibitor, a ROS1 inhibitor, a TrkA inhibitor, a TrkB inhibitor, or a TrkC inhibitor, or a combination thereof, and the second agent is selected from a MEK inhibitor and an ERK inhibitor. In some embodiments are provided a product or kit wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided a product or a kit comprising a combination of a first agent and a second agent as a combined preparation for simultaneous, separate or sequential use in anticancer therapy, wherein the first agent comprises an ALK inhibitor, and the second agent is selected from a MEK inhibitor and an ERK inhibitor. In some embodiments are provided a product or kit wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided a product or a kit comprising a combination of a first agent and a second agent as a combined preparation for simultaneous, separate or sequential use in anticancer therapy, wherein the first agent comprises a ROS1 inhibitor, and the second agent is selected from a MEK inhibitor and an ERK inhibitor. In some embodiments are provided a product or kit wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided a product or a kit comprising a combination of a first agent and a second agent as a combined preparation for simultaneous, separate or sequential use in anticancer therapy, wherein the first agent comprises a TrkA inhibitor, and the second agent is selected from a MEK inhibitor and an ERK inhibitor. In some embodiments are provided a product or kit wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided a product or a kit comprising a combination of a first agent and a second agent as a combined preparation for simultaneous, separate or sequential use in anticancer therapy, wherein the first agent comprises a TrkB inhibitor, and the second agent is selected from a MEK inhibitor and an ERK inhibitor. In some embodiments are provided a product or kit wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments are provided a product or a kit comprising a combination of a first agent and a second agent as a combined preparation for simultaneous, separate or sequential use in anticancer therapy, wherein the first agent comprises a TrkC inhibitor, and the second agent is selected from a MEK inhibitor and an ERK inhibitor. In some embodiments are provided a product or kit wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments of the methods provided herein, the first agent comprises N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

In some embodiments of the methods provided herein, the first agent and/or the second agent are administered to a patient or individual having or suffering from cancer in an amount ranging from about 200 mg/m$^2$ to about 1600 mg/m$^2$, or from about 200 mg/m$^2$ to about 1200 mg/m$^2$, or from about 200 mg/m$^2$ to about 1000 mg/m$^2$, or from about 400 mg/m$^2$ to about 1200 mg/m$^2$, or from about 400 mg/m$^2$ to about 1000 mg/m$^2$, or from about 800 mg/m$^2$ to about 1000 mg/m$^2$, or from about 800 mg/m$^2$ to about 1200 mg/m$^2$, or from about 800 mg/m$^2$ to about 1200 mg/m$^2$, or from about 800 mg/m$^2$ to about 1600 mg/m$^2$. In some embodiments, the first agent and/or the second agent are administered to the patient or individual having or suffering from cancer in an amount of about 200 mg/m$^2$, about 300 mg/m$^2$, about 400 mg/m$^2$, about 500 mg/m$^2$, about 600 mg/m$^2$, about 700 mg/m$^2$, about 800 mg/m$^2$, about 900 mg/m$^2$, about 1000 mg/m$^2$, about 1100 mg/m$^2$, about 1200 mg/m$^2$, about 1300 mg/m$^2$, about 1400 mg/m$^2$, about 1500 mg/m$^2$, about 1600 mg/m$^2$, about 1700 mg/m$^2$, about 1800 mg/m$^2$, about 1900 mg/m$^2$, or about 2000 mg/m$^2$. In some embodiments, the amount of the first agent and the amount of the second agent are within the same range listed above. In some embodiments, the amount of the first agent and the amount of the second agent are in different ranges listed above.

In some embodiments of the methods provided herein, the first agent comprises N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and is administered to a patient or individual having or suffering from cancer in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives ranges from about 200 mg/m$^2$ to about 1600 mg/m$^2$, or from about 200 mg/m$^2$ to about 1200 mg/m$^2$, or from about 200 mg/m$^2$ to about 1000 mg/m$^2$, or from about 400 mg/m$^2$ to about 1200 mg/m$^2$, or from about 400 mg/m$^2$ to about 1000 mg/m$^2$, or from about 800 mg/m$^2$ to about 1000 mg/m$^2$, or from about 800 mg/m$^2$ to about 1200 mg/m$^2$, or from about 800 mg/m$^2$ to about 1200 mg/m$^2$, or from about 800 mg/m$^2$ to about 1600 mg/m$^2$.

In some embodiments of the methods provided herein, the first agent comprises N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and is administered to a patient or individual having or suffering from cancer in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives is about 200 mg/m$^2$, about 300 mg/m$^2$, about 400 mg/m$^2$, about 500 mg/m$^2$, about 600 mg/m$^2$, about 700 mg/m$^2$, about 800 mg/m$^2$, about 900 mg/m$^2$, about 1000 mg/m$^2$, about 1100 mg/m$^2$, about 1200 mg/m$^2$, about 1300 mg/m$^2$, about 1400 mg/m$^2$, about 1500 mg/m$^2$, about 1600 mg/m$^2$, about 1700 mg/m$^2$, about 1800 mg/m$^2$, about 1900 mg/m$^2$, or about 2000 mg/m$^2$, including increments therein. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives is about 200 mg/m$^2$, about 300 mg/m$^2$, about 400 mg/m$^2$, about 500 mg/m$^2$, or about 600 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives is about 200 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives is about 300 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives is about 400 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives is about 500 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the patient receives is about 600 mg/m$^2$.

In some embodiments of the methods provided herein, the first agent and/or the second agent are administered to a patient or individual having or suffering from cancer in an amount such that the amount of the patient receives is about 0.5 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg, including increments therein.

In some embodiments, the first agent comprises N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 200 mg, about 300 mg, about 400 mg, about 500 mg, about 600 mg, about 700 mg, about 800 mg, about 900 mg, or about 1000 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 200 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 300 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 400 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 500 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 600 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 700 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 800 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 900 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives is about 1000 mg.

In some embodiments of the methods provided herein, the first agent and/or the second agent are administered to a patient or individual having or suffering from cancer in an amount such that the amount the first agent and/or second agent that the patient receives per day is about 0.5 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg, including increments therein.

In some embodiments of the methods provided herein, the first agent comprises N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and is administered to a patient or individual having or suffering from cancer in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives per day is about 0.5 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg, including increments therein. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 200 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 300 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 400 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 500 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 600 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 700 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 800 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 900 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide that the patient receives once per day is about 1000 mg.

In some embodiments, the first agent and/or the second agent are administered to a patient or individual having or suffering from cancer in multiple dosages for a treatment period of 2 to 50 days. In some embodiments, the first agent and/or the second agent are administered to a patient or individual having or suffering from cancer in multiple dosages of about 50 to about 200 mg/kg per dose over a treatment period of 5 to 42 days. In some embodiments, the first agent and/or the second agent are administered to a patient or individual having or suffering from cancer with an oral dosage of about 60 mg/kg twice a day (BID), seven times per week. In some embodiments, the first agent and/or the second agent are administered to a patient or individual having or suffering from cancer with an oral dosage of about 60 mg/kg twice a day (BID), seven times per week for six weeks, on alternate weekly basis (i.e., one week on and one week off).

Some embodiments include any of the methods described herein, wherein the first agent and/or the second agent are administered to a patient or individual having or suffering from cancer in an amount ranging from about 0.01 mg/kg to about 100 mg/kg, or from about 0.02 mg/kg to about 50 mg/kg, or from about 0.05 mg/kg to about 25 mg/kg, or from about 0.1 mg/kg to about 20 mg/kg, or from about 0.2 mg/kg to about 10 mg/kg, or from about 0.5 mg/kg to about 5 mg/kg, or from about 1 mg/kg to about 2 mg/kg. In some embodiments, the amount of the first agent and the amount of the second agent are within the same range listed above. In some embodiments, the amount of the first agent and the amount of the second agent are in different ranges listed above.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide further comprise a weakly basic organic compound and at least one acidulant. In some embodiments, the at least one acidulant is an organic acidulant. In some embodiments, the at least one acidulant is selected from tartaric acid, maleic acid, fumaric acid, citric acid, and betaine hydrochloride. In some embodiments, the at least one acidulant is fumaric acid. In some embodiments, the at least one acidulant is tartaric acid. In some embodiments, the at least one acidulant is maleic acid. In some embodiments, the at least one acidulant is citric acid. In some embodiments, the at least one acidulant is betaine hydrochloride.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide further comprise at least one acidulant. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the at least one acidulant is maleic acid. In some embodiments, the at least one acidulant is citric acid. In some embodiments, the at least one acidulant is betaine hydrochloride.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide and at least one acidulant are in the form of a tablet or capsule. In some embodiments are provided pharmaceutical compositions in the form of a tablet. In some embodiments are provided pharmaceutical compositions in the form of a capsule.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide and at least one acidulant comprises from about 10 mg to about 1000 mg of the N-[5-(3,5-difluorobenzyl)-1H-indazol-3-yl]-4-(4-methyl-piperazin-1-yl)-2-(tetrahydro-pyran-4-ylamino)-benzamide and at least one acidulant.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide when administered to a patient in a fasted state provides a pharmacokinetic profile in the patient wherein the Tmax of the N-[5-(3,5-difluorobenzyl)-1H-indazol-3-yl]-4-(4-methyl-piperazin-1-yl)-2-(tetrahydro-pyran-4-ylamino)-benzamide in the plasma of the patient is between about 2 hours and 6 hours following the administration of the pharmaceutical composition to the patient.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide when administered to a patient in a fasted state at a total dose of about 800 mg of the N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in the patient wherein the Cmax of the N-[5-(3,5-difluorobenzyl)-1H-indazol-3-yl]-4-(4-methyl-piperazin-1-yl)-2-(tetrahydro-pyran-4-ylamino)-benzamide in the plasma of the patient is between about 2080 nM and about 2110 nM following the administration of the pharmaceutical composition to the patient.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide when administered to a patient in a fed state at a total dose of about 800 mg of the N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in the patient wherein the Cmax of the N-[5-(3,5-difluorobenzyl)-1H-indazol-3-yl]-4-(4-methyl-piperazin-1-yl)-2-(tetrahydro-pyran-4-ylamino)-benzamide in the plasma of the patient is between 80% to 125% of 2560 nM, based on a 90 percent confidence interval following the administration of the pharmaceutical composition to the patient.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide when administered to a patient in a fasted state at a total dose of about 800 mg of the N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in the patient wherein the AUC(0 to 24) of the N-[5-(3,5-difluorobenzyl)-1H-indazol-3-yl]-4-(4-methyl-piperazin-1-yl)-2-(tetrahydro-pyran-4-ylamino)-benzamide in the plasma of the patient is between about 28,900 nM*hr and about 30,800 nM*hr following the administration of the pharmaceutical composition to the patient.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide that provides an AUC(0 to 24) of the N-[5-(3,5-difluorobenzyl)-1H-indazol-3-yl]-4-(4-methyl-piperazin-1-yl)-2-(tetrahydro-pyran-4-ylamino)-benzamide in the plasma of a patient of between about 28,900 nM*hr and about 30,800 nM*hr following administration of the pharmaceutical composition to the patient in a fasted state, and wherein the composition comprises a total dose of about 800 mg of the N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided any of the methods described herein wherein the pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide provide a Tmax of the N-[5-(3,5-difluorobenzyl)-1H-indazol-3-yl]-4-(4-methyl-piperazin-1-yl)-2-(tetrahydro-pyran-4-ylamino)-benzamide in the plasma of a patient of between about 2 hours and about 6 hours following administration of the pharmaceutical composition to the patient in a fasted state.

This amount will vary depending upon a variety of factors, including but not limited to the characteristics of the bioactive compositions and formulations provided herein (including activity, pharmacokinetics, pharmacodynamics, and bioavailability thereof), the physiological condition of the patient treated (including age, sex, disease type and stage, general physical condition, responsiveness to a given dosage, and type of medication) or cells, the nature of the pharmaceutically acceptable carrier or carriers in the formulation, and the route of administration. Further, an effective or therapeutically effective amount may vary depending on whether the one or more bioactive compositions and formulations provided herein is administered alone or in combination with other drug(s), other therapy/therapies or other therapeutic method(s) or modality/modalities. One skilled in the clinical and pharmacological arts will be able to determine an effective amount or therapeutically effective amount through routine experimentation, namely by monitoring a cell's or patient's response to administration of the one or more bioactive compositions and formulations provided herein and adjusting the dosage accordingly. A typical dosage may range from about 0.1 mg/kg to about 100 mg/kg or more, depending on the factors mentioned above. In other alternatives, the dosage may range from about 0.1 mg/kg to about 100 mg/kg; or about 1 mg/kg to about 100 mg/kg; or about 5 mg/kg up to about 100 mg/kg. For topical applications such as, for example, treatment of various hair conditions, according to some alternatives provided herein, suitable dosage may range from about 1 mg/kg to about 10 g/kg; or about 10 mg/kg to about 1 g/kg; or about 50 mg/kg up to about 10 g/kg. Additional guidance with regard to this aspect can be found in, for example, Remington: The Science and Practice of Pharmacy, 21st Edition, Univ. of Sciences in Philadelphia (USIP), Lippincott Williams & Wilkins, Philadelphia, Pa., 2005, which is incorporated by reference in its entirety herein.

In some embodiments, implementations of the methods according to this and other aspects of the present disclosure further include acquiring knowledge of a genetic alteration in the cancer of the patient from a second analytical assay prior to the administering step. The second analytical assay can generally be any analytical assay known to those having ordinary skill in the art, and can be for example an antibody-based assay, a nucleotide-based assay, or an enzymatic activity assay. Non-limiting examples of suitable second analytical assays include capillary electrophoresis, nucleic acid sequencing, polypeptide sequencing, restriction digestion, nucleic acid amplification-based assays, nucleic acid hybridization assay, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), and a kinase activity assay. Other examples of suitable second analytical assays include ELISA, immunohistochemistry, Western blotting, mass spectrometry, flow cytometry, protein-microarray, immunofluorescence, and multiplex detection assay.

In some embodiments, FISH analysis is used to identify the chromosomal rearrangement resulting in the one or more molecular alterations such as the fusion genes or gene products as described herein. For example, to perform FISH, at least a first probe tagged with a first detectable label can be designed to target a first gene of a fusion gene, such as in one or more exons of the gene and at least a second probe tagged with a second detectable label can be designed to target a second gene of the fusion gene, such as in one or more exons of the genes (for example, the exons containing the part of the protein that includes the tyrosine kinase domain). The at least one first probe and the at least one second probe will be closer together in a patient who carries the fusion compared to a patient who does not carry the fusion gene or gene product. In some embodiments, a variation of a FISH assay, for example, "break-apart FISH," is used to evaluate a patient selected by a method provided herein. By this method, at least one probe targeting the fusion junction and at least one probe targeting an individual gene of the fusion, e.g., at one or more exons and or introns of the gene, are utilized. In normal cells, both probes will be observed (or a secondary color will be observed due to the close proximity of the two genes of the gene fusion), and only the single gene probe will be observed when the translocation occurs or the probes, having differing colors, will be separated such that one of ordinary skill in the art observing the probes can determine that a relevant gene fusion or deletion is present in the sample. Generally, FISH assays are performed using formalin-fixed, paraffin-embedded tissue sections that are placed on slides. The DNA from the tissue sample sections is denatured to single-stranded form and subsequently allowed to hybridize with the appropriate DNA probes that can be designed and prepared using methods and techniques known to those having ordinary skill in the art. Following hybridization, any unbound probe may be removed by a series of washes and the nuclei of the cells are counter-stained with DAPI (4',6 diamidino-2-phenylindole), a DNA-specific stain that fluoresces blue. Hybridization of the probe or probes are viewed using a fluorescence microscope equipped with appropriate excitation and emission filters, allowing visualization of the fluorescent signals.

For example, a break-apart FISH assay may be used to detect multiple types of rearrangements involving the ALK gene locus. In the method, tumor cells from some patients having non-small cell lung cancer (NSCLC), display an ALK-positive FISH pattern as detected using single interference filter sets comprising green (FITC), red (Texas red), and blue (4',6-diamidino-2-phenylindole) as well as dual (red/green) and triple (blue, red, green) band-pass filters. A fusion of the ALK gene is visualized as split orange and green signals, single orange signals, or single orange and single green signals.

Relevant molecular alterations with respect to ALK, ROS1, TrkA, TrkB and TrkC in biological samples derived from cancer patients may be examined and assessed using the same methods as described above, but by modifying the reagents, probes and other materials used in the assays in ways that are appropriate to the target molecular alteration and as can be readily determined by those having ordinary skill in the art.

Other variations of the FISH method known in the art are suitable for evaluating a patient selected in accordance with the methods provided herein.

In some embodiments of the methods provided herein, the cancer is selected from the group consisting of anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, and papillary thyroid cancer.

In some embodiments are provided such methods, wherein the knowledge of the presence of the one or more molecular alterations is obtained from an assay performed simultaneously on a plurality of biological samples. In some embodiments, the plurality of biological samples may be assayed in a multitest platform.

As used herein, the term "multitest platform" is intended to encompass any suitable means to contain one or more reaction mixtures, suspensions, or detection reactions. As such, the outcomes of a number of screening events can be assembled onto one surface, resulting in a "multitest platform" having, or consisting of multiple elements or parts to do more than one experiment simultaneously. It is intended that the term "multitest platform" encompasses protein chips, microtiter plates, multi-well plates, microcards, test tubes, petri plates, trays, slides, and the like. In some embodiments, multiplexing can further include simultaneously conducting a plurality of screening events in each of a plurality of separate biological samples. For example, the number of biological samples analyzed can be based on the number of spots on a slide and the number of tests conducted in each spot. In another example, the number of biological samples analyzed can be based on the number of wells in a multi-well plate and the number of tests conducted in each well. For example, 6-well, 12-well, 24-well, 48-well, 96-well, 384-well, 1536-well or 3456-well microtiter plates can be useful in the presently disclosed methods, although it will be appreciated by those in the art, not each microtiter well need contain an individual biological sample. Depending on the size of the microtiter plate and the number of the individual biological samples in each well, very high numbers of tests can be run simultaneously.

In some embodiments are provided such methods, wherein the plurality of biological samples includes at least 6, 12, 24, 48, 96, 200, 384, 400, 500, 1000, 1250, 1500, or 3000 samples, including increments therein.

In some embodiments are provided such methods, wherein the one or more molecular alterations is selected from a genetic mutation, a gene amplification, a gene rearrangement, a single-nucleotide variation (SNV), a deletion, an insertion, an InDel mutation, one or more single nucleotide point mutations (SNPs), an epigenetic alteration, a splicing variant, an RNA/protein overexpression, and an aberrant RNA/protein expression. In some embodiments are provided such methods, wherein the genetic alteration includes an insertion of a heterologous nucleic acid sequence within a coding sequence of a biomarker gene. In some embodiments are provided such methods, wherein the insertion forms a chimeric nucleic acid sequence that encodes a fusion peptide.

In some embodiments are provided such methods, wherein the acquiring knowledge of the one or more molecular alterations further comprises determining a nucleic acid sequence and/or an amino acid sequence comprising the one or more molecular alterations. In some embodiments, the nucleic acid sequence comprising the one or more molecular alterations from a selected cancer patient tumor is sequenced. In some embodiments, the sequence is determined by a next generation sequencing method.

Implementations of the methods according to this and other aspects of the present disclosure can include one or more of the following features. In some embodiments, the assay includes one or more antibodies that bind to at least two, three, four, or all of ALK, ROS1, TrkA, TrkB and TrkC biomarkers. In some embodiments, the one or more molecular alterations detected in the biological sample involve at least two, at least three, or at least four of the biomarkers. In some embodiments, the knowledge of the presence of the one or more molecular alterations in the biological sample is acquired from an assay that includes contacting the biological sample with one or more antibodies or fragments thereof that are specific for the biomarkers. In some embodiments, the specific antibodies are monoclonal antibodies. In some embodiments, the specific antibodies include at least one of D5F30, D4D50, C17F1®, and combinations thereof. In some embodiments, the biological sample is contacted with one or more of the specific antibodies simultaneously. In some embodiments, the biological sample is sequentially contacted with the specific antibodies. In some embodiments, the one or more molecular alterations results in elevated expression of one or more of the ALK, ROS1, TrkA, TrkB, and TrkC biomarkers. In some embodiments, the knowledge of the one or more molecular alterations is acquired from an assay wherein determining whether the expression of one or more biomarker is elevated includes: (a) determining the expression level of the one or more biomarkers in the biological sample; and (b) comparing the determined expression level to a reference expression level.

In some embodiments, the pharmaceutical compositions comprise a physical admixture of the various ingredients in solid, liquid, or gelcap form. Other embodiments comprise at least two separated ingredients in a single dosage unit or dosage form, such as, for example, a two- or three-layer tablet in which at least two active ingredients are located in separate layers or regions of the tablet, optionally separated by a third material, such as, for example, a sugar layer or other inert barrier to prevent contact between the first two ingredients. In other embodiments, two or more active ingredients are separately formulated into individual dosage units, which are then packaged together for ease of administration. One embodiment comprises a package containing a plurality of individual dosage units. This embodiment may, for example, comprise a blister package. In one embodiment of a blister package, multiple blister-packed dosage units are present on a single sheet, and those units that are to be administered together are packaged in the same or adjacent blisters of the blister pack. Alternatively, any other packaging can be used in which two active ingredients are packaged together for concurrent or sequential use.

In some embodiments, the methods relate to the use of any of the compounds as described herein, or a pharmaceutically acceptable salt thereof, in the manufacture of a medicament for the treatment of abnormal cell growth in a mammal. The present disclosure further relates to the use of any of the compounds as described herein, or a pharmaceutically acceptable salt thereof, in the manufacture of a medicament for the treatment of abnormal cell growth in a mammal wherein the abnormal cell growth is cancerous or non-cancerous. In some embodiments, the abnormal cell growth is cancerous. In another embodiment, the abnormal cell growth is non-cancerous.

In some embodiments, a pharmaceutical composition comprising the first agent and/or the second agent further comprises at least one pharmaceutically acceptable carrier. The pharmaceutically acceptable carrier may comprise a conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

The agents of the present disclosure may be formulated into pharmaceutical compositions as described below in any pharmaceutical form recognizable to the skilled artisan as being suitable. Pharmaceutical compositions of the disclosure comprise a therapeutically effective amount of at least one compound provided herein and an inert, pharmaceutically acceptable carrier or diluent.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a salt of a compound of the present disclosure may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present disclosure is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present disclosure may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the disclosure to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present disclosure may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds of the present disclosure may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5 W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used.

Further, the pharmaceutical composition may be incorporated into a skin patch for delivery of the drug directly onto the skin.

It will be appreciated that the actual dosages of the agents of this disclosure will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment optionally repeated at appropriate intervals.

Additionally, the pharmaceutically acceptable formulations of the present disclosure may contain a compound of the present disclosure, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds provided herein, or salts or solvates thereof, may be administered to a mammal suffering from abnormal cell growth, such as a human, either alone or as part of a pharmaceutically acceptable formulation, once a week, once a day, twice a day, three times a day, or four times a day, or even more frequently.

Those of ordinary skill in the art will understand that with respect to the compounds of the present disclosure, the particular pharmaceutical formulation, the dosage, and the number of doses given per day to a mammal requiring such treatment, are all choices within the knowledge of one of ordinary skill in the art and can be determined without undue experimentation.

Administration of the compounds provided herein may be effected by any method that enables delivery of the compounds to the site of action. These methods include oral routes, intraduodenal routes, parenteral injection (including intravenous, subcutaneous, intramuscular, intravascular or infusion), topical, and rectal administration. Bolus doses can be used, or infusions over a period of 1, 2, 3, 4, 5, 10, 15, 20, 30, 60, 90, 120 or more minutes, or any intermediate time period can also be used, as can infusions lasting 3, 4, 5, 6, 7, 8, 9, 10, 12, 14 16, 20, 24 or more hours or lasting for 1-7 days or more. Infusions can be administered by drip, continuous infusion, infusion pump, metering pump, depot formulation, or any other suitable means.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian patients to be treated; each unit containing a predetermined quantity of active compound calculated to produce the desired therapeutic effect in association with the required pharmaceutical carrier. The specification for the dosage unit forms of the present disclosure are dictated by and directly dependent on (a) the unique characteristics of the active agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

It is to be noted that dosage values may vary with the type and severity of the condition to be alleviated, and may include single or multiple doses. It is to be further understood that for any particular patient, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings provided herein.

In some embodiments, the methods disclosed herein are useful for the treatment of cancers including but not limited to cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

In some embodiments are provided methods disclosed herein wherein the second agent used in combination with the first agent described herein comprises an MEK inhibitor or an ERK inhibitor. In some embodiments, the second agent comprises an MEK inhibitor. Illustrative MEK inhibitors include, but are not limited to, PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. In some embodiments, the second agent comprises an ERK inhibitor. Illustrative ERK inhibitors include, but are not limited to, TG-02, MK-8353, ulixertinib, HE-3235, AEZS-134, AEZS-136, and IDN-5491.

In some embodiments are provided methods disclosed herein wherein the second agent used in combination with the first agent described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKC-beta inhibitors, COX-2 (cyclooxygenase II) inhibitors, integrins (alpha-v/beta-3), MMP-2 (matrix-metalloproteinase 2) inhibitors, and MMP-9 (matrix-metalloprotienase 9) inhibitors. Preferred anti-angiogenesis agents include sunitinib (Sutent®), bevacizumab (Avastin®), axitinib (AG 13736), SU 14813 (Pfizer), and AG 13958 (Pfizer).

Additional anti-angiogenesis agents include vatalanib (CGP 79787), Sorafenib (Nexavar®), pegaptanib octasodium (Macugen®), vandetanib (Zactima®), PF-0337210 (Pfizer), SU 14843 (Pfizer), AZD 2171 (AstraZeneca), ranibizumab (Lucentis®), Neovastat® (AE 941), tetrathiomolybdata (Coprexa®), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex®) and UCN 01 (Kyowa Hakko).

Other examples of anti-angiogenesis agents which can be used in conjunction with one or more pharmaceutical compositions described herein include celecoxib (Celebrex®), parecoxib (Dynastat®), deracoxib (SC 59046), lumiracoxib (Preige®), valdecoxib (Bextra®), rofecoxib (Vioxx®), iguratimod (Careram®), IP 751 (Invedus), SC-58125 (Pharmacia) and etoricoxib (Arcoxia®).

Other anti-angiogenesis agents include exisulind (Aptosyn®), salsalate (Amigesic®), diflunisal (Dolobid®), ibuprofen (Motrin®), ketoprofen (Orudis®) nabumetone (Relafen®), piroxicam (Feldene®), naproxen (Aleve®, Naprosyn®) diclofenac (Voltaren®), indomethacin (Indocin®), sulindac tolmetin (Tolectin®), etodolac (Lodine®), ketorolac (Toradol®), and oxaprozin (Daypro®).

Other anti-angiogenesis agents include ABT 510 (Abbott), apratastat (TMI 005), AZD 8955 (AstraZeneca), incyclinide (Metastat®), and PCK 3145 (Procyon).

Other anti-angiogenesis agents include acitretin (Neotigason®), plitidepsin (Aplidine®), cilengtide (EMD 121974), combretastatin A4 (CA4P), fenretinide (4 HPR), halofuginone (Tempostatin®), Panzem® (2-methoxyestradiol), PF-03446962 (Pfizer), rebimastat (BMS 275291), catumaxomab (Removab®), lenalidomide (Revlimid®) squalamine (EVIZON®), thalidomide (Thalomid®), Ukrain® (NSC 631570), Vitaxin® (MEDI 522), and zoledronic acid (Zometa®).

In some embodiments are provided methods disclosed herein wherein the second agent used in combination with the first agent described herein is a so-called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, ALK inhibitors, ROS1 inhibitors, TrkA inhibitors, TrkB inhibitors, TrkC inhibitors, farnesyl protein transferase inhibitors, EGF inhibitor, ErbB-1 (EGFR) inhibitors, ErbB-2 inhibitors, pan erb inhibitors, IGF1R inhibitors, MEK inhibitors, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Among signal transduction inhibitors that may be used include gefitinib (Iressa®), cetuximab (Erbitux®), erlotinib (Tarceva®), trastuzumab (Herceptin®), sunitinib (Sutent®) imatinib (Gleevec®), and PD325901 (Pfizer).

Additional examples of signal transduction inhibitors which may be used include BMS 214662 (Bristol-Myers Squibb), lonafarnib (Sarasar®), pelitrexol (AG 2037), matuzumab (EMD 7200), nimotuzumab (TheraClM h-R3®), panitumumab (Vectibix®), Vandetanib (Zactima®), pazopanib (SB 786034), ALT 110 (Alteris Therapeutics), BIBW 2992 (Boehringer Ingelheim), and Cervene® (TP 38).

Other examples of signal transduction inhibitors that may be used include PF-2341066 (Pfizer), PF-299804 (Pfizer), canertinib (CI 1033), pertuzumab (Omnitarg®), Lapatinib (Tycerb®), pelitinib (EKB 569), miltefosine (Miltefosin®), BMS 599626 (Bristol-Myers Squibb), Lapuleucel-T (Neuvenge®), NeuVax® (E75 cancer vaccine), Osidem® (IDM 1), mubritinib (TAK-165), CP-724,714 (Pfizer), panitumumab (Vectibix®), lapatinib (Tycerb®), PF-299804 (Pfizer), pelitinib (EKB 569), and pertuzumab (Omnitarg®).

Other examples of signal transduction inhibitors that may be used include ARRY 142886 (Array Biopharm), everolimus (Certican®), zotarolimus (Endeavor®), temsirolimus (Torisel®), AP 23573 (ARIAD), and VX 680 (Vertex).

Other signal transduction inhibitors that may be used include XL 647 (Exelixis), sorafenib (Nexavar®), LE-AON (Georgetown University), and GI-4000 (Globelmmune).

Other signal transduction inhibitors that may be used include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), AG 024322 (Pfizer), LOX0-101 (Loxo Oncology), crizotinib, ceritinib, trametinib, PD0325901, selumetinib, cobimetinib, refametinib, pimasertib, binimetinib, AZD8330, RO4987655, RO5126766, WX-554, E6201, GDC-0623, and TAK-733.

Other signal transduction inhibitors that may be used include trametinib, PD0325901, selumetinib, cobimetinib, refametinib, pimasertib, binimetinib, AZD8330, RO4987655, RO5126766, WX-554, E6201, GDC-0623, and TAK-733.

Other signal transduction inhibitors that may be used include trametinib, selumetinib, cobimetinib, refametinib, pimasertib, and binimetinib. A signal transduction inhibitor that may be used includes trametinib. A signal transduction inhibitor that may be used includes, selumetinib. A signal transduction inhibitor that may be used includes cobimetinib. A signal transduction inhibitor that may be used includes refametinib. A signal transduction inhibitor that may be used includes pimasertib. A signal transduction inhibitor that may be used includes binimetinib.

In some embodiments, the second agent is selected from are classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents that may be used include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Examples of classical antineoplastic agents that may be used include, but are not limited to, suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HC1 (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, paclitaxel, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In some embodiments, the second agent is selected from dihydrofolate reductase inhibitors. Examples of dihydrofolate reductase inhibitors that may be used include, but are not limited to, methotrexate and NeuTrexin (trimetrexate), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda®), cytosine arabinoside, Gemzar® (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KUDOS Pharmaceuticals) and GPI 18180 (Guilford Pharm Inc) and combinations thereof.

Other examples of classical antineoplastic cytotoxic agents that may be used include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta®), DMXAA (Antisoma), ibandronic acid, L-asparaginase, pegaspargase (Oncaspar®), Efaproxiral (Efaproxyn®—radiation therapy)), bexarotene (Targretin®), Tesmilifene (DPPE—enhances efficacy of cytotoxics)), Theratope® (Biomira), Tretinoin (Vesanoid®), tirapazamine (Trizaone®), motexafin gadolinium (Xcytrin®) Cotara® (mAb), and NBI-3001 (Protox Therapeutics), polyglutamate-paclitaxel (Xyotax®) and combinations thereof.

Further examples of classical antineoplastic agents that may be used include, but are not limited to, as Advexin (ING 201), TNFerade (GeneVec, one or more compounds which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

In some embodiments, the methods disclosed herein comprise administering to the patient a combination further comprising one or more additional agents. The one or more additional agents may be independently selected from the anti-angiogenesis agents described herein, the so-called signal transduction inhibitors described herein, the classical antineoplastic agents described herein, and the dihydrofolate reductase inhibitors described herein.

As will be understood by one skilled in the art, for any and all purposes, such as in terms of providing a written description, all ranges provided herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Headings, e.g., (a), (b), (i) etc., are presented merely for ease of reading the specification and claims. The use of headings in the specification or claims does not require the steps or elements be performed in alphabetical or numerical order or the order in which they are presented.

The example herein is provided to illustrate advantages of the present technology and to further assist a person of ordinary skill in the art with using the present technology. The example herein is also presented in order to more fully illustrate the preferred aspects of the present technology. The example should in no way be construed as limiting the scope of the present technology, as defined by the appended claims. The example can include or incorporate any of the variations, aspects or aspects of the present technology described above. The variations, aspects or aspects described above may also further each include or incorporate the variations of any or all other variations, aspects or aspects of the present technology.

EXAMPLES

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Example 1: Pharmaceutical Composition Comprising N-[5-(3,5-difluorobenzyl)-1H-indazol-3-yl]-4-(4-methyl-piperazin-1-yl)-2-(tetrahydro-2H-pyran-4-ylamino)-benzamide A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride was prepared as follows.

| Component | Target amount per dosage unit (mg) | Target weight per batch (g) | Actual weight per batch (g) |
|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 222.22 | 222.23 |
| Betaine hydrochloride | 82.00 | 91.11 | 91.11 |
| Isomalt | 124.00 | 137.78 | 137.78 |
| Pregelatinized starch, NF (Starch 1500) | 35.00 | 38.89 | 38.89 |
| Colloidal silicon dioxide | 4.50 | 5.00 | 5.00 |
| Magnesium stearate, NF | 4.50 | 5.00 | 5.00 |
| Total | 450.00 | 500.00 | 500.01 |

N-[5-(3,5-Difluorobenzyl)-1H-indazol-3-yl]-4-(4-methyl-piperazin-1-yl)-2-(tetrahydro-2H-pyran-4-ylamino)-benzamide was screened through a 60-mesh sieve and was transferred to the batch mixing container. The betaine hydrochloride was ground with a mortar and pestle, screened through a 60-mesh sieve and then transferred to the batch mixing container. The mixture of N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride were mixed by hand for about one minute, after which time the pre-gelatinized starch, colloidal silicon dioxide and one-half of the amount of required isomalt were added to the batch container. The resulting mixture was mixed by hand for about one minute. The magnesium stearate and the remaining isomalt were pre-blended through a 40-mesh sieve and then combined with materials in the batch mixing container. The final mixture was blended by hand for approximately 5 minutes.

The resulting mixture was filled into gelatin capsule shells, opaque white, size #00. The body and cap of the capsules were separated, the capsule bodies were placed into a capsule device, ensuring the top of the capsule body was flush with the surface of the filling device by moving the spacer of the device. The powder blend was poured onto the surface of the filling device, volumetrically filling the body of the capsules, and scraping the excess powder evenly until all capsule bodies are filled. The powder was firmly tamped into the shells one time using a tamper. Additional powder blend was added to fill the remainder of the capsule and any excess powder was scraped off. The tamping, filling, and scraping procedures were repeated for each capsule until the desired capsule fill weight was achieved. The filled capsules were collected in a 10-mesh sieve and were de-dusted by agitating them lightly.

The filled capsule weight range acceptance limits were set at 93% to 107%. The average weight of the empty capsule shells was 119.4 mg. The low capsule weight limit was set at (0.93×450 mg)+119.4 mg=538 mg. The high capsule weight limit was set at (1.07×450 mg)+119.4 mg=601 mg. Only those capsules meeting the weight limits were used in subsequent studies.

These capsules are used for concurrent or sequential administration with a separate pharmaceutical composition comprising a second agent. The second agent may be a MEK inhibitor or an ERK inhibitor.

Example 2: Combination Therapy for Patients with Non-Small Cell Lung Cancer

One or more appropriate doses of N-[5-(3,5-difluorobenzyl)-1H-indazol-3-yl]-4-(4-methyl-piperazin-1-yl)-2-(tetrahydro-2H-pyran-4-ylamino)-benzamide and a second agent are administered to a human patient for the treatment of non-small cell lung cancer. Expected results from treatment with the combination, include (1) reduction of the size of a cancer tumor, (2) inhibition (that is, slowing to some extent, preferably stopping) of cancer tumor metastasis, (3) inhibition to some extent (that is, slowing to some extent, preferably stopping) of cancer tumor growth, and/or, (4) relief to some extent (or, preferably, eliminating) one or more symptoms associated with the cancer. The second agent may be a MEK inhibitor or an ERK inhibitor. Examples of MEK inhibitors include, but are not limited to, PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. Examples of ERK inhibitors include, but are not limited to, TG-02, MK-8353, ulixertinib, HE-3235, AEZS-134, AEZS-136, and IDN-5491.

Example 3: Combination Therapy for Patients with Papillary Thyroid Cancer

One or more appropriate doses of N-[5-(3,5-difluorobenzyl)-1H-indazol-3-yl]-4-(4-methyl-piperazin-1-yl)-2-(tetrahydro-2H-pyran-4-ylamino)-benzamide and a second agent are administered to a human patient for the treatment of papillary thyroid cancer. Expected results from treatment with the combination, include (1) reduction of the size of a cancer tumor, (2) inhibition (that is, slowing to some extent, preferably stopping) of cancer tumor metastasis, (3) inhibition to some extent (that is, slowing to some extent, preferably stopping) of cancer tumor growth, and/or, (4) relief to some extent (or, preferably, eliminating) one or more symptoms associated with the cancer. The second agent may be a MEK inhibitor or an ERK inhibitor. Examples of MEK inhibitors include, but are not limited to, PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. Examples of ERK inhibitors include, but are not limited to, TG-02, MK-8353, ulixertinib, HE-3235, AEZS-134, AEZS-136, and IDN-5491.

Example 4: Combination Therapy for Patients with Neuroblastoma

One or more appropriate doses of N-[5-(3,5-difluorobenzyl)-1H-indazol-3-yl]-4-(4-methyl-piperazin-1-yl)-2-(tetrahydro-2H-pyran-4-ylamino)-benzamide and a second agent are administered to a human patient for the treatment of neuroblastoma. Expected results from treatment with the combination, include (1) reduction of the size of a cancer tumor, (2) inhibition (that is, slowing to some extent, preferably stopping) of cancer tumor metastasis, (3) inhibition to some extent (that is, slowing to some extent, preferably stopping) of cancer tumor growth, and/or, (4) relief to some extent (or, preferably, eliminating) one or more symptoms associated with the cancer. The second agent may be a MEK inhibitor or an ERK inhibitor. Examples of MEK inhibitors include, but are not limited to, PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. Examples of ERK inhibitors include, but are not limited to, TG-02, MK-8353, ulixertinib, HE-3235, AEZS-134, AEZS-136, and IDN-5491.

Example 5: Combination Therapy for Patients with Pancreatic Cancer

One or more appropriate doses of N-[5-(3,5-difluorobenzyl)-1H-indazol-3-yl]-4-(4-methyl-piperazin-1-yl)-2-(tetrahydro-2H-pyran-4-ylamino)-benzamide and a second agent are administered to a human patient for the treatment of pancreatic cancer. Expected results from treatment with the combination, include (1) reduction of the size of a cancer tumor, (2) inhibition (that is, slowing to some extent, preferably stopping) of cancer tumor metastasis, (3) inhibition to some extent (that is, slowing to some extent, preferably stopping) of cancer tumor growth, and/or, (4) relief to some extent (or, preferably, eliminating) one or more symptoms associated with the cancer. The second agent may be a MEK inhibitor or an ERK inhibitor. Examples of MEK inhibitors include, but are not limited to, PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. Examples of ERK inhibitors include, but are not limited to, TG-02, MK-8353, ulixertinib, HE-3235, AEZS-134, AEZS-136, and IDN-5491.

Example 6: Combination Therapy for Patients with Melanoma

One or more appropriate doses of N-[5-(3,5-difluorobenzyl)-1H-indazol-3-yl]-4-(4-methyl-piperazin-1-yl)-2-(tetrahydro-2H-pyran-4-ylamino)-benzamide and a second agent are administered to a human patient for the treatment of melanoma. Expected results from treatment with the combination, include (1) reduction of the size of a cancer tumor, (2) inhibition (that is, slowing to some extent, preferably stopping) of cancer tumor metastasis, (3) inhibition to some extent (that is, slowing to some extent, preferably stopping) of cancer tumor growth, and/or, (4) relief to some extent (or, preferably, eliminating) one or more symptoms associated with the cancer. The second agent may be a MEK inhibitor or an ERK inhibitor. Examples of MEK inhibitors include, but are not limited to, PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. Examples of ERK inhibitors include, but are not limited to, TG-02, MK-8353, ulixertinib, HE-3235, AEZS-134, AEZS-136, and IDN-5491.

Example 7: Combination Therapy for Patients with Colorectal Cancer

One or more appropriate doses of N-[5-(3,5-difluorobenzyl)-1H-indazol-3-yl]-4-(4-methyl-piperazin-1-yl)-2-(tetrahydro-2H-pyran-4-ylamino)-benzamide and a second agent are administered to a human patient for the treatment of colorectal cancer. Expected results from treatment with the combination, include (1) reduction of the size of a cancer tumor, (2) inhibition (that is, slowing to some extent, preferably stopping) of cancer tumor metastasis, (3) inhibition to some extent (that is, slowing to some extent, preferably stopping) of cancer tumor growth, and/or, (4) relief to some extent (or, preferably, eliminating) one or more symptoms associated with the cancer. The second agent may be a MEK inhibitor or an ERK inhibitor. Examples of MEK inhibitors include, but are not limited to, PD0325901, selumetinib, cobimetinib, refametinib, trametinib, pimasertib, binimetinib, AZD8330, RO4987655, RO5126766, WX-554, E-6201, GDC-0623, TAK-733, RG-7304, CKBP-002, RDEA-436, sorafenib, PD-184352, GSK-2091976A, and AS-703988. Examples of ERK inhibitors include, but are not limited to, TG-02, MK-8353, ulixertinib, HE-3235, AEZS-134, AEZS-136, and IDN-5491.

Example 8: Generation of Ba/F3-TPM3-TrkA-G959R Cell Lines

This Example describes studies performed to generate transgenic Ba/F3 cells expressing a TPM3-TrkA-G595R fusion protein. A cDNA encoding TPM3-TrkA-G595R fusion was cloned from entrectinib-resistant cells by a PCR-based technique and subsequently inserted into a lentiviral vector pVL-EF1a-MCS-IRES-Puro (BioSettia, San Diego, Calif.). After confirmation of the cDNA inserts by direct sequencing, vesicular stomatitis virus GP (VSVG)-pseudo-typed lentiviruses containing the TPM3-TrkA-G595R cDNA were transduced into the murine IL-3 dependent pro-B cell Ba/F3 at different multiplicity of infections (MOIs) with 8 µg/mL of polybrene (EMD Millipore). The transduced Ba/F3 cells were selected in the murine IL-3 containing RPMI media supplemented with 10% FBS and 1 µg/mL of puromycin for two weeks. The stable cell pools were further selected in RPMI media (GIBCO®) supplemented with 10% FBS (fetal bovine serum) and without murine IL-3 for 4 weeks.

Example 9: Effect of Treatment with Entrectinib (RXDX-101) on Ba/F3 Cells Expressing TPM3-TrkA or TPM3-TrkA-G595R Mutation Five to 10 million Ba/F3 cells expressing either TPM3-TrkA or TPM3-TrkA-G595R were incubated with different concentrations of entrectinib (RXDX-101) for 2 hours in a 5% $CO_2$ incubator. The cells were washed twice with cold phosphate-buffered saline (PBS) (1×) and were then resuspended in 1×RIPA buffer with protease and phosphatase inhibitor cocktails (EMDMillipore) and the resulting mixture was rocked for 30 minutes at 4° C. The resulting lysates were clarified by centrifuging (10,000×g) at 4° C. for 10 minutes. The resulting supernatants were saved for Western Blot analysis. 20-40 µg of the resulting proteins were separated by SDS-PAGE electrophoresis and transferred to polyvinylidene difluoride (PVDF) membranes. The resulting membranes were blotted with the following antibodies (obtained from Cell Signalling unless otherwise stated) according to the procedures described in the respective manuals: phospho-TrkA-Y490, phospho-TrkA-Y785, pan-Trk, PLCY1, phospho-PLCY1-Y783, MEK1/2, phospho-MEK1/2 (S217/S221), β-actin. The resulting bands were developed with ECL reagents (Amersham) and the images were captured using ChemiDoc imager (Bio-Rad). The results of the Western Blot analysis are shown in FIG. 1 and demonstrate that p-MEK1/2 (Ser217/221) and total MEK1/2 are upregulated in the Ba/F3 cells expressing TPM3-TrkA-G595R versus Ba/F3 cells expressing wild-type TPM3-TrkA.

Figure 2:
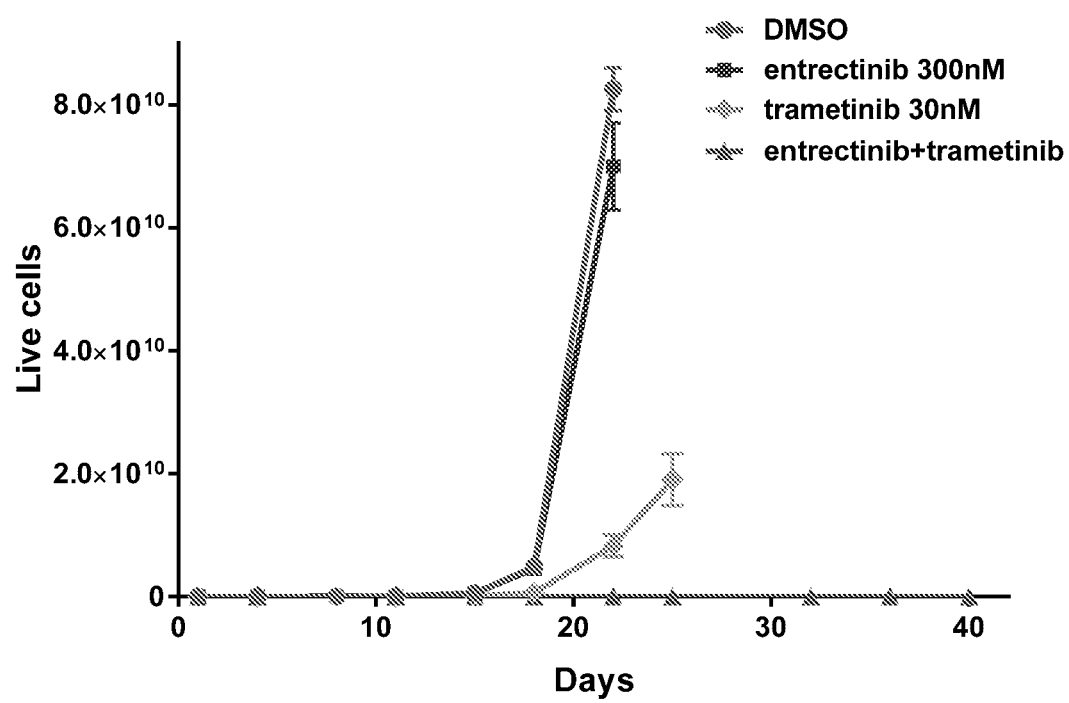
FIG. 2 is a plot of the growth of live cells from Example 10, demonstrating that Ba/F3 cells expressing TPM3-TrkA-G595R that are treated with the combination of entrectinib (300 nM) and trametinib (30 nM) displayed significant inhibition of growth (up to 40 days) compared to the cells that were untreated (DMSO), those treated with entrectinib (300 nM) alone and those treated with trametinib (30 nM) alone.

Example 10: In Vitro Activities of Entrectinib (RXDX-101), Trametinib, and the Combination of Entrectinib and Trametinib on the Inhibition of Growth of Ba/F3 Cell Lines Expressing TPM3-TrkA-G959R The effects on the growth of a Ba/F3 cell line expressing TPM3-TrkA-G959R resulting from treatment with entrectinib (RXDX-101), trametinib, and the combination of entrectinib and trametinib were measured. Approximately one million Ba/F3 cells expressing TPM3-TrkA-G959R per well were seeded in 6-well plates in 5 mL media. To the wells were added one of the following from 1000× stocks in DMSO: (a) no inhibitor (dimethylsulfoxide (DMSO) alone as control), (b) entrectinib (RXDX-101) at a concentration of about 300 nM, (c) trametinib at a concentration of about 30 nM, or (d) a combination of entrectinib (RXDX-101) at a concentration of 300 nM and trametinib at a concentration of 30 nM. The cells in each respective well were counted every 3 to 4 days using Countess™ cell counter (Invitrogen, Carlsbad, Calif.) in the presence of Trypan Blue (Invitrogen, Carlsbad, Calif.). For those wells that contained at least 1 million live cells on the day the cells in each well were counter, the media containing those cells were diluted at 1:10 with fresh growth media containing the same respective concentrations of entrectinib, trametinib or the combination of entrectinib and trametinib. The wells that contained fewer than 1 million live cells on the day the cells in each well were counted went unchanged. The results of the study are shown in FIG. 2, which demonstrates that the cells treated with the combination of entrectinib (300 nM) and trametinib (30 nM) displayed significant growth inhibition (up to 40 days) compared to the cells in wells containing no compound (DMSO control) and those containing entrectinib (300 nM) alone and trametinib (30 nM) alone.

Figure 3:
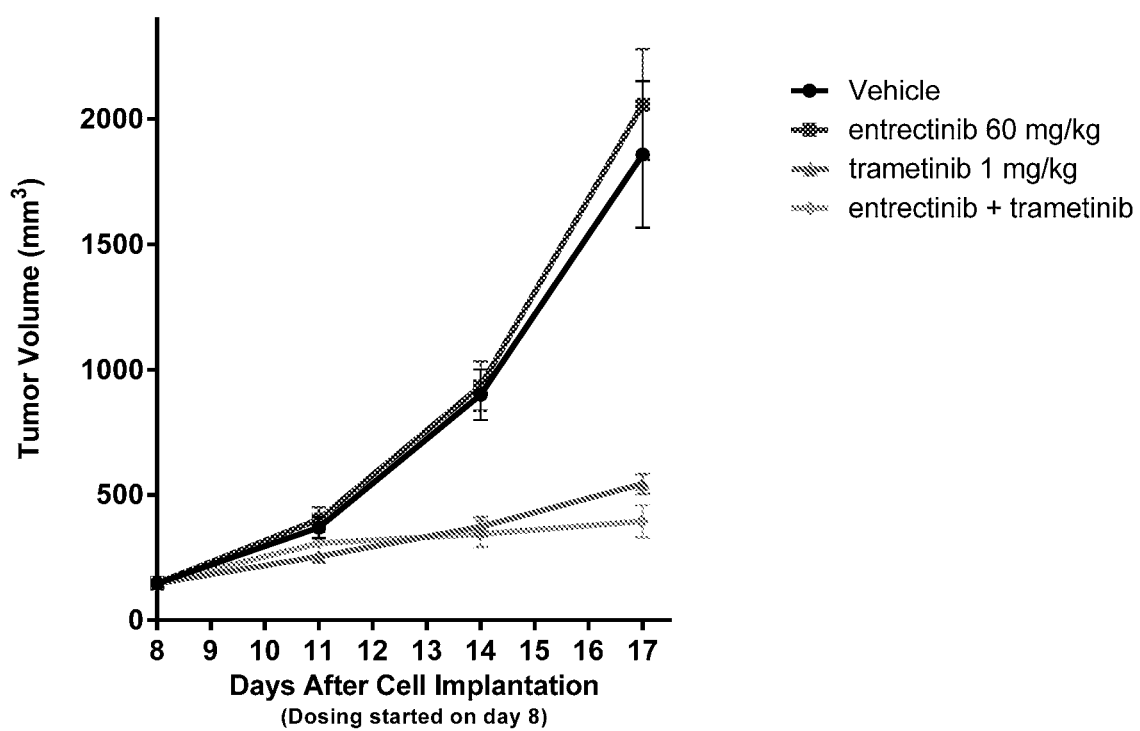
FIG. 3 is a plot of the results from Example 11, which demonstrates that the growth of tumors in mice implanted with cells expressing TPM3-TrkA-G595R was reduced in those mice to which a combination of entrectinib (RXDX-101) (60 mg/kg) and trametinib (1 mg/kg) was administered versus tumor growth in those mice in the control group (Vehicle), those mice treated with entrectinib (60 mg/kg) alone, and those mice treated with tremetinib (1 mg/kg) alone.

Example 11: In Vivo Study of Mice Implanted with Cells Expressing TPM3-TrkA-G595R Following Administration of Entrectinib (RXDX-101), Trametinib, or a Combination of Entrectinib and Trametinib Athymic nu/nu mice, 6-7 weeks old, female mice were implanted subcutaneously (right flank) with 2 million KM-12 TPM3-NTRK1 G595R cells/mouse. Animals were randomized once the mean tumor volume reached ~150 $mm^3$. Animals received a total of 10 doses of Vehicle, 60 mg/kg entrectinib, 1 mg/kg trametinib, and combination of entrectinib (60 mg/kg)+trametinib (1 mg/kg), p.o. q.d. All treatments were tolerable. The results are shown in FIG. 3, which demonstrates that the growth of tumors in mice implanted with cells expressing TPM3-TrkA-G595R was reduced in those mice to which a combination of entrectinib (RXDX-101) (60 mg/kg) and trametinib (1 mg/kg) were administered versus tumor growth in those mice in the control group (Vehicle), those mice treated with entrectinib (60 mg/kg) alone, and those mice treated with trametinib (1 mg/kg) alone.

Good manufacture practice (GMP)-quality entrectinib (RXDX-101), was synthesized at Ignyta (Lot #: CA15-919, fill date 12/13/15). The entrectinib in vivo oral dosing solution was made by suspending entrectinib in a solution of 0.5% methyl cellulose (Lot #: 147255, M352-500, Fisher) and 1% Tween 80 (Lot #: MKB58228V, P4780-100ML, Sigma) at a concentration of 5 mg/mL. Trametinib in vivo oral dosing solution was made by dissolving trametinib in a solution of DMSO (Lot #: SHBG1596V, D8418-100ML, Sigma), PEG 400 (Lot #: MKBX3961V, 202398-500G, Sigma), Tween 80 (Lot #: MKB58228V, P4780-100ML, Sigma) and water. The final concentration of trametinib was 0.1 mg/mL and the amounts of each component in the resulting solution were 3.3% DMSO, 16.7% PEG 400, 15% Tween 80 and 65% water, with the water being added just prior to dosing.

After randomization, all animals were dosed p.o. q.d. with solutions of (a) entrectinib vehicle, (b) entrectinib (5 mg/mL), (c) trametinib (0.1 mg/mL), or (d) a combination of entrectinib (5 mg/mL) and trametinib (0.1 mg/mL), at a dosing volume of about 10 mL/kg body weight.

Athymic nu/nu female mice between 6-7 weeks of age were ordered from Charles River. Animals were allowed to acclimate 3 days prior to the start of the study (e.g., cell implantation). Animals were housed in irradiated, individual HEPA ventilated cages (Innocage® IVC, Innovive USA) on a 12-hour light-dark cycle at 68-79° F. and 30-70% humidity. Animals were provided with irradiated chow (Teklad 2920X) and acidified drinking water (Innovive) ad libitum as per the animal care and use protocol established at Explora Biolabs (Ignyta ACUP # EB15-050). Animals were identified by uniquely numbered ear-tags.

KM12 cells were cultured, harvested, and suspended in 1:1 FBS free culture media:martigel at a concentration of 10 million cells/mL. Cells were implanted under the skin on the right flank of each mouse on day 0. The implantation volume was 200 µL/mouse. Tumors grew until the mean tumor volume reached approximately 130 mm$^3$. On day 8 mice were randomized into 6 treatment groups (10 mice/group) and treatment began. Animals were treated p.o. q.d. with (a) vehicle (0.5% methyl cellulose and 1% Tween 80), (b) entrectinib (60 mg/kg), (c) 1 mg/kg trametinib, or (d) a combination of entrectinib (60 mg/kg) and trametinib (1 mg/kg). The final treatment for all groups was administered on day 17, for a total of 10 doses. The final tumor and body weight measurements were taken on the final day of dosing, day 17.

Tumors measurements and body weights were collected 2×/week over the duration of the study. Tumor growth was assessed by caliper and tumor volumes were calculated using the equation (1). Animals with tumor volumes >2,000 mm$^3$ were removed from study.

$$\text{Volume (mm}^3\text{)} = [\text{length (mm)} \times \text{width (mm)} \times \text{width (mm)}]/2 \quad (1)$$

Body weights were collected using a laboratory scale. Toxicity was evaluated based on body weight loss. Animals losing <15% of their body weight were removed from the study.

The percentage of tumor growth inhibition (% TGI) was calculated for each treatment group at each tumor measurement. The % TGI values were calculated using equation (2) below, where $TV_{vehicle}$ is the tumor volume for the vehicle-treated animals at a specified time point, $TV_{initial}$ is the initial tumor volume at the start of the treatment and $TV_{treatment}$ is the tumor volume of the treatment group at a specified end-point time. Differences in tumor volumes were assessed by ANOVA using GraphPad Prism (version 6.07, GraphPad Software, Inc.).

$$\% \text{ TGI} = [(TV_{vehicle} - TV_{treatment})/(TV_{vehicle} - TV_{initial})] \times 100$$

A summary table of the average tumor volume for each group, for each measurement day is shown in Table 1. The % TGI for each day was calculated as described above and these data are summarized in Table 2. Evaluation of significance by two-way ANOVA (Prism) was limited out to day 14 due to one death in the entrectinib+trametinib group. Body weight data for this study shows that this death is likely due to toxicity induced by trametinib. Analysis showed that by day 14 only the trametinib alone groups was significantly different from vehicle (p<0.05, two-way ANOVA, Prism). The same was found if the entrectinib+trametinib group was omitted and the analysis was carried out to day 17. Statistical evaluation of each treatment group versus vehicle for each measurement day (i.e., day 11, 14 and 17) was also evaluated by one-way ANOVA. Differences were found between vehicle and trametinib alone and between vehicle and entrectinib+trametinib for days 14 and 17. All groups were found to be different from vehicle on day 17 (p<0.05, one-way ANOVA, Prism). Body weights remained stable throughout the study for the vehicle and entrectinib alone groups. Toxicity was observed for any animals receiving trametinib. One death was observed in the entrectinib+trametinib group and Body weight data for this animal showed a decline is weight prior to death.

TABLE 1

Average tumor volume for each treatment group on each day measured.

| | | Days After Cell Implantation | | | |
|---|---|---|---|---|---|
| | | 8 | 11 | 14 | 17 |
| Treatment Group | Vehicle | 147.1 | 369.7 | 900.3 | 1858.9 |
| | Entrectinib | 148.2 | 403.2 | 934.5 | 2057.8 |
| | Trametinib | 146.7 | 254.8 | 373.1 | 544.9 |
| | Entrectinib + Trametinib | 148.0 | 308.0 | 343.9 | 394.5 |

TABLE 2

Percent tumor growth inhibition (% TGI) for each treatment group on each day measured.

| | | Days After Cell Implantation | | | |
|---|---|---|---|---|---|
| | | 8 | 11 | 14 | 17 |
| Treatment Group | Entrectinib | 100.0 | −15.1 | −4.5 | −11.6 |
| | Trametinib | 100.0 | 51.5 | 70.0 | 76.7 |
| | Entrectinib + Trametinib | 100.0 | 27.8 | 74.0 | 85.6 |

```
                    Sequence Listings human tropomyosin receptor kinase A (TrkA)
Met Leu Arg Gly Gly Arg Arg Gly Gln Leu Gly Trp His Ser Trp Ala
Ala Gly Pro Gly Ser Leu Leu Ala Trp Leu Ile Leu Ala Ser Ala Gly
Ala Ala Pro Cys Pro Asp Ala Cys Cys Pro His Gly Ser Ser Gly Leu
Arg Cys Thr Arg Asp Gly Ala Leu Asp Ser Leu His His Leu Pro Gly
Ala Glu Asn Leu Thr Glu Leu Tyr Ile Glu Asn Gln Gln His Leu Gln
His Leu Glu Leu Arg Asp Leu Arg Gly Leu Gly Glu Leu Arg Asn Leu
Thr Ile Val Lys Ser Gly Leu Arg Phe Val Ala Pro Asp Ala Phe His
Phe Thr Pro Arg Leu Ser Arg Leu Asn Leu Ser Phe Asn Ala Leu Glu
Ser Leu Ser Trp Lys Thr Val Gln Gly Leu Ser Leu Gln Glu Leu Val
Leu Ser Gly Asn Pro Leu His Cys Ser Cys Ala Leu Arg Trp Leu Gln
Arg Trp Glu Glu Glu Gly Leu Gly Gly Val Pro Glu Gln Lys Leu Gln
Cys His Gly Gln Gly Pro Leu Ala His Met Pro Asn Ala Ser Cys Gly
Val Pro Thr Leu Lys Val Gln Val Pro Asn Ala Ser Val Asp Val Gly
Asp Asp Val Leu Leu Arg Cys Gln Val Glu Gly Arg Gly Leu Glu Gln
Ala Gly Trp Ile Leu Thr Glu Leu Glu Gln Ser Ala Thr Val Met Lys
Ser Gly Gly Leu Pro Ser Leu Gly Leu Thr Leu Ala Asn Val Thr Ser
Asp Leu Asn Arg Lys Asn Val Thr Cys Trp Ala Glu Asn Asp Val Gly
Arg Ala Glu Val Ser Val Gln Val Asn Val Ser Phe Pro Ala Ser Val
Gln Leu His Thr Ala Val Glu Met His His Trp Cys Ile Pro Phe Ser
```

-continued

Sequence Listings

Val Asp Gly Gln Pro Ala Pro Ser Leu Arg Trp Leu Phe Asn Gly Ser
Val Leu Asn Glu Thr Ser Phe Ile Phe Thr Glu Phe Leu Glu Pro Ala
Ala Asn Glu Thr Val Arg His Gly Cys Leu Arg Leu Asn Gln Pro Thr
His Val Asn Asn Gly Asn Tyr Thr Leu Leu Ala Ala Asn Pro Phe Gly
Gln Ala Ser Ala Ser Ile Met Ala Ala Phe Met Asp Asn Pro Phe Glu
Phe Asn Pro Glu Asp Pro Ile Pro Val Ser Phe Ser Pro Val Asp Thr
Asn Ser Thr Ser Gly Asp Pro Val Glu Lys Lys Asp Glu Thr Pro Phe
Gly Val Ser Val Ala Val Gly Leu Ala Val Phe Ala Cys Leu Phe Leu
Ser Thr Leu Leu Leu Val Leu Asn Lys Cys Gly Arg Arg Asn Lys Phe
Gly Ile Asn Arg Pro Ala Val Leu Ala Pro Glu Asp Gly Leu Ala Met
Ser Leu His Phe Met Thr Leu Gly Gly Ser Ser Leu Ser Pro Thr Glu
Gly Lys Gly Ser Gly Leu Gln Gly His Ile Ile Glu Asn Pro Gln Tyr
Phe Ser Asp Ala Cys Val His His Ile Lys Arg Arg Asp Ile Val Leu
Lys Trp Glu Leu Gly Glu Gly Ala Phe Gly Lys Val Phe Leu Ala Glu
Cys His Asn Leu Leu Pro Glu Gln Asp Lys Met Leu Val Ala Val Lys
Ala Leu Lys Glu Ala Ser Glu Ser Ala Arg Gln Asp Phe Gln Arg Glu
Ala Glu Leu Leu Thr Met Leu Gln His Gln His Ile Val Arg Phe Phe
Gly Val Cys Thr Glu Gly Arg Pro Leu Leu Met Val Phe Glu Tyr Met
Arg His Gly Asp Leu Asn Arg Phe Leu Arg Ser His Gly Pro Asp Ala
Lys Leu Leu Ala Gly Gly Glu Asp Val Ala Pro Gly Pro Leu Gly Leu
Gly Gln Leu Leu Ala Val Ala Ser Gln Val Ala Ala Gly Met Val Tyr
Leu Ala Gly Leu His Phe Val His Arg Asp Leu Ala Thr Arg Asn Cys
Leu Val Gly Gln Gly Leu Val Val Lys Ile Gly Asp Phe Gly Met Ser
Arg Asp Ile Tyr Ser Thr Asp Tyr Tyr Arg Val Gly Gly Arg Thr Met
Leu Pro Ile Arg Trp Met Pro Pro Glu Ser Ile Leu Tyr Arg Lys Phe
Thr Thr Glu Ser Asp Val Trp Ser Phe Gly Val Val Leu Trp Glu Ile
Phe Thr Tyr Gly Lys Gln Pro Trp Tyr Gln Leu Ser Asn Thr Glu Ala
Ile Asp Cys Ile Thr Gln Gly Arg Glu Leu Glu Arg Pro Arg Ala Cys
Pro Pro Glu Val Tyr Ala Ile Met Arg Gly Cys Trp Gln Arg Glu Pro
Gln Gln Arg His Ser Ile Lys Asp Val His Ala Arg Leu Gln Ala Leu
Ala Gln Ala Pro Pro Val Tyr Leu Asp Val Leu Gly (SEQ ID NO: 1)

human tropomyosin receptor kinase B (TrkB)
Met Ser Ser Trp Ile Arg Trp His Gly Pro Ala Met Ala Arg Leu Trp
Gly Phe Cys Trp Leu Val Val Gly Phe Trp Arg Ala Ala Phe Ala Cys
Pro Thr Ser Cys Lys Cys Ser Ala Ser Arg Ile Trp Cys Ser Asp Pro
Ser Pro Gly Ile Val Ala Phe Pro Arg Leu Glu Pro Asn Ser Val Asp
Pro Glu Asn Ile Thr Glu Ile Phe Ile Ala Asn Gln Lys Arg Leu Glu
Ile Ile Asn Glu Asp Asp Val Glu Ala Tyr Val Gly Leu Arg Asn Leu
Thr Ile Val Asp Ser Gly Leu Lys Phe Val Ala His Lys Ala Phe Leu
Lys Asn Ser Asn Leu Gln His Ile Asn Phe Thr Arg Asn Lys Leu Thr
Ser Leu Ser Arg Lys His Phe Arg His Leu Asp Leu Ser Glu Leu Ile
Leu Val Gly Asn Pro Phe Thr Cys Ser Cys Asp Ile Met Trp Ile Lys
Thr Leu Gln Glu Ala Lys Ser Ser Pro Asp Thr Gln Asp Leu Tyr Cys
Leu Asn Glu Ser Ser Lys Asn Ile Pro Leu Ala Asn Leu Gln Ile Pro
Asn Cys Gly Leu Pro Ser Ala Asn Leu Ala Ala Pro Asn Leu Thr Val
Glu Glu Gly Lys Ser Ile Thr Leu Ser Cys Ser Val Ala Gly Asp Pro
Val Pro Asn Met Tyr Trp Asp Val Gly Asn Leu Val Ser Lys His Met
Asn Glu Thr Ser His Thr Gln Gly Ser Leu Arg Ile Thr Asn Ile Ser
Ser Asp Asp Ser Gly Lys Gln Ile Ser Cys Val Ala Glu Asn Leu Val
Gly Glu Asp Gln Asp Ser Val Asn Leu Thr Val His Phe Ala Pro Thr
Ile Thr Phe Leu Glu Ser Pro Thr Ser Asp His His Trp Cys Ile Pro
Phe Thr Val Lys Gly Asn Pro Lys Pro Ala Leu Gln Trp Phe Tyr Asn
Gly Ala Ile Leu Asn Glu Ser Lys Tyr Ile Cys Thr Lys Ile His Val
Thr Asn His Thr Glu Tyr His Gly Cys Leu Gln Leu Asp Asn Pro Thr
His Met Asn Asn Gly Asp Tyr Thr Leu Ile Ala Lys Asn Glu Tyr Gly
Lys Asp Glu Lys Gln Ile Ser Ala His Phe Met Gly Trp Pro Gly Ile
Asp Asp Gly Ala Asn Pro Asn Tyr Pro Asp Val Ile Tyr Glu Asp Tyr
Gly Thr Ala Ala Asn Asp Ile Gly Asp Thr Thr Asn Arg Ser Asn Glu
Ile Pro Ser Thr Asp Val Thr Asp Lys Thr Gly Arg Glu His Leu Ser
Val Tyr Ala Val Val Val Ile Ala Ser Val Val Gly Phe Cys Leu Leu
Val Met Leu Phe Leu Leu Lys Leu Ala Arg His Ser Lys Phe Gly Met
Lys Asp Phe Ser Trp Phe Gly Phe Gly Lys Val Lys Ser Arg Gln Gly
Val Gly Pro Ala Ser Val Ile Ser Asn Asp Asp Asp Ser Ala Ser Pro
Leu His His Ile Ser Asn Gly Ser Asn Thr Pro Ser Ser Ser Glu Gly
Gly Pro Asp Ala Val Ile Ile Gly Met Thr Lys Ile Pro Val Ile Glu
Asn Pro Gln Tyr Phe Gly Ile Thr Asn Ser Gln Leu Lys Pro Asp Thr
Phe Val Gln His Ile Lys Arg His Asn Ile Val Leu Lys Arg Glu Leu
Gly Glu Gly Ala Phe Gly Lys Val Phe Leu Ala Glu Cys Tyr Asn Leu
Cys Pro Glu Gln Asp Lys Ile Leu Val Ala Val Lys Thr Leu Lys Asp
Ala Ser Asp Asn Ala Arg Lys Asp Phe His Arg Glu Ala Glu Leu Leu
Thr Asn Leu Gln His Glu His Ile Val Lys Phe Tyr Gly Val Cys Val
Glu Gly Asp Pro Leu Ile Met Val Phe Glu Tyr Met Lys His Gly Asp
Leu Asn Lys Phe Leu Arg Ala His Gly Pro Asp Ala Val Leu Met Ala
Glu Gly Asn Pro Pro Thr Glu Leu Thr Gln Ser Gln Met Leu His Ile
Ala Gln Gln Ile Ala Ala Gly Met Val Tyr Leu Ala Ser Gln His Phe
Val His Arg Asp Leu Ala Thr Arg Asn Cys Leu Val Gly Glu Asn Leu

Sequence Listings

```
Leu Val Lys Ile Gly Asp Phe Gly Met Ser Arg Asp Val Tyr Ser Thr
Asp Tyr Tyr Arg Val Gly Gly His Thr Met Leu Pro Ile Arg Trp Met
Pro Pro Glu Ser Ile Met Tyr Arg Lys Phe Thr Thr Glu Ser Asp Val
Trp Ser Leu Gly Val Val Leu Trp Glu Ile Phe Thr Tyr Gly Lys Gln
Pro Trp Tyr Gln Leu Ser Asn Asn Glu Val Ile Glu Cys Ile Thr Gln
Gly Arg Val Leu Gln Arg Pro Arg Thr Cys Pro Gln Glu Val Tyr Glu
Leu Met Leu Gly Cys Trp Gln Arg Glu Pro His Met Arg Lys Asn Ile
Lys Gly Ile His Thr Leu Leu Gln Asn Leu Ala Lys Ala Ser Pro Val
Tyr Leu Asp Ile Leu Gly (SEQ ID NO: 2)
``` human tropomyosin receptor kinase C (TrkC)
```
Met Asp Val Ser Leu Cys Pro Ala Lys Cys Ser Phe Trp Arg Ile Phe
Leu Leu Gly Ser Val Trp Leu Asp Tyr Val Gly Ser Val Leu Ala Cys
Pro Ala Asn Cys Val Cys Ser Lys Thr Glu Ile Asn Cys Arg Arg Pro
Asp Asp Gly Asn Leu Phe Pro Leu Leu Glu Gly Gln Asp Ser Gly Asn
Ser Asn Gly Asn Ala Ser Ile Asn Ile Thr Asp Ile Ser Arg Asn Ile
Thr Ser Ile His Ile Glu Asn Trp Arg Ser Leu His Thr Leu Asn Ala
Val Asp Met Glu Leu Tyr Thr Gly Leu Gln Lys Leu Thr Ile Lys Asn
Ser Gly Leu Arg Ser Ile Gln Pro Arg Ala Phe Ala Lys Asn Pro His
Leu Arg Tyr Ile Asn Leu Ser Ser Asn Arg Leu Thr Thr Leu Ser Trp
Gln Leu Phe Gln Thr Leu Ser Leu Arg Glu Leu Gln Leu Glu Gln Asn
Phe Phe Asn Cys Ser Cys Asp Ile Arg Trp Met Gln Leu Trp Gln Glu
Gln Gly Glu Ala Lys Leu Asn Ser Gln Asn Leu Tyr Cys Ile Asn Ala
Asp Gly Ser Gln Leu Pro Leu Phe Arg Met Asn Ile Ser Gln Cys Asp
Leu Pro Glu Ile Ser Val Ser His Val Asn Leu Thr Val Arg Glu Gly
Asp Asn Ala Val Ile Thr Cys Asn Gly Ser Gly Ser Pro Leu Pro Asp
Val Asp Trp Ile Val Thr Gly Leu Gln Ser Ile Asn Thr His Gln Thr
Asn Leu Asn Trp Thr Asn Val His Ala Ile Asn Leu Thr Leu Val Asn
Val Thr Ser Glu Asp Asn Gly Phe Thr Leu Thr Cys Ile Ala Glu Asn
Val Val Gly Met Ser Asn Ala Ser Val Ala Leu Thr Val Tyr Tyr Pro
Pro Arg Val Val Ser Leu Glu Glu Pro Glu Leu Arg Leu Glu His Cys
Ile Glu Phe Val Val Arg Gly Asn Pro Pro Pro Thr Leu His Trp Leu
His Asn Gly Gln Pro Leu Arg Glu Ser Lys Ile Ile His Val Glu Tyr
Tyr Gln Glu Gly Glu Ile Ser Glu Gly Cys Leu Leu Phe Asn Lys Pro
Thr His Tyr Asn Asn Gly Asn Tyr Thr Leu Ile Ala Lys Asn Pro Leu
Gly Thr Ala Asn Gln Thr Ile Asn Gly His Phe Leu Lys Glu Pro Phe
Pro Glu Ser Thr Asp Asn Phe Ile Leu Phe Asp Glu Val Ser Pro Thr
Pro Pro Ile Thr Val Thr His Lys Pro Glu Glu Asp Thr Phe Gly Val
Ser Ile Ala Val Gly Leu Ala Ala Phe Ala Cys Val Leu Leu Val Val
Leu Phe Val Met Ile Asn Lys Tyr Gly Arg Arg Ser Lys Phe Gly Met
Lys Gly Pro Val Ala Val Ile Ser Gly Glu Glu Asp Ser Ala Ser Pro
Leu His His Ile Asn His Gly Ile Thr Thr Pro Ser Ser Leu Asp Ala
Gly Pro Asp Thr Val Val Ile Gly Met Thr Arg Ile Pro Val Ile Glu
Asn Pro Gln Tyr Phe Arg Gln Gly His Asn Cys His Lys Pro Asp Thr
Tyr Val Gln His Ile Lys Arg Arg Asp Ile Val Leu Lys Arg Glu Leu
Gly Glu Gly Ala Phe Gly Lys Val Phe Leu Ala Glu Cys Tyr Asn Leu
Ser Pro Thr Lys Asp Lys Met Leu Val Ala Val Lys Ala Leu Lys Asp
Pro Thr Leu Ala Ala Arg Lys Asp Phe Gln Arg Glu Ala Glu Leu Leu
Thr Asn Leu Gln His Glu His Ile Val Lys Phe Tyr Gly Val Cys Gly
Asp Gly Asp Pro Leu Ile Met Val Phe Glu Tyr Met Lys His Gly Asp
Leu Asn Lys Phe Leu Arg Ala His Gly Pro Asp Ala Met Ile Leu Val
Asp Gly Gln Pro Arg Gln Ala Lys Gly Glu Leu Gly Leu Ser Gln Met
Leu His Ile Ala Ser Gln Ile Ala Ser Gly Met Val Tyr Leu Ala Ser
Gln His Phe Val His Arg Asp Leu Ala Thr Arg Asn Cys Leu Val Gly
Ala Asn Leu Leu Val Lys Ile Gly Asp Phe Gly Met Ser Arg Asp Val
Tyr Ser Thr Asp Tyr Tyr Arg Leu Phe Asn Pro Ser Gly Asn Asp Phe
Cys Ile Trp Cys Glu Val Gly Gly His Thr Met Leu Pro Ile Arg Trp
Met Pro Pro Glu Ser Ile Met Tyr Arg Lys Phe Thr Thr Glu Ser Asp
Val Trp Ser Phe Gly Val Ile Leu Trp Glu Ile Phe Thr Tyr Gly Lys
Gln Pro Trp Phe Gln Leu Ser Asn Thr Glu Val Ile Glu Cys Ile Thr
Gln Gly Arg Val Leu Glu Arg Pro Arg Val Cys Pro Lys Glu Val Tyr
Asp Val Met Leu Gly Cys Trp Gln Arg Glu Pro Gln Gln Arg Leu Asn
Ile Lys Glu Ile Tyr Lys Ile Leu His Ala Leu Gly Lys Ala Thr Pro
Ile Tyr Leu Asp Ile Leu Gly (SEQ ID NO: 3)
``` human ALK tyrosine kinase receptor (ALK)
```
Met Gly Ala Ile Gly Leu Leu Trp Leu Leu Pro Leu Leu Leu Ser Thr
Ala Ala Val Gly Ser Gly Met Gly Thr Gly Gln Arg Ala Gly Ser Pro
Ala Ala Gly Pro Pro Leu Gln Pro Arg Glu Pro Leu Ser Tyr Ser Arg
Leu Gln Arg Lys Ser Leu Ala Val Asp Phe Val Val Pro Ser Leu Phe
Arg Val Tyr Ala Arg Asp Leu Leu Leu Pro Pro Ser Ser Ser Glu Leu
Lys Ala Gly Arg Pro Glu Ala Arg Gly Ser Leu Ala Leu Asp Cys Ala
Pro Leu Leu Arg Leu Leu Gly Pro Ala Pro Gly Val Ser Trp Thr Ala
Gly Ser Pro Ala Pro Ala Glu Ala Arg Thr Leu Ser Arg Val Leu Lys
Gly Gly Ser Val Arg Lys Leu Arg Arg Ala Lys Gln Leu Val Leu Glu
Leu Gly Glu Glu Ala Ile Leu Glu Gly Cys Val Gly Pro Pro Gly Glu
Ala Ala Val Gly Leu Leu Gln Phe Asn Leu Ser Glu Leu Phe Ser Trp
```

-continued

Sequence Listings

```
Trp Ile Arg Gln Gly Glu Gly Arg Leu Arg Ile Arg Leu Met Pro Glu
Lys Lys Ala Ser Glu Val Gly Arg Glu Gly Arg Leu Ser Ala Ala Ile
Arg Ala Ser Gln Pro Arg Leu Leu Phe Gln Ile Phe Gly Thr Gly His
Ser Ser Leu Glu Ser Pro Thr Asn Met Pro Ser Pro Ser Pro Asp Tyr
Phe Thr Trp Asn Leu Thr Trp Ile Met Lys Asp Ser Phe Pro Phe Leu
Ser His Arg Ser Arg Tyr Gly Leu Glu Cys Ser Phe Asp Phe Pro Cys
Glu Leu Glu Tyr Ser Pro Pro Leu His Asp Leu Arg Asn Gln Ser Trp
Ser Trp Arg Arg Ile Pro Ser Glu Glu Ala Ser Gln Met Asp Leu Leu
Asp Gly Pro Gly Ala Glu Arg Ser Lys Glu Met Pro Arg Gly Ser Phe
Leu Leu Leu Asn Thr Ser Ala Asp Ser Lys His Thr Ile Leu Ser Pro
Trp Met Arg Ser Ser Ser Glu His Cys Thr Leu Ala Val Ser Val His
Arg His Leu Gln Pro Ser Gly Arg Tyr Ile Ala Gln Leu Leu Pro His
Asn Glu Ala Ala Arg Glu Ile Leu Leu Met Pro Thr Pro Gly Lys His
Gly Trp Thr Val Leu Gln Gly Arg Ile Gly Arg Pro Asp Asn Pro Phe
Arg Val Ala Leu Glu Tyr Ile Ser Ser Gly Asn Arg Ser Leu Ser Ala
Val Asp Phe Phe Ala Leu Lys Asn Cys Ser Glu Thr Phe Ser Pro Gly
Ser Lys Met Ala Leu Gln Ser Ser Phe Thr Cys Trp Asn Gly Thr Val
Leu Gln Leu Gly Gln Ala Cys Asp Phe His Gln Asp Cys Ala Gln Gly
Glu Asp Glu Ser Gln Met Cys Arg Lys Leu Pro Val Gly Phe Tyr Cys
Asn Phe Glu Asp Gly Phe Cys Gly Trp Thr Gln Gly Thr Leu Ser Pro
His Thr Pro Gln Trp Gln Val Arg Thr Leu Lys Asp Ala Arg Phe Gln
Asp His Gln Asp His Ala Leu Leu Leu Ser Thr Thr Asp Val Pro Ala
Ser Glu Ser Ala Thr Val Thr Ser Ala Thr Phe Pro Ala Pro Ile Lys
Ser Ser Pro Cys Glu Leu Arg Met Ser Trp Leu Ile Arg Gly Val Leu
Arg Gly Asn Val Ser Leu Val Leu Val Glu Asn Lys Thr Gly Lys Glu
Gln Gly Arg Met Val Trp His Val Ala Ala Tyr Glu Gly Leu Ser Leu
Trp Gln Trp Met Val Leu Pro Leu Leu Asp Val Ser Asp Arg Phe Trp
Leu Gln Met Val Ala Trp Trp Gly Gln Gly Ser Arg Ala Ile Val Ala
Phe Asp Asn Ile Ser Ile Ser Leu Asp Cys Tyr Leu Thr Ile Ser Gly
Glu Asp Lys Ile Leu Gln Asn Thr Ala Pro Lys Ser Arg Asn Leu Phe
Glu Arg Asn Pro Asn Lys Glu Leu Lys Pro Gly Glu Asn Ser Pro Arg
Gln Thr Pro Ile Phe Asp Pro Thr Val His Trp Leu Phe Thr Thr Cys
Gly Ala Ser Gly Pro His Gly Pro Thr Gln Ala Gln Cys Asn Asn Ala
Tyr Gln Asn Ser Asn Leu Ser Val Glu Val Gly Ser Glu Gly Pro Leu
Lys Gly Ile Gln Ile Trp Lys Val Pro Ala Thr Asp Thr Tyr Ser Ile
Ser Gly Tyr Gly Ala Ala Gly Gly Lys Gly Gly Lys Asn Thr Met Met
Arg Ser His Gly Val Ser Val Leu Gly Ile Phe Asn Leu Glu Lys Asp
Asp Met Leu Tyr Ile Leu Val Gly Gln Gln Gly Glu Asp Ala Cys Pro
Ser Thr Asn Gln Leu Ile Gln Lys Val Cys Ile Gly Glu Asn Asn Val
Ile Glu Glu Glu Ile Arg Val Asn Arg Ser Val His Glu Trp Ala Gly
Gly Gly Gly Gly Gly Gly Ala Thr Tyr Val Phe Lys Met Lys Asp
Gly Val Pro Val Pro Leu Ile Ile Ala Ala Gly Gly Gly Gly Arg Ala
Tyr Gly Ala Lys Thr Asp Thr Phe His Pro Glu Arg Leu Glu Asn Asn
Ser Ser Val Leu Gly Leu Asn Gly Asn Ser Gly Ala Ala Gly Gly Gly
Gly Gly Trp Asn Asp Asn Thr Ser Leu Leu Trp Ala Gly Lys Ser Leu
Gln Glu Gly Ala Thr Gly Gly His Ser Cys Pro Gln Ala Met Lys Lys
Trp Gly Trp Glu Thr Arg Gly Gly Phe Gly Gly Gly Gly Gly Gly Cys
Ser Ser Gly Gly Gly Gly Gly Tyr Ile Gly Gly Asn Ala Ala Ser
Asn Asn Asp Pro Glu Met Asp Gly Glu Asp Gly Val Ser Phe Ile Ser
Pro Leu Gly Ile Leu Tyr Thr Pro Ala Leu Lys Val Met Glu Gly His
Gly Glu Val Asn Ile Lys His Tyr Leu Asn Cys Ser His Cys Glu Val
Asp Glu Cys His Met Asp Pro Glu Ser His Lys Val Ile Cys Phe Cys
Asp His Gly Thr Val Leu Ala Glu Asp Gly Val Ser Cys Ile Val
Ser Pro Thr Pro Glu Pro His Leu Pro Leu Ser Leu Ile Leu Ser
Val Val Thr Ser Ala Leu Val Ala Ala Leu Val Leu Ala Phe Ser
Gly Ile Met Ile Val Tyr Arg Arg Lys His Gln Glu Leu Gln Ala
Met Gln Met Glu Leu Gln Ser Pro Glu Tyr Lys Leu Ser Lys Leu
Arg Thr Ser Thr Ile Met Thr Asp Tyr Asn Pro Asn Tyr Cys Phe
Ala Gly Lys Thr Ser Ser Ile Ser Asp Leu Lys Glu Val Pro Arg
Lys Asn Ile Thr Leu Ile Arg Gly Leu Gly His Gly Ala Phe Gly
Glu Val Tyr Glu Gly Gln Val Ser Gly Met Pro Asn Asp Pro Ser
Pro Leu Gln Val Ala Val Lys Thr Leu Pro Glu Val Cys Ser Glu
Gln Asp Glu Leu Asp Phe Leu Met Glu Ala Leu Ile Ile Ser Lys
Phe Asn His Gln Asn Ile Val Arg Cys Ile Gly Val Ser Leu Gln
Ser Leu Pro Arg Phe Ile Leu Leu Glu Leu Met Ala Gly Gly Asp
Leu Lys Ser Phe Leu Arg Glu Thr Arg Pro Arg Pro Ser Gln Pro
Ser Ser Leu Ala Met Leu Asp Leu Leu His Val Ala Arg Asp Ile
Ala Cys Gly Cys Gln Tyr Leu Glu Glu Asn His Phe Ile His Arg
Asp Ile Ala Ala Arg Asn Cys Leu Leu Thr Cys Pro Gly Pro Gly
Arg Val Ala Lys Ile Gly Asp Phe Gly Met Ala Arg Asp Ile Tyr
Arg Ala Ser Tyr Tyr Arg Lys Gly Gly Cys Ala Met Leu Pro Val
Lys Trp Met Pro Pro Glu Ala Phe Met Glu Gly Ile Phe Thr Ser
Lys Thr Asp Thr Trp Ser Phe Gly Val Leu Leu Trp Glu Ile Phe
Ser Leu Gly Tyr Met Pro Tyr Pro Ser Lys Ser Asn Gln Glu Val
Leu Glu Phe Val Thr Ser Gly Gly Arg Met Asp Pro Pro Lys Asn
Cys Pro Gly Pro Val Tyr Arg Ile Met Thr Gln Cys Trp Gln His
Gln Pro Glu Asp Arg Pro Asn Phe Ala Ile Ile Leu Glu Arg Ile
```

Sequence Listings

```
Glu Tyr Cys Thr Gln Asp Pro Asp Val Ile Asn Thr Ala Leu Pro
Ile Glu Tyr Gly Pro Leu Val Glu Glu Glu Lys Val Pro Val
Arg Pro Lys Asp Pro Glu Gly Val Pro Pro Leu Leu Val Ser Gln
Gln Ala Lys Arg Glu Glu Arg Ser Pro Ala Ala Pro Pro Pro
Leu Pro Thr Thr Ser Ser Gly Lys Ala Ala Lys Lys Pro Thr Ala
Ala Glu Ile Ser Val Arg Val Pro Arg Gly Pro Ala Val Glu Gly
Gly His Val Asn Met Ala Phe Ser Gln Ser Asn Pro Pro Ser Glu
Leu His Lys Val His Gly Ser Arg Asn Lys Pro Thr Ser Leu Trp
Asn Pro Thr Tyr Gly Ser Trp Phe Thr Glu Lys Pro Thr Lys Lys
Asn Asn Pro Ile Ala Lys Lys Glu Pro His Asp Arg Gly Asn Leu
Gly Leu Glu Gly Ser Cys Thr Val Pro Pro Asn Val Ala Thr Gly
Arg Leu Pro Gly Ala Ser Leu Leu Leu Glu Pro Ser Ser Leu Thr
Ala Asn Met Lys Glu Val Pro Leu Phe Arg Leu Arg His Phe Pro
Cys Gly Asn Val Asn Tyr Gly Tyr Gln Gln Gln Gly Leu Pro Leu
Glu Ala Ala Thr Ala Pro Gly Ala Gly His Tyr Glu Asp Thr Ile
Leu Lys Ser Lys Asn Ser Met Asn Gln Pro Gly Pro (SEQ ID NO: 4)

human proto-oncogene tyrosine-protein kinase ROS, ROS1
Met Lys Asn Ile Tyr Cys Leu Ile Pro Lys Leu Val Asn Phe Ala Thr
Leu Gly Cys Leu Trp Ile Ser Val Val Gln Cys Thr Val Leu Asn Ser
Cys Leu Lys Ser Cys Val Thr Asn Leu Gly Gln Gln Leu Asp Leu Gly
Thr Pro His Asn Leu Ser Glu Pro Cys Ile Gln Gly Cys His Phe Trp
Asn Ser Val Asp Gln Lys Asn Cys Ala Leu Lys Cys Arg Glu Ser Cys
Glu Val Gly Cys Ser Ser Ala Glu Gly Ala Tyr Glu Glu Glu Val Leu
Glu Asn Ala Asp Leu Pro Thr Ala Pro Phe Ala Ser Ser Ile Gly Ser
His Asn Met Thr Leu Arg Trp Lys Ser Ala Asn Phe Ser Gly Val Lys
Tyr Ile Ile Gln Trp Lys Tyr Ala Gln Leu Leu Gly Ser Trp Thr Tyr
Thr Lys Thr Val Ser Arg Pro Ser Tyr Val Val Lys Pro Leu His Pro
Phe Thr Glu Tyr Ile Phe Arg Val Val Trp Ile Phe Thr Ala Gln Leu
Gln Leu Tyr Ser Pro Pro Ser Pro Ser Tyr Arg Thr His Pro His Gly
Val Pro Glu Thr Ala Pro Leu Ile Arg Asn Ile Glu Ser Ser Ser Pro
Asp Thr Val Glu Val Ser Trp Asp Pro Pro Gln Phe Pro Gly Gly Pro
Ile Leu Gly Tyr Asn Leu Arg Leu Ile Ser Lys Asn Gln Lys Leu Asp
Ala Gly Thr Gln Arg Thr Ser Phe Gln Phe Tyr Ser Thr Leu Pro Asn
Thr Ile Tyr Arg Phe Ser Ile Ala Ala Val Asn Glu Val Gly Glu Gly
Pro Glu Ala Glu Ser Ser Ile Thr Thr Ser Ser Ser Ala Val Gln Gln
Glu Glu Gln Trp Leu Phe Leu Ser Arg Lys Thr Ser Leu Arg Lys Arg
Ser Leu Lys His Leu Val Asp Glu Ala His Cys Leu Arg Leu Asp Ala
Ile Tyr His Asn Ile Thr Gly Ile Ser Val Asp Val His Gln Gln Ile
Val Tyr Phe Ser Glu Gly Thr Leu Ile Trp Ala Lys Lys Ala Ala Asn
Met Ser Asp Val Ser Asp Leu Arg Ile Phe Tyr Arg Gly Ser Gly Leu
Ile Ser Ser Ile Ser Ile Asp Trp Leu Tyr Gln Arg Met Tyr Phe Ile
Met Asp Glu Leu Val Cys Val Cys Asp Leu Glu Asn Cys Ser Asn Ile
Glu Glu Ile Thr Pro Pro Ser Ile Ser Ala Pro Gln Lys Ile Val Ala
Asp Ser Tyr Asn Gly Tyr Val Phe Tyr Leu Leu Arg Asp Gly Ile Tyr
Arg Ala Asp Leu Pro Val Pro Ser Gly Arg Cys Ala Glu Ala Val Arg
Ile Val Glu Ser Cys Thr Leu Lys Asp Phe Ala Ile Lys Pro Gln Ala
Lys Arg Ile Ile Tyr Phe Asn Asp Thr Ala Gln Val Phe Met Ser Thr
Phe Leu Asp Gly Ser Ala Ser His Leu Ile Leu Pro Arg Ile Pro Phe
Ala Asp Val Lys Ser Phe Ala Cys Glu Asn Asn Asp Phe Leu Val Thr
Asp Gly Lys Val Ile Phe Gln Gln Asp Ala Leu Ser Phe Asn Glu Phe
Ile Val Gly Cys Asp Leu Ser His Ile Glu Glu Phe Gly Phe Gly Asn
Leu Val Ile Phe Gly Ser Ser Ser Gln Leu His Pro Leu Pro Gly Arg
Pro Gln Glu Leu Ser Val Leu Phe Gly Ser His Gln Ala Leu Val Gln
Trp Lys Pro Pro Ala Leu Ala Ile Gly Ala Asn Val Ile Leu Ile Ser
Asp Ile Ile Glu Leu Phe Glu Leu Gly Pro Ser Ala Trp Gln Asn Trp
Thr Tyr Glu Val Lys Val Ser Thr Gln Asp Pro Pro Glu Val Thr His
Ile Phe Leu Asn Ile Ser Gly Thr Met Leu Asn Val Pro Glu Leu Gln
Ser Ala Met Lys Tyr Lys Val Ser Val Arg Ala Ser Ser Pro Lys Arg
Pro Gly Pro Trp Ser Glu Pro Ser Val Gly Thr Thr Leu Val Pro Ala
Ser Glu Pro Pro Phe Ile Met Ala Val Lys Glu Asp Gly Leu Trp Ser
Lys Pro Leu Asn Ser Phe Gly Pro Gly Glu Phe Leu Ser Ser Asp Ile
Gly Asn Val Ser Asp Met Asp Trp Tyr Asn Asn Ser Leu Tyr Tyr Ser
Asp Thr Lys Gly Asp Val Phe Val Trp Leu Leu Asn Gly Thr Asp Ile
Ser Glu Asn Tyr His Leu Pro Ser Ile Ala Gly Ala Gly Ala Leu Ala
Phe Glu Trp Leu Gly His Phe Leu Tyr Trp Ala Gly Lys Thr Tyr Val
Ile Gln Arg Gln Ser Val Leu Thr Gly His Thr Asp Ile Val Thr His
Val Lys Leu Leu Val Asn Asp Met Val Val Asp Ser Val Gly Gly Tyr
Leu Tyr Trp Thr Thr Leu Tyr Ser Val Glu Ser Thr Arg Leu Asn Gly
Glu Ser Ser Leu Val Leu Gln Thr Gln Pro Trp Phe Ser Gly Lys Lys
Val Ile Ala Leu Thr Leu Asp Leu Ser Asp Gly Leu Leu Tyr Trp Leu
Val Gln Asp Ser Gln Cys Ile His Leu Tyr Thr Ala Val Leu Arg Gly
Gln Ser Thr Gly Asp Thr Thr Ile Thr Glu Phe Ala Ala Trp Ser Thr
Ser Glu Ile Ser Gln Asn Ala Leu Met Tyr Tyr Ser Gly Arg Leu Phe
Trp Ile Asn Gly Phe Arg Ile Ile Thr Thr Gln Glu Ile Gly Gln Lys
Thr Ser Val Ser Val Leu Glu Pro Ala Arg Phe Asn Gln Phe Thr Ile
Ile Gln Thr Ser Leu Lys Pro Leu Pro Gly Asn Phe Ser Phe Thr Pro
```

-continued

Sequence Listings

```
Lys Val Ile Pro Asp Ser Val Gln Glu Ser Ser Phe Arg Ile Glu Gly
Asn Ala Ser Ser Phe Gln Ile Leu Trp Asn Gly Pro Pro Ala Val Asp
Trp Gly Val Val Phe Tyr Ser Val Gln Phe Ser Ala His Ser Lys Phe
Leu Ala Ser Glu Gln His Ser Leu Pro Val Phe Thr Val Glu Gly Leu
Glu Pro Tyr Ala Leu Phe Asn Leu Ser Val Thr Pro Tyr Thr Tyr
Trp Gly Lys Gly Pro Lys Thr Ser Leu Ser Leu Arg Ala Pro Glu
Thr Val Pro Ser Ala Pro Glu Asn Pro Arg Ile Phe Ile Leu Pro
Ser Gly Lys Cys Cys Asn Lys Asn Glu Val Val Val Glu Phe Arg
Trp Asn Lys Pro Lys His Glu Asn Gly Val Leu Thr Lys Phe Glu
Ile Phe Tyr Asn Ile Ser Asn Gln Ser Ile Thr Asn Lys Thr Cys
Glu Asp Trp Ile Ala Val Asn Val Thr Pro Ser Val Met Ser Phe
Gln Leu Glu Gly Met Ser Pro Arg Cys Phe Ile Ala Phe Gln Val
Arg Ala Phe Thr Ser Lys Gly Pro Gly Pro Tyr Ala Asp Val Val
Lys Ser Thr Thr Ser Glu Ile Asn Pro Phe Pro His Leu Ile Thr
Leu Leu Gly Asn Lys Ile Val Phe Leu Asp Met Asp Gln Asn Gln
Val Val Trp Thr Phe Ser Ala Glu Arg Val Ile Ser Ala Val Cys
Tyr Thr Ala Asp Asn Glu Met Gly Tyr Tyr Ala Glu Gly Asp Ser
Leu Phe Leu Leu His Leu His Asn Arg Ser Ser Ser Glu Leu Phe
Gln Asp Ser Leu Val Phe Asp Ile Thr Val Ile Thr Ile Asp Trp
Ile Ser Arg His Leu Tyr Phe Ala Leu Lys Glu Ser Gln Asn Gly
Met Gln Val Phe Asp Val Asp Leu Glu His Lys Val Lys Tyr Pro
Arg Glu Val Lys Ile His Asn Arg Asn Ser Thr Ile Ile Ser Phe
Ser Val Tyr Pro Leu Leu Ser Arg Leu Tyr Trp Thr Glu Val Ser
Asn Phe Gly Tyr Gln Met Phe Tyr Tyr Ser Ile Ile Ser His Thr
Leu His Arg Ile Leu Gln Pro Thr Ala Thr Asn Gln Gln Asn Lys
Arg Asn Gln Cys Ser Cys Asn Val Thr Glu Phe Glu Leu Ser Gly
Ala Met Ala Ile Asp Thr Ser Asn Leu Glu Lys Pro Leu Ile Tyr
Phe Ala Lys Ala Gln Glu Ile Trp Ala Met Asp Leu Glu Gly Cys
Gln Cys Trp Arg Val Ile Thr Val Pro Ala Met Leu Ala Gly Lys
Thr Leu Val Ser Leu Thr Val Asp Gly Asp Leu Ile Tyr Trp Ile
Ile Thr Ala Lys Asp Ser Thr Gln Ile Tyr Gln Ala Lys Lys Gly
Asn Gly Ala Ile Val Ser Gln Val Lys Ala Leu Arg Ser Arg His
Ile Leu Ala Tyr Ser Ser Val Met Gln Pro Phe Pro Asp Lys Ala
Phe Leu Ser Leu Ala Ser Asp Thr Val Glu Pro Thr Ile Leu Asn
Ala Thr Asn Thr Ser Leu Thr Ile Arg Leu Pro Leu Ala Lys Thr
Asn Leu Thr Trp Tyr Gly Ile Thr Ser Pro Thr Pro Thr Tyr Leu
Val Tyr Tyr Ala Glu Val Asn Asp Arg Lys Asn Ser Ser Asp Leu
Lys Tyr Arg Ile Leu Glu Phe Gln Asp Ser Ile Ala Leu Ile Glu
Asp Leu Gln Pro Phe Ser Thr Tyr Met Ile Gln Ile Ala Val Lys
Asn Tyr Tyr Ser Asp Pro Leu Glu His Leu Pro Pro Gly Lys Glu
Ile Trp Gly Lys Thr Lys Asn Gly Val Pro Glu Ala Val Gln Leu
Ile Asn Thr Thr Val Arg Ser Asp Thr Ser Leu Ile Ile Ser Trp
Arg Glu Ser His Lys Pro Asn Gly Pro Lys Glu Ser Val Arg Tyr
Gln Leu Ala Ile Ser His Leu Ala Leu Ile Pro Glu Thr Pro Leu
Arg Gln Ser Glu Phe Pro Asn Gly Arg Leu Thr Leu Leu Val Thr
Arg Leu Ser Gly Gly Asn Ile Tyr Val Leu Lys Val Leu Ala Cys
His Ser Glu Glu Met Trp Cys Thr Glu Ser His Pro Val Thr Val
Glu Met Phe Asn Thr Pro Glu Lys Pro Tyr Ser Leu Val Pro Glu
Asn Thr Ser Leu Gln Phe Asn Trp Lys Ala Pro Leu Asn Val Asn
Leu Ile Arg Phe Trp Val Glu Leu Gln Lys Trp Lys Tyr Asn Glu
Phe Tyr His Val Lys Thr Ser Cys Ser Gln Gly Pro Ala Tyr Val
Cys Asn Ile Thr Asn Leu Gln Pro Tyr Thr Ser Tyr Asn Val Arg
Val Val Val Val Tyr Lys Thr Gly Glu Asn Ser Thr Ser Leu Pro
Glu Ser Phe Lys Thr Lys Ala Gly Val Pro Asn Lys Pro Gly Ile
Pro Lys Leu Leu Glu Gly Ser Lys Asn Ser Ile Gln Trp Glu Lys
Ala Glu Asp Asn Gly Cys Arg Ile Thr Tyr Tyr Ile Leu Glu Ile
Arg Lys Ser Thr Ser Asn Asn Leu Gln Asn Gln Asn Leu Arg Trp
Lys Met Thr Phe Asn Gly Ser Cys Ser Ser Val Cys Thr Trp Lys
Ser Lys Asn Leu Lys Gly Ile Phe Gln Phe Arg Val Val Ala Ala
Asn Asn Leu Gly Phe Gly Glu Tyr Ser Gly Ile Ser Glu Asn Ile
Ile Leu Val Gly Asp Asp Phe Trp Ile Pro Glu Thr Ser Phe Ile
Leu Thr Ile Ile Val Gly Ile Phe Leu Val Val Thr Ile Pro Leu
Thr Phe Val Trp His Arg Arg Leu Lys Asn Gln Lys Ser Ala Lys
Glu Gly Val Thr Val Leu Ile Asn Glu Asp Lys Glu Leu Ala Glu
Leu Arg Gly Leu Ala Ala Gly Val Gly Leu Ala Asn Ala Cys Tyr
Ala Ile His Thr Leu Pro Thr Gln Glu Glu Ile Glu Asn Leu Pro
Ala Phe Pro Arg Glu Lys Leu Thr Leu Arg Leu Leu Leu Gly Ser
Gly Ala Phe Gly Glu Val Tyr Glu Gly Thr Ala Val Asp Ile Leu
Gly Val Gly Ser Gly Glu Ile Lys Val Ala Val Lys Thr Leu Lys
Lys Gly Ser Thr Asp Gln Glu Lys Ile Glu Phe Leu Lys Glu Ala
His Leu Met Ser Lys Phe Asn His Pro Asn Ile Leu Lys Gln Leu
Gly Val Cys Leu Leu Asn Glu Pro Gln Tyr Ile Ile Leu Glu Leu
Met Glu Gly Gly Asp Leu Leu Thr Tyr Leu Arg Lys Ala Arg Met
Ala Thr Phe Tyr Gly Pro Leu Leu Thr Leu Val Asp Leu Val Asp
Leu Cys Val Asp Ile Ser Lys Gly Cys Val Tyr Leu Glu Arg Met
His Phe Ile His Arg Asp Leu Ala Ala Arg Asn Cys Leu Val Ser
Val Lys Asp Tyr Thr Ser Pro Arg Ile Val Lys Ile Gly Asp Phe
```

Sequence Listings -continued

```
Gly Leu Ala Arg Asp Ile Tyr Lys Asn Asp Tyr Tyr Arg Lys Arg
Gly Glu Gly Leu Leu Pro Val Arg Trp Met Ala Pro Glu Ser Leu
Met Asp Gly Ile Phe Thr Thr Gln Ser Asp Val Trp Ser Phe Gly
Ile Leu Ile Trp Glu Ile Leu Thr Leu Gly His Gln Pro Tyr Pro
Ala His Ser Asn Leu Asp Val Leu Asn Tyr Val Gln Thr Gly Gly
Arg Leu Glu Pro Pro Arg Asn Cys Pro Asp Asp Leu Trp Asn Leu
Met Thr Gln Cys Trp Ala Gln Glu Pro Asp Gln Arg Pro Thr Phe
His Arg Ile Gln Asp Gln Leu Gln Leu Phe Arg Asn Phe Phe Leu
Asn Ser Ile Tyr Lys Ser Arg Asp Glu Ala Asn Asn Ser Gly Val
Ile Asn Glu Ser Phe Glu Gly Glu Asp Gly Asp Val Ile Cys Leu
Asn Ser Asp Asp Ile Met Pro Val Ala Leu Met Glu Thr Lys Asn
Arg Glu Gly Leu Asn Tyr Met Val Leu Ala Thr Glu Cys Gly Gln
Gly Glu Glu Lys Ser Glu Gly Pro Leu Gly Ser Gln Glu Ser Glu
Ser Cys Gly Leu Arg Lys Glu Glu Lys Glu Pro His Ala Asp Lys
Asp Phe Cys Gln Glu Lys Gln Val Ala Tyr Cys Pro Ser Gly Lys
Pro Glu Gly Leu Asn Tyr Ala Cys Leu Thr His Ser Gly Tyr Gly
Asp Gly Ser Asp (SEQ ID NO: 5)
```

Other embodiments are set forth in the following claims, along with the full scope of equivalents to which such claims are entitled.

What is claimed is:

1. A method of treating cancer in a patient in need thereof, the method comprising administering to the patient a combination comprising a therapeutically effective amount of a first agent and a therapeutically effective amount of a second agent, wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and the second agent is a MEK inhibitor selected from the group consisting of PD0325901, selumetinib, cobimetinib, refametinib, trametinib, pimasertib, binimetinib, AZD8330, R04987655, GDC-0623, TAK-733, sorafenib, and PD-184352; the cancer is selected from non-small cell lung cancer, papillary thyroid cancer, neuroblastoma, pancreatic cancer, melanoma, and colorectal cancer; the patient has at least one mutation in the TrkA receptor tyrosine kinase polypeptide; and the at least one mutation in the TrkA receptor tyrosine kinase polypeptide is at a position corresponding to amino acid residue G595 or G667 of the TrkA polypeptide set forth in SEQ ID NO: 1.

2. The method of claim 1, wherein the at least one mutation in the TrkA receptor tyrosine kinase polypeptide is at the position corresponding to amino acid residue G595 of the TrkA polypeptide set forth in SEQ ID NO: 1.

3. The method of claim 2, wherein the at least one mutation in the TrkA receptor tyrosine kinase polypeptide is Glu-to-Arg substitution (G595R).

4. The method of claim 1, wherein the at least one mutation in the TrkA receptor tyrosine kinase polypeptide is at the position corresponding to amino acid residue G667 of the TrkA polypeptide set forth in SEQ ID NO: 1.

5. The method of claim 4, wherein the at least one mutation in the TrkA receptor tyrosine kinase polypeptide is Glu-to-Cys substitution (G667C).

6. A method of treating cancer in a patient in need thereof, the method comprising administering to the patient a combination comprising a therapeutically effective amount of a first agent and a therapeutically effective amount of a second agent, wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and the second agent is a MEK inhibitor selected from the group consisting of PD0325901, selumetinib, cobimetinib, refametinib, trametinib, pimasertib, binimetinib, AZD8330, R04987655, GDC-0623, TAK-733, sorafenib, and PD-184352; the cancer is selected from non-small cell lung cancer, papillary thyroid cancer, neuroblastoma, pancreatic cancer, melanoma, and colorectal cancer; the patient has at least one mutation in the TrkB receptor tyrosine kinase polypeptide; and the at least one mutation in the TrkB receptor tyrosine kinase polypeptide is at a position corresponding to amino acid residue G639 or G709 of the TrkB polypeptide set forth in SEQ ID NO: 2.

7. The method of claim 6, wherein the at least one mutation in the TrkB receptor tyrosine kinase polypeptide is at the position corresponding to amino acid residue G639 of the TrkB polypeptide set forth in SEQ ID NO: 2.

8. The method of claim 7, wherein the at least one mutation in the TrkB receptor tyrosine kinase polypeptide is Glu-to-Arg substitution (G639R).

9. The method of claim 6, wherein the at least one mutation in the TrkB receptor tyrosine kinase polypeptide is at the position corresponding to amino acid residue G709 of the TrkB polypeptide set forth in SEQ ID NO: 2.

10. The method of claim 9, wherein the at least one mutation in the TrkB receptor tyrosine kinase polypeptide is Glu-to-Cys substitution (G709C).

11. A method of treating cancer in a patient in need thereof, the method comprising administering to the patient a combination comprising a therapeutically effective amount of a first agent and a therapeutically effective amount of a second agent, wherein the first agent is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and the second agent is a MEK inhibitor selected from the group consisting of PD0325901, selumetinib, cobimetinib, refametinib, trametinib, pimasertib, binimetinib, AZD8330, R04987655, GDC-0623, TAK-733, sorafenib, and PD-184352; the cancer is selected from non-small cell lung cancer, papillary thyroid cancer, neuroblastoma, pancreatic cancer, melanoma, and colorectal cancer; the patient has at least one mutation in the TrkC receptor tyrosine kinase polypeptide; and the at least one mutation in the TrkC receptor tyrosine kinase polypeptide is at a position corresponding to amino acid residue G623 or G696 of the TrkC polypeptide set forth in SEQ ID NO: 3.

12. The method of claim 11, wherein the at least one mutation in the TrkC receptor tyrosine kinase polypeptide is at the position corresponding to amino acid residue G623 of the TrkC polypeptide set forth in SEQ ID NO: 3.

13. The method of claim 12, wherein the at least one mutation in the TrkC receptor tyrosine kinase polypeptide is Glu-to-Arg substitution (G623R).

14. The method of claim 11, wherein the at least one mutation in the TrkC receptor tyrosine kinase polypeptide is at the position corresponding to amino acid residue G696 of the TrkC polypeptide set forth in SEQ ID NO: 3.

15. The method of claim 14, wherein the at least one mutation in the TrkC receptor tyrosine kinase polypeptide is Glu-to-Cys substitution (G696C).

* * * * *